US006468768B1

(12) United States Patent
Ni et al.

(10) Patent No.: US 6,468,768 B1
(45) Date of Patent: Oct. 22, 2002

(54) GALECTIN 9 AND 10SV POLYNUCLEOTIDES

(75) Inventors: Jian Ni, Rockville, MD (US); Reiner L. Gentz, Silver Spring, MD (US); Steven M. Ruben, Olney, MD (US)

(73) Assignee: Human Genome Sciences, Inc., Rockville, MD (US)

( * ) Notice: Subject to any disclaimer, the term of this patent is extended or adjusted under 35 U.S.C. 154(b) by 0 days.

(21) Appl. No.: 09/656,450

(22) Filed: Sep. 6, 2000

Related U.S. Application Data

(60) Continuation of application No. 09/263,689, filed on Mar. 5, 1999, which is a division of application No. 08/946,914, filed on Oct. 9, 1997, now Pat. No. 6,027,916.
(60) Provisional application No. 60/028,093, filed on Oct. 9, 1996.

(51) Int. Cl.[7] .......................... C12N 15/00; C12N 15/09; C12N 15/63; C12N 15/70; C12N 15/74; C07H 21/02; C07H 21/04

(52) U.S. Cl. ..................... 435/69.1; 536/23.1; 536/23.4; 536/23.5; 435/320

(58) Field of Search .............................. 536/23.1, 23.4, 536/23.5; 435/320.1, 69.1

(56) References Cited

U.S. PATENT DOCUMENTS

| 5,733,748 A | 3/1998 | Yu et al. ..................... 435/70.1 |
| 5,869,289 A | 2/1999 | Hawkins et al. ............ 435/69.1 |

FOREIGN PATENT DOCUMENTS

| EP | 0 841 393 | 5/1998 |
| WO | WO 95/14772 | 6/1995 |
| WO | WO 95/15175 | 6/1995 |
| WO | WO 96/21671 | 7/1996 |
| WO | WO 96/40209 | 12/1996 |
| WO | WO 97/03190 | 1/1997 |
| WO | WO 97/48721 | 12/1997 |

OTHER PUBLICATIONS

Burgess et al., J of Cell Bio. 111:2129–2138, 1990.*
Lazar et al. Molecular and Cellular Biology 8:1247–1252, 1988.*
Bowie et al. Science, 247:1306–1310, 1990.*
Ahmed, H. and G.R. Vasta, "Galectins: conservation of functionally and structurally relevant amino acid residues defines two types of carbohydrate recognition domains," *Glycobiol.* 4(5):545–549 (1994).
Barondes, S.H. et al., "Galectins: A Family of Animal β–Galactosidase–Binding Lectins," *Cell* 76:597–598 (1994).
Barondes, S.H. et al., "Galactins," *J. Biol. Chem.* 269(33):20807–20810 (1994).
Barondes, S.H., "Galectins: A Personal Overview," *Trends in Glycosci. & Glycotechnol.* 9(45):1–7 (Jan. 1997).
Cherayil, B.J. et al., "Molecular cloning of a human macrophage lectin specific for galactose," *Proc. Natl. Acad. Sci. USA* 87:7324–7328 (1990).
Cooper, D.N.W. et al., "Endogenous Muscle Lectin Inhibits Myoblast Adhesion to Laminin," *J. Cell Biol.* 115(5):1437–1448 (1991).
Couraud, P.–O. et al., "Molecular Cloning, Characterization, and Expression of a Human 14–kDa Lectin," *J. Biol. Chem.* 264:1310–1316 (1989).
Gitt, M.A. et al., "Isolation and Expression of a Gene Encoding L–14–II, a New Human Soluble Lactose–binding Lectin," *J. Biol. Chem.* 267(15):10601–10606 (1992).
Hadari, Y.R. et al., "Galectin–8," *J. Biol. Chem.* 270(7):3447–3453 (Feb. 1995).
Kasai, K. and J. Hirabayashi, "Galectins: A Family of Animal Lectins That Decipher Glycocodes," *J. Biochem.* 119:1–8 (Jan. 1996).
Kuwabara, I. and F.–T. Liu, "Galectin–3 Promotes Adhesion of Human Neutrophils to Laminin," *J. Immunol.* 156:3939–3944 (May 1996).
Madsen, P. et al., "Cloning, Expression, and Chromosome Mapping of Human Galectin–7," *J. Biol. Chem.* 270(11):5823–5829 (Mar. 1995).
Mey, A. et al., "The Animal Lectin Galectin–3 Interacts with Bacterial Lipopolysaccharides Via Two Independent Sites," *J. Immunol.* 156:1572–1577 (Feb. 1996).
Oda, Y. et al., "Soluble Lactose–binding Lectin from Rat Intestine with Two Different Carbohydrate–binding Domains in the Same Peptide Chain," *J. Biol. Chem.* 268:5929–5939 (1993).
Offner, H. et al., "Recombinant human β–galactoside binding lectin suppresses clinical and histological signs of experimental autoimmune encephalomyelitis," *J. Neuroimmunol.* 28:177–184 (1990).
Perillo, N.L. et al., "Apoptosis of T cells mediated by galectin–1," *Nature* 378:736–739 (Dec. 1995).
Powell, L.D. and A. Varki, "I–type Lectins," *J. Biol. Chem.* 270:14243–14246 (Jun. 1995).
Skrincosky, D.M. et al., "Galaptin–mediated Adhesion of Human Ovarian Carcinoma A121 Cells and Detection of Cellular Galaptin–binding Glycoproteins," *Cancer Res.* 53:2667–2675 (1993).

(List continued on next page.)

Primary Examiner—Anthony C. Caputa
Assistant Examiner—Natalie Davis
(74) Attorney, Agent, or Firm—Sterne, Kessler, Goldstein & Fox P.L.L.C.

(57) ABSTRACT

The present invention relates to novel galectin 8, 9, 10 and 10SV proteins which are members of the galectin superfamily. In particular, isolated nucleic acid molecules are provided encoding the human galectin 8, 9, 10 and 10SV proteins. Galectin 8, 9, 10 and 10SV polypeptides are also provided as are vectors, host cells and recombinant methods for producing the same. The invention further relates to screening methods for identifying agonists and antagonists of galectin 8, 9, 10 or 10SV activity. Also provided are diagnostic and therapeutic methods.

12 Claims, 18 Drawing Sheets

OTHER PUBLICATIONS

Su, Z.-Z. et al., "Surface–epitope masking and expression cloning identifies the human prostate carcinoma tumor antigen gene PCTA–1 a member of the galectin gene family," *Proc. Natl. Acad. Sci. USA* 93:7252–7257 (Jul. 1996).

Türeci, Ö. et al., "Molecular Definition of a Novel Human Galectin Which Is Immunogenic in Patients with Hodgkin's Disease," *J. Biol. Chem.* 272:6416–6422 (Mar. 1997).

Wells, V. and L. Mallucci, "Identification of an Autocrine Negative Growth Factor: Mouse β–Galactoside–Binding Protein Is a Cytostatic Factor and Cell Growth Regulator," *Cell* 64:91–97 (1991).

Yamaoka, A. et al., "A Human Lectin, Galectin–3 (εbp/Mac–2), Stimulates Superoxide Production by Neutrophils," *J. Immunol.* 154:3479–3487 (Apr. 1995).

Yang, R.-Y. et al., "Expression of galectin–3 modulates T–cell growth and apoptosis," *Proc. Natl. Acad. Sci. USA* 93:6737–6742 (Jun. 1996).

Zhou, Q. and R.D. Cummings, "L–14 Lectin Recognition of Laminin and Its Promotion of in Vitro Cell Adhesion," *Arch. Biochem. Biophys.* 300(1):6–17 (1993).

Genbank report, Accession No. M36682, submitted by Oda, Y. et al. (1991).

Genbank report, Accession No. S59012, submitted by Lotz, M.M. et al (1993).

Genbank report, Accession No. M64303, submitted by Raz, A. et al. (1993).

Genbank report, Accession No. D17044, submitted by Matoba, R. et al. (1994).

Genbank report, Accession No. T89447, submitted by Hillier, L. et al. (Mar. 1995).

Genbank report, Accession No. T89534, submitted by Hillier, L. et al. (Mar. 1995).

Genbank report, Accession No. L36862, submitted by Wiser, M.F. (Mar. 1995).

Genbank report, Accession No. 1083673, submitted by Hadari, Y.R. et al. (Apr. 1995).

Genbank report, Accession No. R18995, submitted by Hillier, L. et al. (Apr. 1995).

Genbank report, Accession No. L21711, submitted by Gitt, M.A. et al. (Apr. 1995).

Genbank report, Accession No. U09824, submitted by Hadari, Y.R. et al. (May 1995).

Genbank report, Accession No. R44881, submitted by Hillier, L. et al. (May 1995).

Genbank report, Accession No. H25780, submitted by Hillier, L. et al. (Jul. 1995).

Genbank report, Accession No. H29784, submitted by Hillier, L. et al. (Jul. 1995).

Genbank report, Accession No. R97308, submitted by Hillier, L. et al. (Sep. 1995).

Genbank report, Accession No. F08504, submitted by Auffray, C. et al. (Sep. 1995).

Genbank report, Accession No. H61777, submitted by Hillier, L. et al. (Oct. 1995).

Genbank report, Accession No. D25577, submitted by Okubo, K. et al. (Nov. 1995).

Genbank report, Accession No. M35368, submitted by Cherayil, B.J. et al. (Feb. 1996).

Genbank report, Accession No. Z49105, submitted by Sahin, U. et al. (Feb. 1996).

Genbank report, Accession No. N77935, submitted by Hillier, L. et al. (Mar. 1996).

Genbank report, Accession No. W07103, submitted by Hillier, L. et al. (Apr. 1996).

Genbank report, Accession No. W26014, submitted by Macke, J. et al. (May 1996).

Genbank report, Accession No. G22378, submitted by Hudson, T. (May 1996).

Genbank report, Accession No. W61989, submitted by Marra, M. et al. (Jun. 1996).

Genbank report, Accession No. C00739, submitted by Okubo, K. (Jul. 1996).

Genbank report, Accession No. AA039019, submitted by Marra, M. et al. (Aug. 1996).

Genbank report, Accession No. F14653, submitted by Winteroe, A.K. et al. (Sep. 1996).

Genbank report, Accession No. F14564, submitted by Winteroe, A.K. (Sep. 1996).

Genbank report, Accession No. AA048538, submitted by Marra, M. et al. (Sep. 1996).

Genbank report, Accession No. AA048815, submitted by Marra, M. et al. (Sep. 1996).

Genbank report, Accession No. C18591, submitted by Fujiwara, T. et al. (Sep. 1996).

Genbank report, Accession No. W08584, submitted by Marra, M. et al. (Sep. 1996).

Genbank report, Accession No. AA053238, submitted by Hillier, L. et al. (Sep. 1996).

Genbank report, Accession No. C21047, submitted by Okubo, K. (Oct. 1996).

Genbank report, Accession No. C06470, submitted by Takeda, J. (Oct. 1996).

Genbank report, Accession No. C06418, submitted by Takeda, J. (Oct. 1996).

Genbank report, Accession No. AA104050, submitted by Marra, M. et al. (Oct. 1996).

Genbank report, Accession No. H96594, submitted by Hillier, L. et al. (Nov. 1996).

Genbank report, Accession No. AA134333, submitted by Hillier, L. et al. (Nov. 1996).

Genbank report, Accession No. AA134332, submitted by Hillier, L. et al. (Nov. 1996).

Genbank report, Accession No. AA133748, submitted by Hillier, L. et al. (Nov. 1996).

Genbank report, Accession No. AA132846, submitted by Hillier, L. et al. (Nov. 1996).

Genbank report, Accession No. AA132736, submitted by Hillier, L. et al. (Nov. 1996).

Genbank report, Accession No. AA130579, submitted by Hillier, L. et al. (Nov. 1996).

Genbank report, Accession No. AA130541, submitted by Hillier, L. et al. (Nov. 1996).

Genbank report, Accession No. AA130459, submitted by Hillier, L. et al. (Nov. 1996).

Genbank report, Accession No. AA130458, submitted by Hillier, L. et al. (Nov. 1996).

Genbank report, Accession No. AA054456, submitted by Hillier, L. et al. (Dec. 1996).

Genbank report, Accession No. AA054072, submitted by Hillier, L. et al. (Dec. 1996).

Genbank report, Accession No. AA033889, submitted by Hillier, L. et al. (Feb. 1997).

Genbank report, Accession No. AA072610, submitted by Marra, M. et al. (Feb. 1997).

Genbank report, Accession No. AA144988, submitted by Marra, M. et al. (Feb. 1997).

Genbank report, Accession No. AA139927, submitted by Marra, M. et al. (Feb. 1997).
Genbank report, Accession No. AA230865, submitted by Marra, M. et al. (Feb. 1997).
Genbank report, Accession No. AA245362, submitted by Marra, M. et al. (Mar. 1997).
Genbank report, Accession No. AA245359, submitted by Marra, M. et al. (Mar. 1997).
Genbank report, Accession No. AA250039, submitted by Marra, M. et al. (Mar. 1997).
Genbank report, Accession No. AA265377, submitted by Marra, M. et al. (Mar. 1997).
Genbank report, Accession No. AA265997, submitted by Marra, M. et al. (Mar. 1997).
Genbank report, Accession No. AA265412, submitted by Marra, M. et al. (Mar. 1997).
Genbank report, Accession No. AA272305, submitted by Marra, M. et al. (Mar. 1997).
Genbank report, Accession No. AA276637, submitted by Marra, M. et al. (Apr. 1997).
Genbank report, Accession No. Z49107, submitted by Tureci, O. et al. (Apr. 1997).
Genbank report, Accession No. W85928, submitted by Hillier, L. et al. (May 1997).
Genbank report, Accession No. AA055636, submitted by Hillier, L. et al. (May 1997).
Genbank report, Accession No. AA099805, submitted by Hillier, L. et al. (May 1997).
Genbank report, Accession No. AA100290, submitted by Hillier, L. et al. (May 1997).
Genbank report, Accession No. AA102277, submitted by Hillier, L. et al. (May 1997).
Genbank report, Accession No. AA100297, submitted by Hillier, L. et al. (May 1997).
Genbank report, Accession No. AA115664, submitted by Hillier, L. et al. (May 1997).
Genbank report, Accession No. AA126912, submitted by Hillier, L. et al. (May 1997).
Genbank report, Accession No. AA127117, submitted by Hillier, L. et al. (May 1997).
Genbank report, Accession No. AA134251, submitted by Hillier, L. et al. (Aug. 1997).
Genbank report, Accession No. AA132090, submitted by Hillier, L. et al. (Aug. 1997).
Genbank report, Accession No. AA130403, submitted by Hillier, L. et al. (Aug. 1997).
Genbank report, Accession No. AA130530, submitted by Hillier, L. et al. (Aug. 1997).
Genbank report, Accession No. AA132714, submitted by Hillier, L. et al. (Aug. 1997).
Genbank report, Accession No. AA132843, submitted by Hillier, L. et al. (Aug. 1997).
Genbank report, Accession No. AA132779, submitted by Hillier, L. et al. (Aug. 1997).
Genbank report, Accession No. AA134398, submitted by Hillier, L. et al. (Aug. 1997).
Genbank report, Accession No. AA134397, submitted by Hillier, L. et al. (Aug. 1997).
Genbank report, Accession No. AA134372, submitted by Hillier, L. et al. (Aug. 1997).
Genbank report, Accession No. AA134371, submitted by Hillier, L. et al. (Aug. 1997).
Genbank report, Accession No. W11413, submitted by Marra, M. et al. (Oct. 1997).
Genbank report, Accession No. W11732, submitted by Marra, M. et al. (Oct. 1997).
Genbank report, Accession No. W12871, submitted by Marra, M. et al. (Oct. 1997).
GenBank Report, Accession No. AA295767, Adams, M.D. et al. (Apr. 1997).
GenBank Report, Accession No. AA295169, Adams, M.D. et al. (Apr. 1997).
GenBank Report, Accession No. AA297149, Adams, M.D. et al. (Apr. 1997).
GenBank Report, Accession No. AA316534, Adams, M.D. et al. (Apr. 1997).
GenBank Report, Accession No. AA354210, Adams, M.D. et al. (Apr. 1997).
GenBank Report, Accession No. AA382104, Adams, M.D. et al. (Apr. 1997).
GenBank Report, Accession No. AA353933, Adams, M.D. et al. (Apr. 1997).
GenBank Report, Accession No. AA354814, Adams, M.D. et al. (Apr. 1997).
GenBank Report, Accession No. AA404010, Marra, M. et al. (Apr. 1997).
GenBank Report, Accession No. AA443641, Hillier, L. et al. (Jun. 1997).
GenBank Report, Accession No. AA475856, Marra, M. et al. (Jun. 1997).
GenBank Report, Accession No. AA498593, Marra, M. et al. (Jul. 1997).
GenBank Report, Accession No. AA499921, Marra, M. et al. (Jul. 1997).
GenBank Report, Accession No. AA521753, Marra, M. et al. (Jul. 1997).
GenBank Report, Accession No. AA530607, Marra, M. et al. (Jul. 1997).
GenBank Report, Accession No. AA484985, NCI–CGAP (Aug. 1997).
GenBank Report, Accession No. AA606516, Marra, M. et al. (Sep. 1997).
GenBank Report, Accession No. AA428401, Hillier, L. et al. (Oct. 1997).
GenBank Report, Accession No. AA478365, Hillier, L. et al. (Nov. 1997).
GenBank Report, Accession No. AA477070, Hillier, L. et al. (Nov. 1997).
GenBank Report, Accession No. AA476845, Hillier, L. et al. (Nov. 1997).
GenBank Report, Accession No. AA674445, Marra, M. et al. (Nov. 1997).
GenBank Report, Accession No. AA690448, Marra, M. et al. (Dec. 1997).
GenBank Report, Accession No. AA759828, Marra, M. et al. (Jan. 1998).
GenBank Report, Accession No. AA822284, Marra, M. et al. (Feb. 1998).
GenBank Report, Accession No. AA810306, NCI–CGAP (Feb. 1998).
GenBank Report, Accession No. AA887943, NCI–CGAP (Apr. 1998).
GenBank Report, Accession No. AI043229, Marra, M. et al. (Jul. 1998).
GenBank Report, Accession No. AI042826, Marra, M. et al. (Jul. 1998).

GenBank Report, Accession No. AI048975, Marra, M. et al. (Jul. 1998).

GenBank Report, Accession No. AA993632, NCI–CGAP et al. (Aug. 1998).

MPSRCH Database Search, Accession No. JC6147, Su, Z.Z. et al. (1995).

MPSRCH Database Search, Accession No. T21230, Matsubara, K. et al. (1996).

International Search Report for International Application No. PCT/US97/18261, mailed Mar. 16, 1998.

Matsubara, K. and Okubo, K., Geneseq Database Accession No. AAT26065 (Jun. 1995).

Su et al., Genebank Accession No. 000214 (1996).

* cited by examiner

```
                    10                  30                  50
          TTCGGCACGAGAGCTCTTCTCACAGGACCAGCCACTAGCGCACCTCGAGCGATGGCCTAT
                                                              M  A  Y
                    70                  90                 110
          GTCCCCGCACCGGGCTACCAGCCCACCTACAACCCGACGCTGCCTTACTACCAGCCCATC
           V  P  A  P  G  Y  Q  P  T  Y  N  P  T  L  P  Y  Y  Q  P  I
                   130                 150                 170
          CCGGGCGGGCTCAACGTGGGAATGTCTGTTTACATCCAAGGAGTGGCCAGCGAGCACATG
           P  G  G  L  N  V  G  M  S  V  Y  I  Q  G  V  A  S  E  H  M
                   190                 210                 230
          AAGCGGTTCTTCGTGAACTTTGTGGTTGGGCAGGATCCGGGCTCAGACGTCGCCTTCCAC
           K  R  F  F  V  N  F  V  V  G  Q  D  P  G  S  D  V  A  F  H
                   250                 270                 290
          TTCAATCCGCGGTTTGACGGCTGGGACAAGGTGGTCTTCAACACGTTGCAGGGCGGGAAG
           F  N  P  R  F  D  G  W  D  K  V  V  F  N  T  L  Q  G  G  K
                   310                 330                 350
          TGGGGCAGCGAGGAGAGGAAGAGGAGCATGCCCTTCAAAAAGGGTGCCGCCTTTGAGCTG
           W  G  S  E  E  R  K  R  S  M  P  F  K  K  G  A  A  F  E  L
                   370                 390                 410
          GTCTTCATAGTCCTGGCTGAGCACTACAAGGTGGTGGTAAATGGAAATCCCTTCTATGAG
           V  F  I  V  L  A  E  H  Y  K  V  V  V  N  G  N  P  F  Y  E
                   430                 450                 470
          TACGGGCACCGGCTTCCCCTACAGATGGTCACCCACCTGCAAGTGGATGGGGATCTGCAA
           Y  G  H  R  L  P  L  Q  M  V  T  H  L  Q  V  D  G  D  L  Q
                   490                 510                 530
          CTTCAATCAATCAACTTCATCGGAGGCCAGCCCCTCCGGCCCCAGGGACCCCCGATGATG
           L  Q  S  I  N  F  I  G  G  Q  P  L  R  P  Q  G  P  P  M  M
                   550                 570                 590
          CCACCTTACCCTGGTCCCGGACATTGCCATCAACAGCTGAACAGCCTGCCCACCATGGAA
           P  P  Y  P  G  P  G  H  C  H  Q  Q  L  N  S  L  P  T  M  E
                   610                 630                 650
          GGACCCCCAACCTTCAACCCGCCTGTGCCATATTTCGGGAGGCTGCAAGGAGGGCTCACA
           G  P  P  T  F  N  P  P  V  P  Y  F  G  R  L  Q  G  G  L  T
                   670                 690                 710
          GCTCGAAGAACCATCATCATCAAGGGCTATGTGCCTCCCACAGGCAAGAGCTTTGCTATC
           A  R  R  T  I  I  I  K  G  Y  V  P  P  T  G  K  S  F  A  I
                   730                 750                 770
          AACTTCAAGGTGGGCTCCTCAGGGGACATAGCTCTGCACATTAATCCCCGCATGGGCAAC
           N  F  K  V  G  S  S  G  D  I  A  L  H  I  N  P  R  M  G  N
                   790                 810                 830
          GGTACCGTGGTCCGGAACAGCCTTCTGAATGGCTCGTGGGGATCCGAGGAGAAGAAGATC
           G  T  V  V  R  N  S  L  L  N  G  S  W  G  S  E  E  K  K  I
                   850                 870                 890
          ACCCACAACCCATTTGGTCCCGGACAGTTCTTTGATCTGTCCATTCGCTGTGGCTTGGAT
           T  H  N  P  F  G  P  G  Q  F  F  D  L  S  I  R  C  G  L  D
                   910                 930                 950
          CGCTTCAAGGTTTACGCCAATGGCCAGCACCTCTTTGACTTTGCCCATCGCCTCTCGGCC
           R  F  K  V  Y  A  N  G  Q  H  L  F  D  F  A  H  R  L  S  A
                   970                 990                1010
          TTCCAGAGGGTGGACACATTGGAAATCCAGGGTGATGTCACCTTGTCCTATGTCCAGATC
           F  Q  R  V  D  T  L  E  I  Q  G  D  V  T  L  S  Y  V  Q  I
                  1030                1050                1070
          TAATCTATTCCTGGGGCCATAACTCATGGGAAAACAGAATTATCCCCTAGGACTCCTTTC
           *
                  1090                1110                1130
          TAAGCCCCTAATAAAATGTCTGAGGGTGTCTCATGAAAAAAAAAAAAAAAAAAAAAAAAA
```

FIG.1

```
                10                  30                  50
AGAGGCGGCGGAGAGATGGCCTTCAGCGGTTCCCAGGCTCCCTACCTGAGTCCAGCTGTC
                 M  A  F  S  G  S  Q  A  P  Y  L  S  P  A  V
                70                  90                 110
CCCTTTTCTGGGACTATTCAAGGAGGTCTCCAGGACGGACTTCAGATCACTGTCAATGGG
 P  F  S  G  T  I  Q  G  G  L  Q  D  G  L  Q  I  T  V  N  G
               130                 150                 170
ACCGTTCTCAGCTCCAGTGGAACCAGGTTTGCTGTGAACTTTCAGACTGGCTTCAGTGGA
 T  V  L  S  S  S  G  T  R  F  A  V  N  F  Q  T  G  F  S  G
               190                 210                 230
AATGACATTGCCTTCCACTTCAACCCTCGGTTTGAAGATGGAGGGTACGTGGTGTGCAAC
 N  D  I  A  F  H  F  N  P  R  F  E  D  G  G  Y  V  V  C  N
               250                 270                 290
ACGAGGCAGAACGGAAGCTGGGGGCCCGAGGAGAGGAAGACACACATGCCTTTCCAGAAG
 T  R  Q  N  G  S  W  G  P  E  E  R  K  T  H  M  P  F  Q  K
               310                 330                 350
GGGATGCCCTTTGACCTCTGCTTCCTGGTGCAGAGCTCAGATTTCAAGGTGATGGTGAAC
 G  M  P  F  D  L  C  F  L  V  Q  S  S  D  F  K  V  M  V  N
               370                 390                 410
GGGATCCTCTTCGTGCAGTACTTCCACCGCGTGCCCTTCCACCGTGTGGACACCATCTCC
 G  I  L  F  V  Q  Y  F  H  R  V  P  F  H  R  V  D  T  I  S
               430                 450                 470
GTCAATGGCTCTGTGCAGCTGTCCTACATCAGCTTCCAGACCCAGACAGTCATCCACACA
 V  N  G  S  V  Q  L  S  Y  I  S  F  Q  T  Q  T  V  I  H  T
               490                 510                 530
GTGCAGAGCGCCCCTGGACAGATGTTCTCTACTCCCGCCATCCCACCTATGATGTACCCC
 V  Q  S  A  P  G  Q  M  F  S  T  P  A  I  P  P  M  M  Y  P
               550                 570                 590
CACCCCGCCTATCCGATGCCTTTCATCACCACCATTCTGGGAGGGCTGTACCCATCCAAG
 H  P  A  Y  P  M  P  F  I  T  T  I  L  G  G  L  Y  P  S  K
               610                 630                 650
TCCATCCTCCTGTCAGGCACTGTCCTGCCCAGTGCTCAGAGGTTCCACATCAACCTGTGC
 S  I  L  L  S  G  T  V  L  P  S  A  Q  R  F  H  I  N  L  C
               670                 690                 710
TCTGGGAACCACATCGCCTTCCACCTGAACCCCCGTTTTGATGAGAATGCTGTGGTCCGC
 S  G  N  H  I  A  F  H  L  N  P  R  F  D  E  N  A  V  V  R
               730                 750                 770
AACACCCAGATCGACAACTCCTGGGGGTCTGAGGAGCGAAGTCTGCCCCGAAAAATGCCC
 N  T  Q  I  D  N  S  W  G  S  E  E  R  S  L  P  R  K  M  P
               790                 810                 830
TTCGTCCGTGGCCAGAGCTTCTCAGTGTGGATCTTGTGTGAAGCTCACTGCCTCAAGGTG
 F  V  R  G  Q  S  F  S  V  W  I  L  C  E  A  H  C  L  K  V
               850                 870                 890
GCCGTGGATGGTCAGCACCTGTTTGAATACTACCATCGCCTGAGGAACCTGCCCACCATC
 A  V  D  G  Q  H  L  F  E  Y  Y  H  R  L  R  N  L  P  T  I
               910                 930                 950
AACAGACTGGAAGTGGGGGGCGACATCCAGCTGACCCATGTGCAGACATAGGCGGCTTCC
 N  R  L  E  V  G  G  D  I  Q  L  T  H  V  Q  T  *
               970                 990                1010
TGGCCCTGGGGCCGGGGGCTGGGGTGTGGGGCAGTCTGGGTCCTCTCATCATCCCCACTT
              1030                1050                1070
CCCAGGCCCAGCCTTTCCAACCCTGCCTGGGATCTGGGCTTTAATGCAGAGGCCATGTCC
              1090                1110                1130
TTGTCTGGTCCTGCTTCTGGCTACAGCCACCCTGGAACGGAGAAGGCAGCTGACGGGGAT
```

FIG.2A

```
      1150                1170                1190
TGCCTTCCTCAGCCGCAGCAGCACCTGGGGCTCCAGCTGCTGGAAATCCTACCATCCCAG
      1210                1230                1250
GAGGCAGGCACAGCCAGGGAGAGGGGAGGAGTGGGCAGTGAAGATGAAGCCCCATGCTCA
      1270                1290                1310
GTCCCCTCCCATCCCCCACGCAGCTCCACCCCAGTCCCAAGCCACCAGCTGTCTGCTCCT
      1330                1350                1370
GGTGGGAGGTGGCCTCCTCAGCCCCTCCTCTCTGACCTTTAACCTCACTCTCACCTTGCA
      1390                1410                1430
CCGTGCACCAACCCTTCACCCCTCCTGGAAAGCAGGCCTGATGGCTTCCCACTGGCCTCC
      1450                1470                1490
ACCACCTGACCAGAGTGTTCTCTTCAGAGGACTGGCTCCTTTCCCAGTGTCCTTAAAATA
      1510                1530
AAGAAATGAAAATGCTTGTTGGCAAAAAAAAAAAAAAAAAAAAAA
```

FIG.2B

```
                10                      30                      50
    ACACCAGTCTTTGGGGCCAGTGCCTCAGTTTCAATCCAGGTAACCTTTAAATGAAACTTG
                70                      90                     110
    CCTAAAATCTTAGGTCATACACAGAAGAGACTCCAATCGACAAGAAGCTGGAAAAGAATG
                                                               M
               130                     150                     170
    ATGTTGTCCTTAAACAACCTACAGAATATCATCTATAACCCGGTAATCCCGTTTGTTGGC
     M  L  S  L  N  N  L  Q  N  I  I  Y  N  P  V  I  P  F  V  G
               190                     210                     230
    ACCATTCCTGATCAGCTGGATCCTGGAACTTTGATTGTGATACGTGGGCATGTTCCTAGT
     T  I  P  D  Q  L  D  P  G  T  L  I  V  I  R  G  H  V  P  S
               250                     270                     290
    GACGCAGACAGATTCCAGGTGGATCTGCAGAATGGCAGCAGTGTGAAACCTCGAGCCGAT
     D  A  D  R  F  Q  V  D  L  Q  N  G  S  S  V  K  P  R  A  D
               310                     330                     350
    GTGGCCTTTCATTTCAATCCTCGTTTCAAAAGGGCCGGCTGCATTGTTTGCAATACTTTG
     V  A  F  H  F  N  P  R  F  K  R  A  G  C  I  V  C  N  T  L
               370                     390                     410
    ATAAATGAAAAATGGGGACGGGAAGAGATCACCTATGACACGCCTTTCAAAAGAGAAAAG
     I  N  E  K  W  G  R  E  E  I  T  Y  D  T  P  F  K  R  E  K
               430                     450                     470
    TCTTTTGAGATCGTGATTATGGTGCTAAAGGACAAATTCCAGGTGGCTGTAAATGGAAAA
     S  F  E  I  V  I  M  V  L  K  D  K  F  Q  V  A  V  N  G  K
               490                     510                     530
    CATACTCTGCTCTATGGCCACAGGATCGGCCCAGAGAAAATAGACACTCTGGGCATTTAT
     H  T  L  L  Y  G  H  R  I  G  P  E  K  I  D  T  L  G  I  Y
               550                     570                     590
    GGCAAAGTGAATATTCACTCAATTGGTTTTAGCTTCAGCTCGGACTTACAAAGTACCCAA
     G  K  V  N  I  H  S  I  G  F  S  F  S  S  D  L  Q  S  T  Q
               610                     630                     650
    GCATCTAGTCTGGAACTGACAGAGATAGTTAGAGAAAATGTTCCAAAGTCTGGCACGCCC
     A  S  S  L  E  L  T  E  I  V  R  E  N  V  P  K  S  G  T  P
               670                     690                     710
    CAGCTTAGCCTGCCATTCGCTGCAAGGTTGAACACCCCCATGGGCCCTGGACGAACTGTC
     Q  L  S  L  P  F  A  A  R  L  N  T  P  M  G  P  G  R  T  V
               730                     750                     770
    GTCGTTAAAGGAGAAGTGAATGCAAATGCCAAAAGCTTTAATGTTGACCTACTAGCAGGA
     V  V  K  G  E  V  N  A  N  A  K  S  F  N  V  D  L  L  A  G
               790                     810                     830
    AAATCAAAGGATATTGCTCTACACTTGAACCCACGCCTGAATATTAAAGCATTTGTGAGA
     K  S  K  D  I  A  L  H  L  N  P  R  L  N  I  K  A  F  V  R
               850                     870                     890
    AATTCTTTTCTTCAAGAGTCCTGGGGAGAAGAAGAGAGAAATATTACCGCTTTCCCATTT
     N  S  F  L  Q  E  S  W  G  E  E  E  R  N  I  T  A  F  P  F
               910                     930                     950
    AGTCCTGGGATGTACTTTGAGATGATAATTTATTGTGATGTTAGAGAATTCAAGGTTGCA
     S  P  G  M  Y  F  E  M  I  I  Y  C  D  V  R  E  F  K  V  A
               970                     990                    1010
    GTAAATGGCGTACACAGCCTGGAGTACAAACACAGATTTAAAGAGCTCAGCAGTATTGAC
     V  N  G  V  H  S  L  E  Y  K  H  R  F  K  E  L  S  S  I  D
              1030                    1050                    1070
    ACGCTGGAAATTAATGGAGACATCCACTTACTGGAAGTAAGGAGCTGGTAGCCTACCTAC
     T  L  E  I  N  G  D  I  H  L  L  E  V  R  S  W  *
```

FIG.3A

```
         1090                1110                1130
ACAGCTGCTACAAAAACCAAAATACAGAATGGCTTCTGTGATACTGGCCTTGCTGAAACG
         1150                1170                1190
CATCTCACTGTCATTCTATTGTTTATATTGTTAAAATGAGCTTGTGCACCATTAGGTCCT
         1210                1230                1250
GCTGGGTGTTCTCAGTCCTTGCCATGAAGTATGGTGGTGTCTAGCACTGAATGGGGAAAC
         1270                1290                1310
TGGGGGCAGCAACACTTATAGCCAGTTAAAGCCACTCTGCCCTCTCTCCTACTTTGGCTG
         1330                1350                1370
ACTCTTCAAGAATGCCATTCAACAAGTATTTATGGAGTCCTACTATATACAGTAGCTAAC
         1390                1410                1430
ATGTATTGAGCACAGATTTTTTTGGTAAACCTGTGAGGGCTAGGGTATATCCTTGGGAAC
         1450                1470
AAACCAGAATGTCCTGTCCCTTGAAAAAAAAAAAAAAAA
```

FIG.3B

```
ACACCAGTCTTTGGGGCCAGTGCCTCAGTTTCAATCCAGGTAACCTTTAAATGAAACTTG
CCTAAAATCTTAGGTCATACACAGAAGAGACTCCAATCGACAAGAAGCTGGAAAAGAATG
                                                           M
ATGTTGTCCTTAAACAACCTACAGAATATCATCTATAACCCGGTAATCCCGTTTGTTGGC
 M L S L N N L Q N I I Y N P V I P F V G

ACCATTCCTGATCAGCTGGATCCTGGAACTTTGATTGTGATACGTGGGCATGTTCCTAGT
 T I P D Q L D P G T L I V I R G H V P S

GACGCAGACAGATTCCAGGTGGATCTGCAGAATGGCAGCAGCATGAAACCTCGAGCCGAT
 D A D R F Q V D L Q N G S S M K P R A D

GTGGCCTTTCATTTCAATCCTCGTTTCAAAAGGGCCGGCTGCATTGTTTGCAATACTTTG
 V A F H F N P R F K R A G C I V C N T L

ATAAATGAAAAATGGGGACGGGAAGAGATCACCTATGACACGCCTTTCAAAAGAGAAAAG
 I N E K W G R E E I T Y D T P F K R E K

TCTTTTGAGATCGTGATTATGGTGCTGAAGGACAAATTCCAGGTGGCTGTAAATGGAAAA
 S F E I V I M V L K D K F Q V A V N G K

CATACTCTGCTCTATGGCCACAGGATCGGCCCAGAGAAAATAGACACTCTGGGCATTTAT
 H T L L Y G H R I G P E K I D T L G I Y

GGCAAAGTGAATATTCACTCAATTGGTTTTAGCTTCAGCTCGGACTTACAAAGTACCCAA
 G K V N I H S I G F S F S S D L Q S T Q

GCATCTAGTCTGGAACTGACAGAGATAAGTAGAGAAAATGTTCCAAAGTCTGGCACGCCC
 A S S L E L T E I S R E N V P K S G T P

CAGCTTGTGAGTATTTTTGCCTGGGTTATTTCATGTGGAATATTTTATAAAGTTGCATAG
 Q L V S I F A W V I S C G I F Y K V A *

AAAATGAACAGTTTAAACCGTGGAGGGCAGCTTCATTCATTCCATTCCTTACTGTAGAAC
TGTTTCCCTACAGCCTAGTAATAGAGGAGGAGACATTTCTAAAATCGCACCCAGAACTGT
CTACACCAAGAGCAAAGATTCGACTGTCAATCACACTTTGACTTGCACCAAAATACCACC
TATGAACTATGTGTCAAAGGGTTTGAAGAGCACCAAATTTTCTTAACTCTATATAAAAAT
TAAGTTGTAATGAGCTGTTACGAGTAACCTGTATCCACAATAGAGGCCCAAAGCAGCCCC
CTCTGCATTTGTGTGCCGTCCCTGGACGGATTCGAGAGTCAACCAGGCCTGCCTCTGAGC
CATTTCTGTGTATTTCCTCAGCACCTCCCTGCTTGGCTGCTTCCCCTTCAGGCAGAACAC
AGTACTGCCTCAGACCCCAGGCACAGGGGGCCTTCCTGGCGTGTTTCACTCATACAGAGG
GCATCGGGTCCCACCCTGTCACTCATTTCATCGTCTAAAATGTAATCATGTGTGTTTGCT
TCGAGCCAGGGACAGTGCTGCTGCAGGGGACCCAGCTGGGACCAAGGCAGACTGTCTCTC
CCCTCCTGGGATTTACAGGGTCATGGCTCTGAAACATTCCGTAGTGTTCTTTGGACACGA
GTTTTCCCTGGAGATCGCTTTCTGCAGGCTCTTGGTCCTGACTGTGGCTTCTTTTCAGAG
GCTGCCATTTCGCTGCAAGGTTGAACACCCCATGGGCCCTGGACGAACTGTCGTCGTTA
AAGGAGAAGTGAATGCAAATGCCAAAAGCTTTAATGTTGACCTACTAGCAGGAAAATCAA
AGGATATTGCTCTACACTTGAACCCACGCCTGAATATTAAAGCATTTGTAAGAAATTCTT
TTCTTCAGGAGTCCTGGGGAGAAGAAGAGAGAAATATTACCTCTTTCCCATTTAGTCCTG
GGATGTACTTTGAGATGATAATTTATTGTGATGTTAGAGAATTCAAGGTTGCAGTAAATG
GCGTACACAGCCTGGAGTACAAACACAGATTTTAAAGAGCTCAGCAGTATTGACACGCTGG
AAATTAATGGAGACATCCACTTACTGGAAGTAAGGAGCTGGTAGCCTACCTACACAGCTG
```

FIG.4A

CTACAAAAACCAAAATACAGAATGGCTTCTGTGATACTGGCCTTGCTGAAACGCAAAAAA
AAAAAAAAAAAAAAAA

| | | | | | | | | | Galectin 2 hu |
|---|---|---|---|---|---|---|---|---|---|
| | | | | | | | | | Galectin 3 hu |
| | | | | | | | | | Galectin 4 rat |
| | | | | | | | | | Galectin 5 rat |
| | | | | | | | | | Galectin 7 hu |
| | | | | | | | | | Galectin 3 rat |
| | | | | | | | | | Galectin 8 rat |
| | | | | | | | | | Galectin 1 hu |
| | | | | | | | | | Galectin 8 hu |
| | | | | | | | | | Galectin 9 hu |
| | | | | | | | | | Galectin 10 |

| 118 | S | V | R | G | G | F | N | M | S | S | F | K | L | K | – | E |
| 235 | G | I | S | G | D | I | D | L | T | S | A | S | Y | T | M | I |
| 312 | E | I | K | G | D | I | T | L | S | Y | V | Q | – | I | – | I |
| 133 | E | V | A | G | D | I | Q | L | T | H | V | E | – | I | – | T |
| 123 | E | V | G | G | D | V | Q | L | D | S | V | R | – | I | – | F |
| 247 | G | I | I | G | D | I | T | L | T | S | A | S | H | A | M | I |
| 303 | A | V | D | G | D | I | R | L | L | D | V | R | – | S | W | |
| 122 | A | A | D | G | D | F | K | I | K | C | V | A | F | – | I | – | D |
| 311 | E | I | Q | G | D | V | T | L | S | Y | V | Q | – | I | – | |
| 299 | E | V | G | G | D | I | Q | L | T | H | V | Q | – | I | – | T |
| 304 | E | I | N | G | D | I | H | L | L | E | V | R | – | S | W | |

FIG.5E

Galectin10SV.aa
x
RatRL30.aa

Percent Similarity: 84.422   Percent Identity: 71.357

```
  2   MLSLNNLQNIIYNPVIPFVGTIPDQLDPGTLIVIRGHVPSDADRFQVDLQ    51
      ||||.||||||||||.||:|:||.||.||||||||||.|.:|||||:|
  1   MLSLSNLQNIIYNPTIPYVSTITEQLKPGSLIVIRGHVPKDSERFQVDFQ    50

52   NGSSMKPRADVAFHFNPRFKRAGCIVCNTLINEKWGREEITYDTPFKREK   101
      :|.|:||||||||||||||||..|||||||.||||:||||.| ||::||
 51   HGNSLKPRADVAFHFNPRFKRSNCIVCNTLTNEKWGWEEITHDMPFRKEK   100

102   SFEIVIMVLKDKFQVAVNGKHTLLYGHRIGPEKIDTLGIYGKVNIHSIGF   151
      ||||||||||:||:|||||||.|||:|||.|||||||||:||||||||||
101   SFEIVIMVLKNKFHVAVNGKHILLYAHRINPEKIDTLGIFGKVNIHSIGF   150

152   SFSSDLQSTQASSLELTEISRENVPKSGTPQL.VSIFAWVISC.....GI   195
      .|||||| :.|.|:||:||:||.|||. :| :..: |:: ..     ..:
151   RFSSDLQSMETSTLGLTQISKENIQKSGKLHLSLPFEARLNASMGPGRTV   200

196   FYKVA   200
      . |..
201   VVKGE   205
```

FIG.6

```
                        Galectin10.aa
                             x
                        Galectin10SV.aa Gal-10      1    MMLSLNNLQNIIYNPVIPFVGTIPDQLDPGTLIVIRGHVPSDADRFQVDL    50
                 ||||||||||||||||||||||||||||||||||||||||||||||||||
Gal-10SV    1    MMLSLNNLQNIIYNPVIPFVGTIPDQLDPGTLIVIRGHVPSDADRFQVDL    50

Gal-10     51    QNGSSVKPRADVAFHFNPRFKRAGCIVCNTLINEKWGREEITYDTPFKRE   100
                 |||||:||||||||||||||||||||||||||||||||||||||||||||
Gal-10SV   51    QNGSSMKPRADVAFHFNPRFKRAGCIVCNTLINEKWGREEITYDTPFKRE   100

Gal-10    101    KSFEIVIMVLKDKFQVAVNGKHTLLYGHRIGPEKIDTLGIYGKVNIHSIG   150
                 ||||||||||||||||||||||||||||||||||||||||||||||||||
Gal-10SV  101    KSFEIVIMVLKDKFQVAVNGKHTLLYGHRIGPEKIDTLGIYGKVNIHSIG   150

Gal-10    151    FSFSSDLQSTQASSLELTEIVRENVPKSGTPQLSLPFAARLNTPMGPGRT   200
                 |||||||||||||||||||||| ||||||||||||   ||   :....:
Gal-10SV  151    FSFSSDLQSTQASSLELTEISRENVPKSGTPQLVSIFAWVISCGIFYKVA   200

Gal-10    201    VVVKGEVNANAKSFNVDLLAGKSKDIALHLNPRLNIKAFVRNSFLQESWG   250

Gal-10    251    EEERNITAFPFSPGMYFEMIIYCDVREFKVAVNGVHSLEYKHRFKELSSI   300

Gal-10    301    DTLEINGDIHLLEVRSW    317
```

GALECTIN 9 AND 10SV POLYNUCLEOTIDES

The present application is a continuation of U.S. application Ser. No. 09/263,689, filed Mar. 5, 1999, which is incorporated herein by reference; said U.S. application Ser. No. 09/263,689 is a divisional of U.S. application Ser. No. 08/946,914, filed Oct. 9, 1997 (issued as U.S. Pat. No. 6,027,916), which is herein incorporated by reference; said U.S. application Ser. No. 08/946,914 claims the benefit of U.S. Provisional Application No. 60/028,093, filed on Oct. 9, 1996, which is herein incorporated by reference.

BACKGROUND OF THE INVENTION

1. Field of the Invention

The present invention relates to novel galectins. More specifically, isolated nucleic acid molecules are provided encoding human galectin 8, 9, 10, or 10SV. Galectin 8, 9, 10 and 10SV polypeptides are also provided, as are vectors, host cells and recombinant methods for producing the same. The invention further relates to screening methods for identifying agonists and antagonists of galectin 8, 9, 10, or 10SV activity. Also provided are diagnostic methods for detecting cell growth disorders and therapeutic methods for cell growth disorders, including autoimmune diseases, cancer, and inflammatory diseases.

2. Related Art

Lectins are proteins that bind to specific carbohydrate structures and can thus recognize particular glycoconjugates. Barondes et al., *J. Biol. Chem.* 269(33):20807–20810 (1994). Galectins are members of a family of β-galactoside-binding lectins with related amino acid sequences (For review see, Barondes et al., *Cell* 76:597–598 (1994); Barondes et al., *J. Biol. Chem.* 269(33):20807–20810 (August 1994)). Galectin 1 (aka. L-14-1, L-14, RL-14.5, galaptin, MGBP, GBP, BHL, CHA, HBP, HPL, HLBP 14, rIML-1) is a homodimer with a subunit molecular mass of 14,500 which is abundant in smooth and skeletal muscle, and is present in many other cell types (Couraud et al., *J. Biol. Chem.* 264:1310–1316 (1989)). Galectin 2 was originally found in hepatoma and is a homodimer with a subunit molecular weight of 14,650 (Gitt et al, *J. Biol. Chem.* 267:10601–10606 (1992)). Galectin 3 (aka. Mac-2, EPB, CBP-35, CBP-30, and L-29) is abundant in activated macrophages and epithelial cells and is a monomer with an apparent molecular mass between 26,320 and 30,300 (Cherayil et al., *Proc. Natl. Acad. Sci. USA* 87: 7324–7326 (1990)). Galectin 4 has a molecularmass of 36,300 and contains two carbohydrate-binding domains within a single polypeptide chain (Oda et al., *J. Biol. Chem.* 268:5929–5939 (1993)). Galectins 5 and 6 are mentioned in Barondes et al., Cell 76:597–598 (1994). Human galectin 7 has a molecular mass of 15,073 and is found mainly in stratified squamous epithelium (Madsen et al., *J. Biol. Chem.* 270(11) :5823–5829 (1995)).

Animal lectins, in general, often function in modulating cell-cell and cell-matrix interactions. Galectin 1 has been shown to either promote or inhibit cell adhesion depending upon the cell type in which it is present. Galectin 1 inhibits cell-matrix interactions in skeletal muscle (Cooper et al., *J. Cell Biol.* 115:1437–1448 (1991)). In other cell types, galectin 1 promotes cell-matrix adhesion possibly by cross-linking cell surface and substrate glycoconjugates (Zhou et al., *Arch. Biochem. Biophys.* 300:6–17 (1993); Skrincosky et al., *Cancer Res.* 53:2667–2675 (1993)).

Galectin 1 also participates in regulating cell proliferation (Wells et al., Cell 64:91–97 (1991)) and some immune functions (Offner et al., *J. Neuroimmunol.* 28:177–184 (1990)). Galectin 1 has been shown to regulate the immune response by mediating apoptosis of T cells (Perillo et al., *Nature* 378:736–739 (1995)).

Galectin 3 promotes the growth of cells cultured under restrictive culture conditions (Yang et al., *Proc. Natl. Acad. Sci. USA* 93:6737–6742 (June 1996)). Galectin 3 expression in cells confers resistance to apoptosis which indicates that Galectin 3 could be a cell death suppressor which interferes in a common pathway of apoptosis. Id.

Accordingly, there is a need in the art for the identification of novel galectins which can serve as useful tools in the development of therapeutics and diagnostics for regulating immune response.

SUMMARY OF THE INVENTION

The present invention provides isolated nucleic acid molecules comprising a polynucleotide encoding the galectin 8, 9, 10, or 10SV polypeptide having the amino acid sequence is shown in FIGS. 1, 2A–2B, 3A–3B, and 4A–4B, respectively (SEQ ID NOs:2, 4, 6, and 8, respectively) or the amino acid sequence encoded by the cDNA clones deposited as ATCC Deposit Numbers 97732, 97733 and 97734 on Sep. 24, 1996.

The present invention also relates to recombinant vectors, which include the isolated nucleic acid molecules of the present invention, and to host cells containing the recombinant vectors, as well as to methods of making such vectors and host cells and for using them for production of galectin 8, 9, 10, or 10SV polypeptides or peptides by recombinant techniques.

The invention further provides an isolated galectin 8, 9, 10, or 10SV polypeptide having an amino acid sequence encoded by a polynucleotide described herein.

The present invention also provides a screening method for identifying compounds capable of enhancing or inhibiting a cellular response induced by galectin 8, 9, 10, or 10SV, which involves contacting cells which express galectin 8, 9, 10, or 10SV with the candidate compound, assaying a cellular response, and comparing the cellular response to a standard cellular response, the standard being assayed when contact is made in absence of the candidate compound; whereby, an increased cellular response over the standard indicates that the compound is an agonist and a decreased cellular response over the standard indicates that the compound is an antagonist.

In another aspect, a screening assay for agonists and antagonists is provided which involves determining the effect a candidate compound has on galectin 8, 9, 10, or 10SV binding to the β-galactosidase sugar. In particular, the method involves contacting the β-galactosidase sugar with a galectin 8, 9, 10, or 10SV polypeptide and a candidate compound and determining whether galectin 8, 9, 10, or 10SV binding to β-galactosidase sugar is increased or decreased due to the presence of the candidate compound.

The invention provides a diagnostic method useful during diagnosis disorder.

An additional aspect of the invention is related to a method for treating an individual in need of an increased level of galectin 8, 9, 10, or 10SV activity in the body comprising administering to such an individual a composition comprising a therapeutically effective amount of an isolated galectin 8, 9, 10, or 10SV polypeptide of the invention or an agonist thereof.

A still further aspect of the invention is related to a method for treating an individual in need of a decreased level of galectin 8, 9, 10, or 10SV activity in the body comprising, administering to such an individual a composition comprising a therapeutically effective amount of a galectin 8, 9, 10, or 10SV antagonist.

BRIEF DESCRIPTION OF THE FIGURES

FIG. 1 shows the nucleotide (SEQ ID NO:1) and deduced amino acid (SEQ ID NO:2) sequences of galectin 8. The protein has a deduced molecular weight of about 36 kDa.

FIGS. 2A–2B shows the nucleotide (SEQ ID NO:3) and deduced amino acid (SEQ ID NO:4) sequences of galectin 9. The protein has a deduced molecular weight of about 34.7 kDa.

FIGS. 3A–3B shows the nucleotide (SEQ ID NO:5) and deduced amino acid (SEQ ID NO:6) sequences of full length galectin 10. The protein has a deduced molecular weight of about 35.7 kDa.

FIGS. 4A–4B shows the nucleotide (SEQ ID NO:7) and deduced amino acid (SEQ ID NO:8) sequences of a galectin 10 splice variant (galectin 10SV). The protein has a deduced molecular weight of about 22.4 kDa.

FIGS. 5A–5E shows the regions of similarity between the amino acid sequences of the galectin 8, 9, and 10 proteins and human galectin 2 (SEQ ID NO:9), human galectin 3 (SEQ ID NO:10), rat galectin 4 (SEQ ID NO:11), rat galectin 5 (SEQ ID NO:12), human galectin 7 (SEQ ID NO:13), rat galectin 3 (SEQ ID NO:14), rat galectin 8 (SEQ ID NO:15), and human galectin 1 (SEQ ID NO:16).

FIG. 6 shows the regions of similarity between the amino acid sequences of the galectin 10SV protein and the rat RL30 protein (SEQ ID NO:17).

FIG. 7 shows a homology comparison between the galectin 10 and galectin 10SV proteins.

DETAILED DESCRIPTION

Figure 5A:
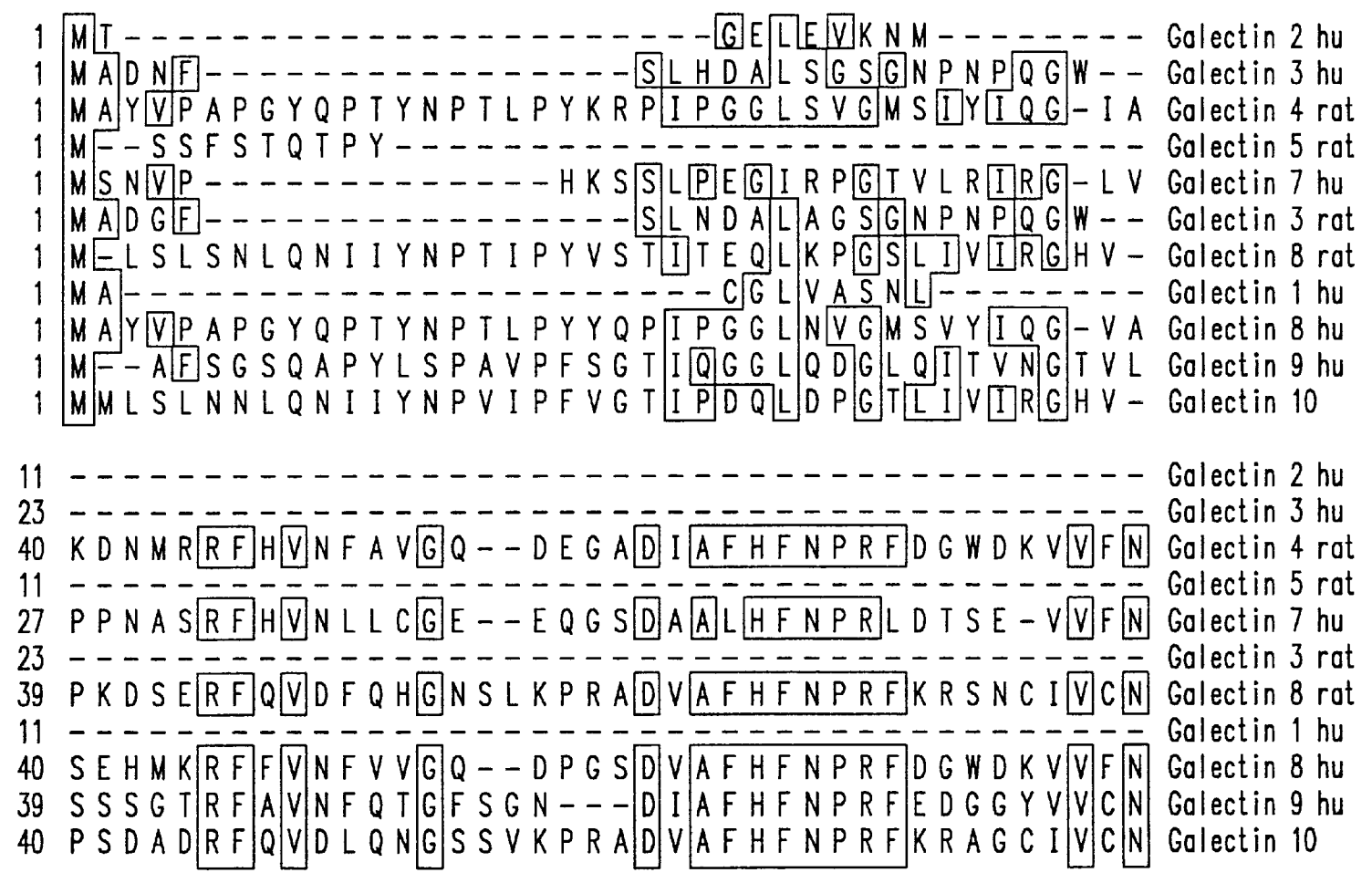
Figure 5B:
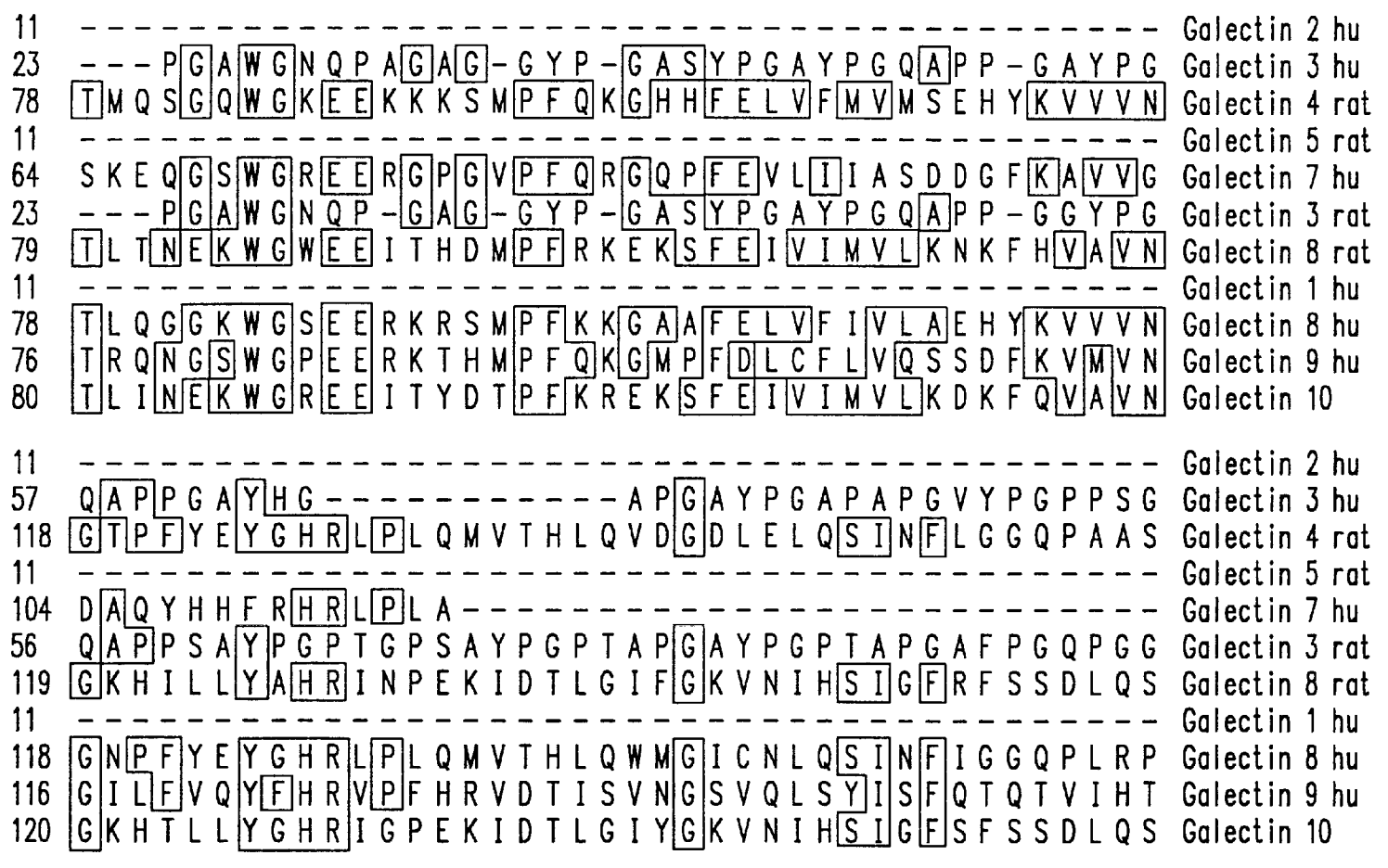
Figure 5C:
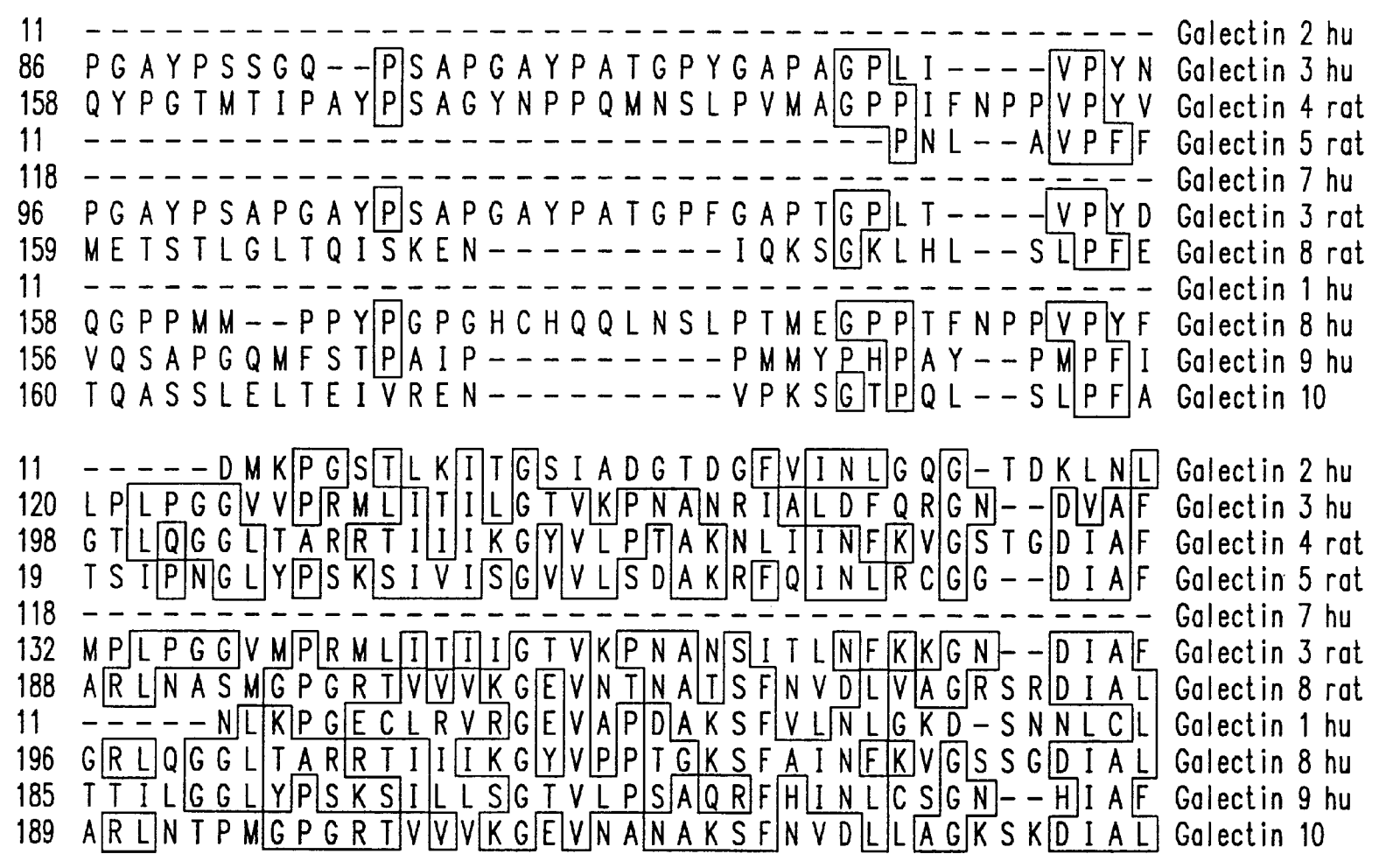
Figure 5D:
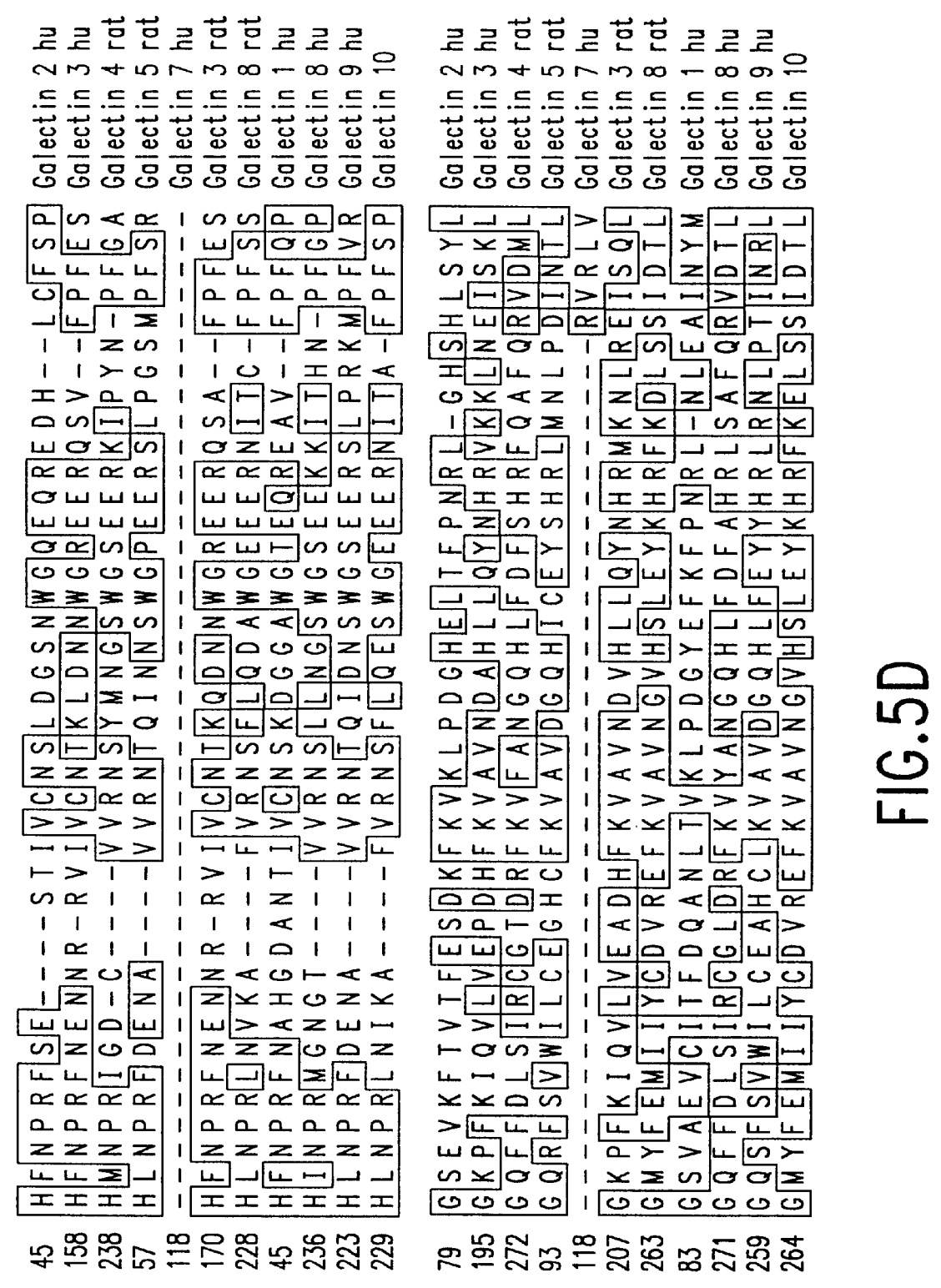
Figure 8:
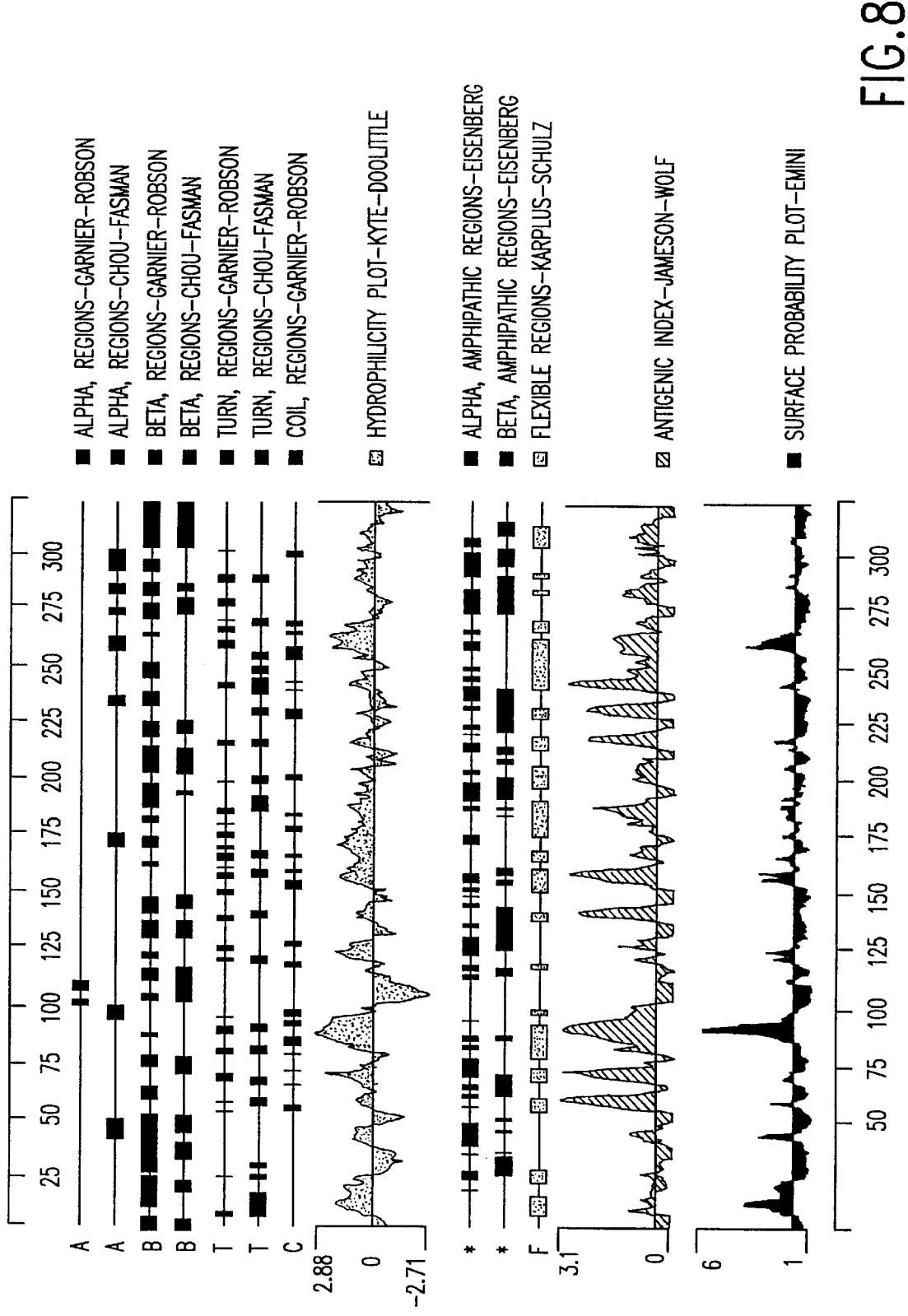
FIGS. 8, 9, 10, and 11 show an analysis of the galectin 8, 9, 10, and 10SV amino acid sequence, respectively. Alpha, beta, turn and coil regions; hydrophilicity and hydrophobicity; amphipathic regions; flexible regions; antigenic index and surface probability are shown. In the "Antigenic Index—Jameson-Wolf" graph, amino acid residues 55–101, 137–162, 180–193, 216–266 in FIG. 1 (SEQ ID NO:2), 62–102, 226–259, 197–308 in FIGS. 2A–2B (SEQ ID NO:4), 25–77, 84–105, 129–140, 156–183, 195–215, and 241–257 in FIGS. 3A–3B (SEQ ID NO:6), and 25–77, 84–105, 129–140, and 156–183 in FIGS. 4A–4B (SEQ ID NO:8) correspond to the shown highly antigenic regions of the galectin 8, 9, 10, or 10SV protein, respectively.
Figure 9:
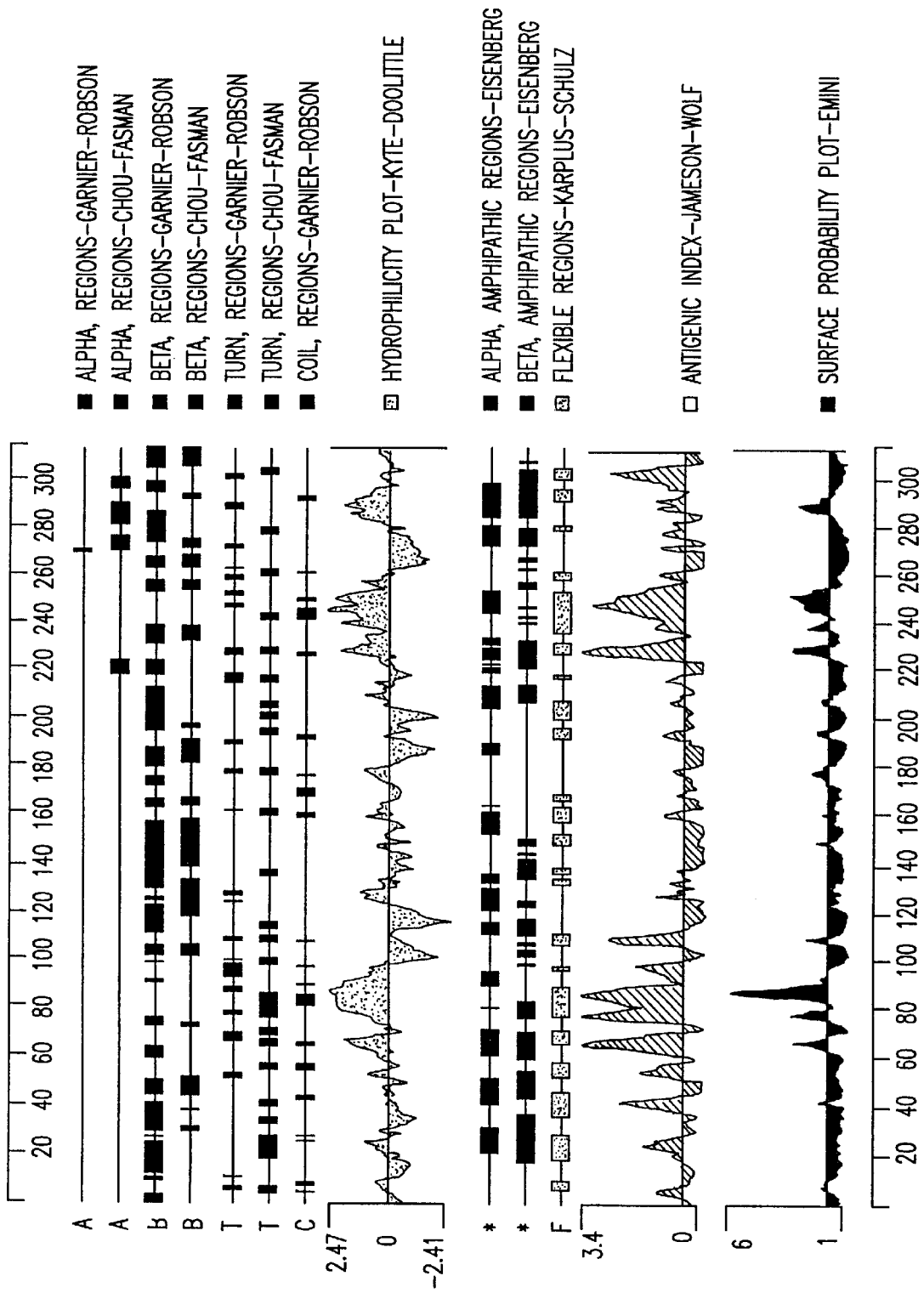
Figure 10:
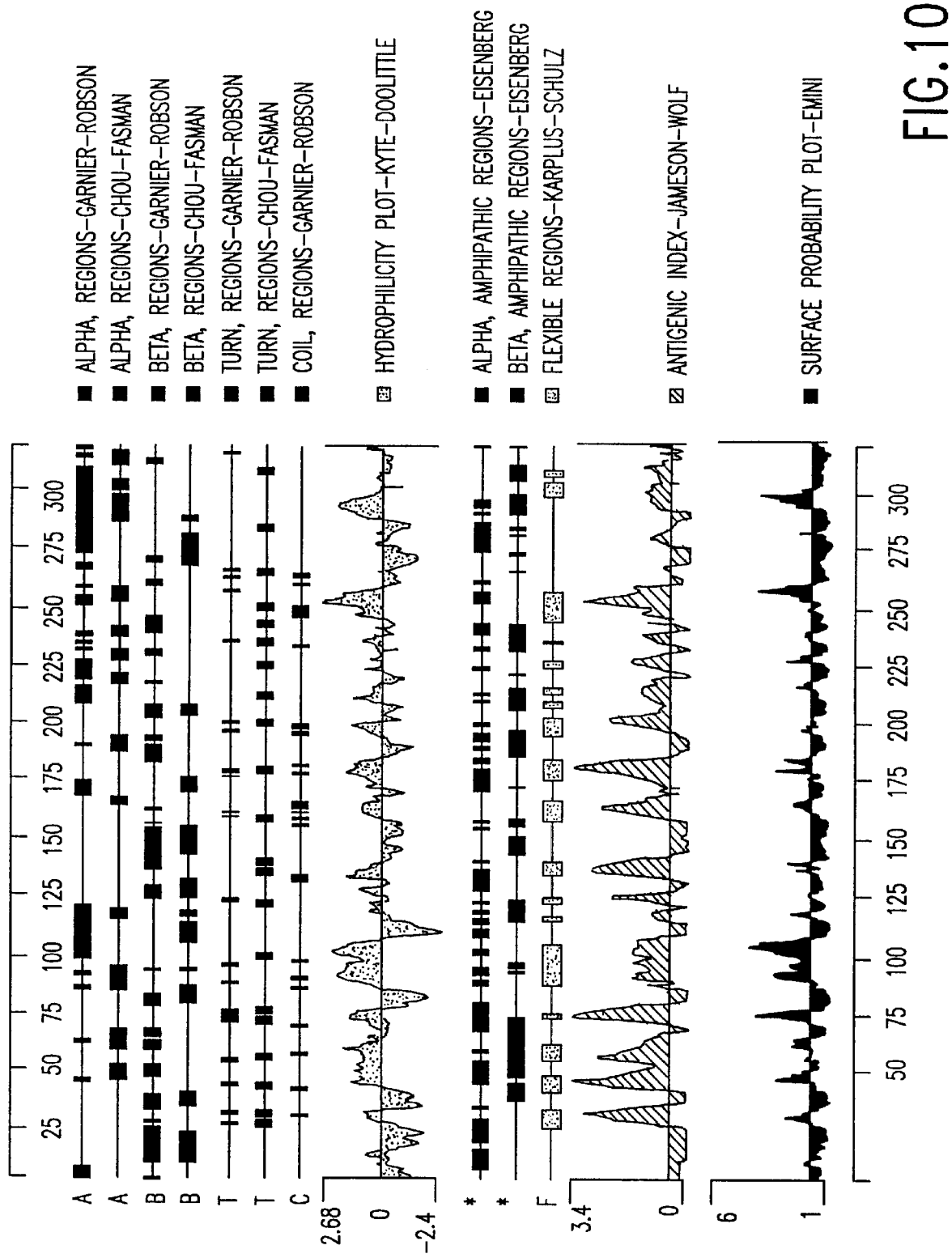
Figure 11:
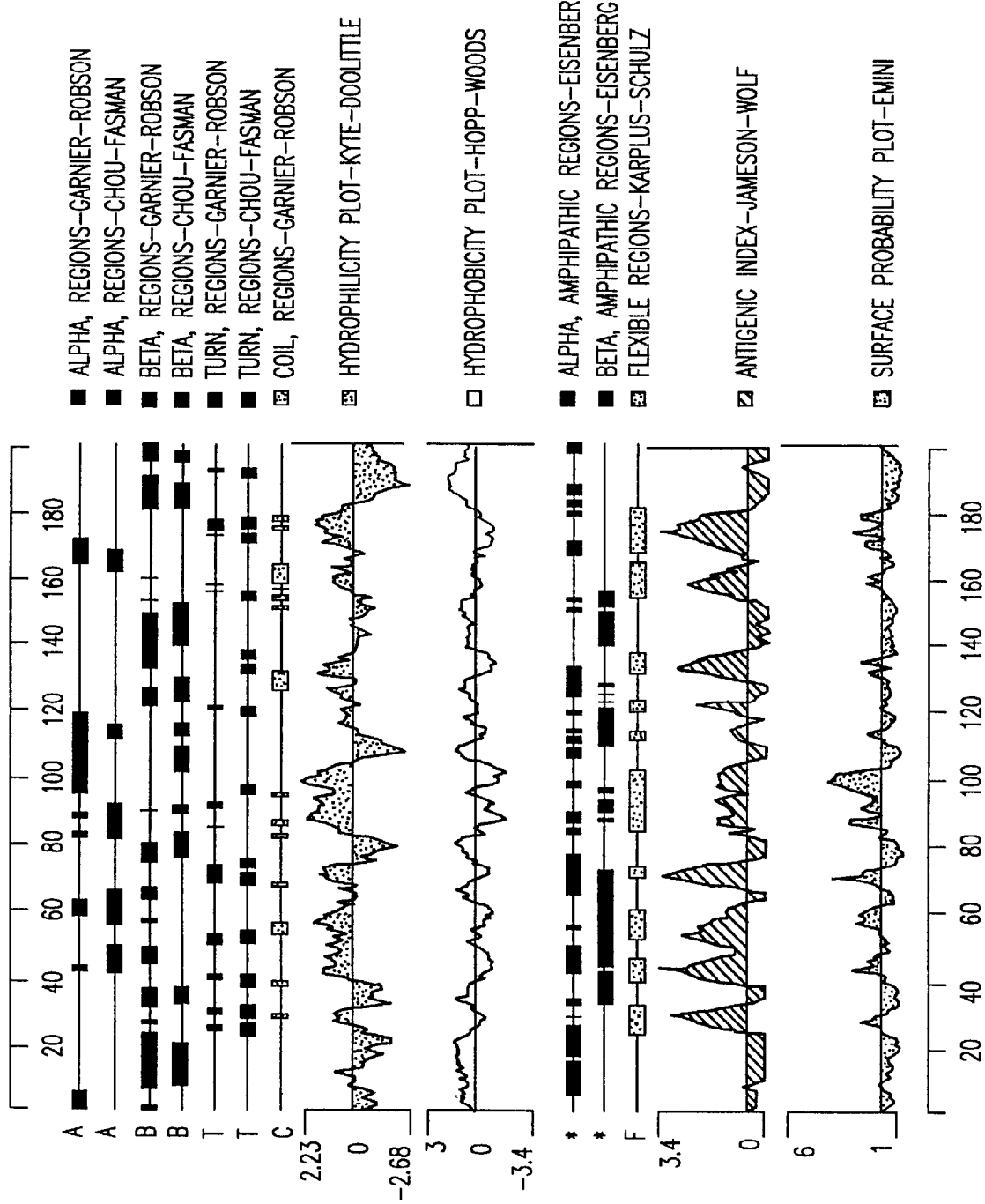

The present invention provides isolated nucleic acid molecules comprising a polynucleotide encoding a galectin 8, 9, 10, or 10SV polypeptide having the amino acid sequence shown in FIGS. 1, 2A–2B, 3A–3B, and 4A–4B, respectively (SEQ ID NOs:2, 4, 6, and 8, respectively), which was determined by sequencing a cloned cDNA. The galectin 8,9, 10, and 10SV proteins of the present invention share sequence homology with other galectins and the rat RL30 protein (FIGS. 5A–5E and 6) (SEQ ID NOs:9–17). The nucleotide sequences shown in FIGS. 1, 2A–2B, and 4A–4B (SEQ ID NO:1, 3, and 7, respectively) were obtained by sequencing the HSIAL77, HTPBR22, and HETAS87 clones, which were deposited on Sep. 24, 1996 at the American Type Culture Collection, 10801 University Blvd., Manassas, Va. 20110-2209, USA. and given accession numbers 97732, 97733 and 97734, respectively. The deposited clones are contained in the pbluescript SK(-) plasmid (Stratagene, LaJolla, Calif.).

The nucleotide sequence shown in FIGS. 3A–3B (SEQ ID NO:5), which encodes the full-length galectin 10 protein, was obtained by sequencing a clone cDNA obtained from a human endometrial tumor library.

Nucleic Acid Molecules

Unless otherwise indicated, all nucleotide sequences determined by sequencing a DNA molecule. herein were determined using an automated DNA sequencer (such as the Model 373 from Applied Biosystems, Inc.), and all amino acid sequences of polypeptides encoded by DNA molecules determined herein were predicted by translation of a DNA sequence determined as above. Therefore, as is known in the art for any DNA sequence determined by this automated approach, any nucleotide sequence determined herein may contain some errors. Nucleotide sequences determined by automation are typically at least about 90% identical, more typically at least about 95% to at least about 99.9% identical to the actual nucleotide sequence of the sequenced DNA molecule. The actual sequence can be more precisely determined by other approaches including manual DNA sequencing methods well known in the art. As is also known in the art, a single insertion or deletion in a determined nucleotide sequence compared to the actual sequence will cause a frame shift in translation of the nucleotide sequence such that the predicted amino acid sequence encoded by a determined nucleotide sequence will be completely different from the amino acid sequence actually encoded by the sequenced DNA molecule, beginning at the point of such an insertion or deletion.

Using the information provided herein, such as the nucleotide sequences in FIGS. 1, 2A–2B; 3A–3B, and 4A–4B a nucleic acid molecule of the present invention encoding a galectin 8, 9, 10, or 10SV, respectively, polypeptide may be obtained using standard cloning and screening procedures, such as those for cloning cDNAs using mRNA as starting material. Illustrative of the invention, the nucleic acid molecules described in FIGS. 1, 2A–2B, 3A–3B, and 4A–4B (SEQ ID NO:1, 3, 5, and 7, respectively) were discovered in cDNA libraries derived from human adult small intestine, human pancreatic tumor, human endometrial tumor and human endometrial tumor, respectively. These genes were also identified in cDNA libraries from the following tissues pancreas, colon, small intestine, brain, bone marrow, kidney, lung, spleen, and testes tissue. Galectin 8 (SEQ ID NO: 1) appears to be mainly expressed in cells of the human colon and small intestine.

The determined nucleotide sequences of the galectin 8, 9, 10, and 10SV cDNAs of FIGS. 1, 2A–2B, 3A–3B, and 4A–4B, respectively (SEQ ID NOs: 1, 3, 5, and 7) contain open reading frames encoding proteins of 323, 311, 317, and 200 amino acid residues, with an initiation codon at positions 52–54, 16–18, 118–120, and 118–120 of the nucleotide sequences in FIGS. 1, 2A–2B, 3A–3B, and 4A–4B, respectively (SEQ ID NOs:1, 3, 5, and 7), and a deduced molecular weight of about 36, 34.7, 35.7, and 22.4 kDa, respectively. The galectin 8, 9, 10 and 10SV proteins shown in FIGS. 1, 2A–2B, 3A–3B, and 4A–4B respectively (SEQ ID NOs:2, 4, 6, and 8) share homology with other galectins (See, e.g., FIGS. 5A–5E.

As one of ordinary skill would appreciate, due to the possibilities of sequencing errors discussed above, as well as the variability of processing sites for different known proteins, the predicted galectin 8 and 9 polypeptides encoded by the deposited cDNAs comprise about 323 and 311 amino acids, but may be anywhere in the range of 300–333 amino acids. Similarly, the predicted galectin 10 polypeptide comprises about 317 amino acids, but may be anywhere in the range of 305–329 amino acids. Further, the predicted galectin 10SV polypeptide encoded by the deposited cDNA comprises about 200 amino acids, but may be anywhere in the range of 190–210 amino acids.

Galectin 10SV is believed to be a splice variant of galectin 10. As used herein the phrase "splice variant" refers to cDNA molecules produced from RNA molecules initially transcribed from the same genomic DNA sequence but which have undergone alternative RNA splicing. Alternative RNA splicing occurs when a primary RNA transcript undergoes splicing, generally for the removal of introns, which results in the production of more than one mRNA molecule each of which may encode different amino acid sequences. The term "splice variant" also refers to the proteins encoded by the above cDNA molecules.

As indicated, nucleic acid molecules of the present invention may be in the form of RNA, such as mRNA, or in the form of DNA, including, for instance, cDNA and genomic DNA obtained by cloning or produced synthetically. The DNA may be double-stranded or single-stranded. Single-stranded DNA or RNA may be the coding strand, also known as the sense strand, or it may be the non-coding strand, also referred to as the anti-sense strand.

By "isolated" nucleic acid molecule(s) is intended a nucleic acid molecule, DNA or RNA, which has been removed from its native environment For example, recombinant DNA molecules contained in a vector are considered isolated for the purposes of the present invention. Further examples of isolated DNA molecules include recombinant DNA molecules maintained in heterologous host cells or purified (partially or substantially) DNA molecules in solution. Isolated RNA molecules include in vivo or in vitro RNA transcripts of the DNA molecules of the present invention. Isolated nucleic acid molecules according to the present invention further include such molecules produced synthetically.

Isolated nucleic acid molecules of the present invention include DNA molecules comprising an open reading frame (ORF) shown in FIGS. 1, 2A–2B, 3A–3B, and 4A–4B, respectively (SEQ ID NOs:1, 3, 5, and 7); and DNA molecules which comprise a sequence substantially different from those described above but which, due to the degeneracy of the genetic code, still encode the galectin 8, 9, 10, or 10SV protein. Of course, the genetic code is well known in the art. Thus, it would be routine for one skilled in the art to generate such degenerate variants.

In addition, the invention provides nucleic acid molecules having nucleotide sequences related to extensive portions of SEQ ID NO:1 which have been determined from the following related cDNA clones: HSIAL77R (SEQ ID NO:18), HGBDK55R (SEQ ID NO:19), HCNAH29R (SEQ ID NO:20), HKCAA85R (SEQ ID NO:21), HCNAI55R (SEQ ID NO:22), HCNAI87R (SEQ ID NO:23), HCNAS74R (SEQ ID NO:24) and HCNAF43R (SEQ ID NO:25).

In addition, the invention provides nucleic acid molecules having nucleotide sequences related to extensive portions of SEQ ID NO:3 which have been determined from the following related cDNA clones: HMSCPl IR (SEQ ID NO:26), HMSEU32R (SEQ ID NO:27), HTPAO71R (SEQ ID NO:28), HJAAV54R (SEQ ID NO:29), HMSEU43R (SEQ ID NO:30), HILBP03R (SEQ ID NO:31), HTPCG81R (SEQ ID NO:32), HTBAA21R (SEQ ID NO:33), and HFXBU26R (SEQ ID NO:34).

In addition, the invention provides nucleic acid molecules having nucleotide sequences related to extensive portions of SEQ ID NO:5 which have been determined from the following related cDNA clones: HTNBX92R (SEQ ID NO:35), HLTAZ64RB (SEQ ID NO:36), HJBAI38R (SEQ ID NO:37), HETAS87R (SEQ ID NO:38), and HETAR45R (SEQ ID NO:39).

In addition, the invention provides nucleic acid molecules having nucleotide sequences related to extensive portions of SEQ ID NO:7 which have been determined from the following related cDNA clones: HTNBX92R (SEQ ID NO:35), HLTAZ64RB (SEQ ID NO:36), HBNAF37R (SEQ ID NO:40), and HETAS87R (SEQ ID NO:38).

In another aspect, the invention provides isolated nucleic acid molecules encoding the galectin 8, 9, 10 or 10SV polypeptide having an amino acid sequence encoded by the cDNA clone contained in the plasmid deposited as ATCC Deposit Nos. 97732, 97733 and 97734, respectively, on Sep. 24, 1996. In a further embodiment, nucleic acid molecules are provided encoding the full-length galectin 8, 9, 10, or 10SV polypeptide lacking the N-terminal methionine. The invention further provides an isolated nucleic acid molecule having the nucleotide sequence shown in FIGS. 1, 2A–2B, 3A–3B, or 4A–4B (SEQ ID NOs:1, 3, 5, or 7) or the nucleotide sequence of the galectin 8, 9, or 10SV cDNA contained in the above-described deposited clones, or a nucleic acid molecule having a sequence complementary to one of the above sequences. Such isolated molecules, particularly DNA molecules, are useful as probes for gene mapping, by in situ hybridization with chromosomes, and for detecting expression of the galectin 8, 9, 10, or 10SV gene in human tissue, for instance, by Northern blot analysis.

The present invention is further directed to fragments of the isolated nucleic acid molecules described herein. By a fragment of an isolated nucleic acid molecule having the nucleotide sequence of the deposited cDNA or the nucleotide sequence shown in FIGS. 1, 2A–2B, 3A–3B, or 4A–4B (SEQ ID NO:1, 3, 5, or 7) is intended fragments at least about 15 nt, and more preferably at least about 20 nt, still more preferably at least about 30 nt, and even more preferably, at least about 40 nt in length which are useful as diagnostic probes and primers as discussed herein. Of course larger DNA fragments 50, 100, 150, 200, 250, 300, 350, 400, 450, 500, 550, 600, 650, 700, 750, 800, 850, 900, 100, 1050, 1100, or 1115 nt in length of the sequence shown in SEQ ID NO:1 are also useful according to the present invention as are fragments corresponding to most, if not all, of the nucleotide sequence of the cDNA clone contained in the plasmid deposited as ATCC Deposit No. 97732 or as shown in SEQ ID NO:1. Similarly, larger DNA fragments 50, 100, 150, 200, 250, 300, 350, 400, 450, 500, 550, 600, 650, 700, 750, 800, 850, 900, 100, 1050, 1100, 1150, 1200, 1250, 1300, 1350, 1400, 1450, 1500, or 1525 nt in length of the sequence shown in SEQ ID NO:3 are also useful according to the present invention as are fragments corresponding to most, if not all, of the nucleotide sequence of the cDNA clone contained in the plasmid deposited as ATCC Deposit No. 97733 or as shown in SEQ ID NO:3. Similarly, larger DNA fragments 50, 100, 150, 200, 250, 300, 350, 400, 450, 500, 550, 600, 650, 700, 750, 800, 850, 900, 100, 1050, 1100, 1150, 1200, 1250, 1300, 1350, 1400, 1450, or 1464 nt in length of the sequence shown in SEQ ID NO:5 are also useful according to the present invention as are fragments corresponding to most, if not all, of the nucleotide sequence of the CDNA molecule as shown in SEQ ID NO:5. Further, larger DNA fragments 50, 100, 150, 200, 250, 300, 350, 400, 450, 500, 550, 600, 650, 700, 750, 800, 850, 900, 100, 1050, 1100, 1150, 1200, 1250, 1300, 1350, 1400, 1450, 1500, 1550, 1600, 1650, 1700, 1750, 1800, 1850, 1900, and 1908 nt in length of the sequence shown in SEQ ID NO:7 are also useful according to the present invention as are fragments corresponding to most, if not all, of the nucleotide sequence of the cDNA clone contained in the plasmid deposited as ATCC Deposit No. 97734 or as shown in SEQ ID NO:7. By a fragment at least 20 nt in length, for example, is intended fragments which include 20 or more contiguous bases from the nucleotide sequence of the deposited cDNA or the nucleotide sequence as shown in SEQ ID NOs:1, 3, 5, or 7.

Preferred nucleic acid fragments of the present invention include nucleic acid molecules encoding epitope-bearing portions of the galectin 8, 9, 10, or 10SV protein. In particular, such nucleic acid fragments of the present invention include nucleic acid molecules encoding: a polypeptide comprising amino acid residues from about 55–101, 137–162, 180–193, 216–266 in FIG. 1 (SEQ ID NO:2), 62–102, 226–259, 197–308 in FIGS. 2A–2B (SEQ ID NO:4), 25–77, 84–105, 129–140, 156–183, 195–215, and 241–257 in FIGS. 3A–3B (SEQ ID NO:6), and 25–77, 84–105, 129–140, and 156–183 in FIGS. 4A–4B (SEQ ID NO:8). The inventors have determined that the above polypeptide fragments are antigenic regions of the galectin 8, 9, 10, and 10SV proteins. Methods for determining other such epitope-bearing portions of the galectin 8, 9, 10, and 10SV proteins are described in detail below.

In another aspect, the invention provides an isolated nucleic acid molecule comprising a polynucleotide which hybridizes under stringent hybridization conditions to a portion of the polynucleotide in a nucleic acid molecule of the invention described above, for instance, a cDNA clone contained in ATCC Deposit Nos. 97732, 97733 and 97734. By "stringent hybridization conditions" is intended overnight incubation at 42° C. in a solution comprising: 50% formamide, 5×SSC (750 mM NaCl 75 mM trisodium citrate), 50 mM sodium phosphate (pH 7.6), 5×Denhardt's solution, 10% dextran sulfate, and 20 µg/ml denatured, sheared salmon sperm DNA, followed by washing the filters in 0.1×SSC at about 65° C.

By a polynucleotide which hybridizes to a "portion" of a polynucleotide is intended a polynucleotide (either DNA or RNA) hybridizing to at least about 15 nucleotides (nt), and more preferably at least about 20 nt, still more preferably at least about 30 nt, and even more preferably about 30–70 nt of the reference polynucleotide. These are useful as diagnostic probes and primers as discussed above and in more detail below.

By a portion of a polynucleotide of "at least 20 nt in length," for example, is intended 20 or more contiguous nucleotides from the nucleotide sequence of the reference polynucleotide (e.g, the deposited cDNA or the nucleotide sequence as shown in FIGS. 1, 2A–2B, 3A–3B, or 4A–4B (SEQ ID NOs:1, 3, 5, or 7)). Of course, a polynucleotide which hybridizes only to a poly A sequence (such as the 3' terminal poly(A) tract of the galectin 8, 9, 10, or 10SV cDNA shown in FIGS. 1, 2A–2B, 3A–3B, or 4A–4B, respectively (SEQ ID NOs:1, 3, 5, or 7)), or to a complementary stretch of T (or U) resides, would not be included in a polynucleotide of the invention used to hybridize to a portion of a nucleic acid of the invention, since such a polynucleotide would hybridize to any nucleic acid molecule containing a poly (A) stretch or the complement thereof (e.g., practically any double-stranded cDNA clone).

As indicated, nucleic acid molecules of the present invention which encode a galectin 8, 9, 10, or 10SV polypeptide may include, but are not limited to those encoding the amino acid sequence of the polypeptide, by itself; the coding sequence for the polypeptide and additional sequences, such as those encoding an amino acid leader or secretory sequence, such as a pre-, or pro- or prepro-protein sequence; the coding sequence of the polypeptide, with or without the aforementioned additional coding sequences, together with additional, non-coding sequences, including for example, but not limited to introns and non-coding 5' and 3' sequences, such as the transcribed, non-translated sequences that play a role in transcription, mRNA processing, including splicing and polyadenylation signals, for example— ribosome binding and stability of MRNA; an additional coding sequence which codes for additional amino acids, such as those which provide additional functionalities. Thus, the sequence encoding the polypeptide may be fused to a marker sequence, such as a sequence encoding a peptide which facilitates purification of the fused polypeptide. In certain preferred embodiments of this aspect of the invention, the marker amino acid sequence is a hexa-histidine peptide, such as the tag provided in a pQE vector (Qiagen, Inc.), among others, many of which are commercially available. As described in Gentz et al., *Proc. Natl. Acad. Sci. USA* 86:821–824 (1989), for instance, hexa-histidine provides for convenient purification of the fusion protein. The "HA" tag is another peptide useful for purification which corresponds to an epitope derived from the influenza hemagglutinin protein, which has been described by Wilson et al., *Cell* 37:767–778 (1984). As discussed below, other such fusion proteins include the galectin 8, 9, 10, or 10SV fused to Fc at the N- or C-terminus.

The present invention further relates to variants of the nucleic acid molecules of the present invention, which encode portions, analogs or derivatives of the galectin 8, 9, 10, or 10SV protein. Variants may occur naturally, such as a natural allelic variant. By an "allelic variant" is intended one of several alternate forms of a gene occupying a given locus on a chromosome of an organism. *Genes II*, Lewin, B., ed., John Wiley & Sons, New York (1985). Non-naturally occurring variants may be produced using art-known mutagenesis techniques.

Such variants include those produced by nucleotide substitutions, deletions or additions which may involve one or more nucleotides. The variants may be altered in coding regions, non-coding regions, or both. Alterations in the coding regions may produce conservative or non-conservative amino acid substitutions, deletions or additions. Especially preferred among these are silent substitutions, additions and deletions, which do not alter the properties and activities of the galectin 8, 9, 10, or 10SV protein or portions thereof. Also especially preferred in this regard are conservative substitutions.

Further embodiments of the invention include isolated nucleic acid molecules comprising a polynucleotide having a nucleotide sequence at least 95% identical, and more preferably at least 96%, 97%, 98% or 99% identical to (a) a nucleotide sequence encoding the galectin 8, 9, 10, or 10SV polypeptide having the amino acid sequence in FIGS. 1, 2A–2B, 3A–3B, or 4A–4B (SEQ ID NOs:1, 3, 5, or 7); (b) a nucleotide sequence encoding the polypeptide having the amino acid sequence in FIGS. 1, 2A–2B, 3A–3B, or 4A–4B (SEQ ID NOs: 1, 3, 5, or 7), but lacking the N-terminal methionine; (c) a nucleotide sequence encoding the amino acid sequence encoded by the cDNA clone contained in ATCC Deposit Nos. 97732, 97733 or 97734 on Sep. 24, 1996; or (d) a nucleotide sequence complementary to any of the nucleotide sequences in (a), (b), or (c).

By a polynucleotide having a nucleotide sequence at least, for example, 95% "identical" to a reference nucleotide sequence encoding a galectin 8, 9, 10, or 10SV polypeptide is intended that the nucleotide sequence of the polynucleotide is identical to the reference sequence except that the polynucleotide sequence may include up to five point mutations per each 100 nucleotides of the reference nucleotide sequence encoding the galectin 8, 9, 10, or 10SV polypeptide. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence.

As a practical matter, whether any particular nucleic acid molecule is at least 95%, 96%, 97%, 98% or 99% identical to, for instance, the nucleotide sequence shown in FIGS. 1, 2A–2B, 3A–3B, or 4A–4B (SEQ ID NOs:1, 3, 5, or 7) or to the nucleotides sequence of the deposited cDNA clone can be determined conventionally using known computer programs such as the Bestfit program (Wisconsin Sequence Analysis Package, Version 8 for Unix, Genetics Computer Group, University Research Park, 575 Science Drive, Madison, Wis. 53711. Bestfit uses the local homology algorithm of Smith and Waterman, *Advances in Applied Mathematics* 2:482–489 (1981)), to find the best segment of homology between two sequences. When using Bestfit or any other sequence alignment program to determine whether a particular sequence is, for instance, 95% identical to a reference sequence according to the present invention, the parameters are set, of course, such that the percentage of identity is calculated over the full length of the reference nucleotide sequence and that gaps in homology of up to 5% of the total number of nucleotides in the reference sequence are allowed.

The present application is directed to nucleic acid molecules at least 90% 95%, 96%, 97%, 98% or 99% identical to the nucleic acid sequence shown in FIGS. 1, 2A–2B, 3A–3B, or 4A–4B (SEQ ID NOs:1, 3, 5, or 7) or to the nucleic acid sequence of one of the deposited cDNAs, irrespective of whether they encode a polypeptide having galectin 8, 9, 10, or 10SV activity. This is because even where a particular nucleic acid molecule does not encode a polypeptide having galectin 8, 9, 10, or 10SV activity, one of skill in the art would still know how to use the nucleic acid molecule, for instance, as a hybridization probe or a polymerase chain reaction (PCR) primer. Uses of the nucleic acid molecules of the present invention that do not encode a polypeptide having galectin 8, 9, 10, or 10SV activity include, inter alia, (1) isolating the galectin 8, 9, 10, or 10SV gene or allelic variants thereof in a cDNA library; (2) in situ hybridization (e.g., "FISH") to metaphase chromosomal spreads to provide precise chromosomal location of the galectin 8, 9, 10, or 10SV gene, as described in Verma et al., *Human Chromosomes: A Manual of Basic Techniques*, Pergamon Press, New York (1988); and (3) Northern Blot analysis for detecting galectin 8, 9, 10, or 10SV MRNA expression in specific tissues.

Preferred, however, are nucleic acid molecules having sequences at least 95%, 96%, 97%, 98% or 99% identical to the nucleic acid sequence shown in FIGS. 1, 2A–2B, 3A–3B, or 4A–4B (SEQ ID NOs:1, 3, 5, or 7) or to the nucleic acid sequence of one of the deposited cDNAs which do, in fact, encode a polypeptide having galectin 8, 9, 10, or 10SV protein activity. By "a polypeptide having galectin 8, 9, 10, or 10SV activity" is intended polypeptides exhibiting activity similar, but not necessarily identical, to an activity of the galectin 8, 9, 10, or 10SV protein of the invention, as measured in a particular biological assay. For example, galectin 8, 9, 10, or 10SV protein activity can be measured using a lactose binding assay.

Lactose binding activity of the expressed galectin 8, 9, 10, or 10SV is assayed by immunodetection of in situ binding activity to asialofetuin (Sigma) immobilized on nitrocellulose (Amersham) (Madsen et al., *J. Biol. Chem.* 270(11) :5823–5829 (1995)). Thirty $\mu$g of asialofetuin dissolved in 3 $\mu$l of water is spotted on a 1-cm$^2$ strip of nitrocellulose. The nitrocellulose pieces are then placed in a 24-well tissue culture plate and incubated overnight in buffer B (58 mM $Na_2HPO_4$, 18 mM $KH_2PO_4$, 75 mM NaCl, 2 mM EDTA, and 3% BSA, pH7.2) with constant agitation at 22° C. Following incubation, the blocking medium is aspirated and the nitrocellulose pieces are washed three times in buffer A (58 mM $Na_2HPO_4$, 18 mM $KH_2PO_4$, 75 mM NaCl, 2 mM EDTA, 4 mM $\beta$-mercaptoethanol and 0.2% BSA, pH7.2). Cell extracts (preferably, COS cells) are prepared containing 1% BSA and either with or without 150 mM lactose (105 $\mu$l of primary extract, 15 $\mu$l of 10% BSA in buffer A and either 30 $\mu$l of 0.75 M lactose in buffer A or 30 $\mu$l of buffer A). The immobilized asialofetuin is incubated with the extracts for 2 h and washed 5 times in buffer A. The nitrocellulose pieces are then fixed in 2% formalin in PBS (58 mM $Na_2HPO_4$, 18 mM $KH_2PO_4$, 75 mM NaCl, 2 mM EDTA pH7.2) for 1 hour to prevent loss of bound galectin. Following extensive washing in PBS the pieces were incubated with rabbit anti-galectin 8, 9, 10, or 10SV polyclonal serum diluted 1:100 in PBS for 2 h at 22° C. The pieces are then washed in PBS and incubated with peroxidase-labeled goat anti-rabbit antibodies (DAKO). Following incubation for 2 h at 22° C., the pieces are washed in PBS and the substrate is added. Nitrocellulose pieces are incubated until the color develops and the reaction is stopped by washing in distilled water.

Of course, due to the degeneracy of the genetic code, one of ordinary skill in the art will immediately recognize that a large number of the nucleic acid molecules having a sequence at least 95%, 96%, 97%, 98%, or 99% identical to the nucleic acid sequence of the deposited cDNA or the nucleic acid sequence shown in FIGS. 1, 2A–2B, 3A–3B, or 4A–4B (SEQ ID NOs:1, 3, 5, or 7, respectively) will encode "a polypeptide having galectin 8, 9, 10, or 10SV protein activity." In fact, since degenerate variants of these nucleotide sequences all encode the same polypeptide, this will be clear to the skilled artisan even without performing the above described comparison assay. It will be further recognized in the art that, for such nucleic acid molecules that are not degenerate variants, a reasonable number will also encode a polypeptide having galectin 8, 9, 10, or 10SV protein activity. This is because the skilled artisan is fully aware of amino acid substitutions that are either less likely or not likely to significantly effect protein function (e.g., replacing one aliphatic amino acid with a second aliphatic amino acid).

For example, guidance concerning how to make phenotypically silent amino acid substitutions is provided in Bowie, J. U. et al., "Deciphering the Message in Protein Sequences: Tolerance to Amino Acid Substitutions," *Science* 247:1306–1310 (1990), wherein the authors indicate that proteins are surprisingly tolerant of amino acid substitutions.

Vectors and Host Cells

The present invention also relates to vectors which include the isolated DNA molecules of the present invention, host cells which are genetically engineered with the recombinant vectors, and the production of galectin 8, 9, 10, to or 10SV polypeptides or fragments thereof by recombinant techniques.

The polynucleotides may be joined to a vector containing a selectable marker for propagation in a host. Generally, a plasmid vector is introduced in a precipitate, such as a calcium phosphate precipitate, or in a complex with a charged lipid. If the vector is a virus, it may be packaged in vitro using an appropriate packaging cell line and then transduced into host cells.

The DNA insert should be operatively linked to an appropriate promoter, such as the phage lambda PL promoter, the E. coli lac, trp and tac promoters, the SV40 early and late promoters and promoters of retroviral LTRs, to name a few. Other suitable promoters will be known to the skilled artisan. The expression constructs will further contain sites for transcription initiation, termination and, in the transcribed region, a ribosome binding site for translation. The coding portion of the transcripts expressed by the constructs will preferably include a translation initiating at the beginning and a termination codon (UAA, UGA or UAG) appropriately positioned at the end of the polypeptide to be translated.

As indicated, the expression vectors will preferably include at least one selectable marker. Such markers include dihydrofolate reductase or neomycin resistance for eukaryotic cell culture and tetracycline or ampicillin resistance genes for culturing in E. coli and other bacteria. Representative examples of appropriate hosts include, but are not limited to, bacterial cells, such as E. coli, Streptomyces and Salmonella typhimurium cells; fungal cells, such as yeast cells; insect cells such as Drosophila S2 and Spodoptera Sf9 cells; animal cells such as CHO, COS and Bowes melanoma cells; and plant cells. Appropriate culture mediums and conditions for the above-described. host cells are known in the art.

Among vectors preferred for use in bacteria include pQE70, pQE60 and pQE-9, available from Qiagen; pBS vectors, Phagescript vectors, Bluescript vectors, pNH8A, pNH16a, pNH18A, pNH46A, available from Stratagene; and ptrc99a, pKK223-3, pKK233-3, pDR540, pRIT5 available from Pharmacia. Among preferred eukaryotic vectors are pWLNEO, pSV2CAT, pOG44, pXT1 and pSG available from Stratagene; and pSVK3, pBPV, pMSG and pSVL available from Pharmacia. Other suitable vectors will be readily apparent to the skilled artisan.

Introduction of the construct into the host cell can be effected by calcium phosphate transfection, DEAE-dextran mediated transfection, cationic lipid-mediated transfection, electroporation, transduction, infection or other methods. Such methods are described in many standard laboratory manuals, such as Davis et al., *Basic Methods In Molecular Biology* (1986).

The polypeptide may be expressed in a modified form, such as a fusion protein, and may include not only secretion signals, but also additional heterologous functional regions. For instance, a region of additional amino acids, particularly charged amino acids, may be added to the N-terminus of the polypeptide to improve stability and persistence in the host cell, during purification, or during subsequent handling and storage. Also, peptide moieties may be added to the polypeptide to facilitate purification. Such regions may be removed prior to final preparation of the polypeptide. The addition of peptide moieties to polypeptides to engender secretion or excretion, to improve stability and to facilitate purification, among others, are familiar and routine techniques in the art.

A preferred fusion protein comprises a heterologous region from immunoglobulin that is useful to solubilize proteins. For example, EP-A-O 464 533 (Canadian counterpart 2045869) discloses fusion proteins comprising various portions of constant region of immunoglobin molecules together with another human protein or part thereof. In many cases, the Fc part in a fusion protein is thoroughly advantageous for use in therapy and diagnosis and thus results, for example, in improved pharmacokinetic properties (EP-A 0232 262). On the other hand, for some uses it would be desirable to be able to delete the Fc part after the fusion protein has been expressed, detected and purified in the advantageous manner described. This is the case when Fc portion proves to be a hindrance to use in therapy and diagnosis, for example when the fusion protein is to be used as antigen for immunizations. In drug discovery, for example, human proteins, such as, hIL5-receptor has been fused with Fc portions for the purpose of high-throughput screening assays to identify antagonists of hIL-5. See, D. Bennett et al., *Journal of Molecular Recognition*, Vol. 8 52–58 (1995) and K. Johanson et al., *The Journal of Biological Chemistry*, Vol. 270, No. 16, pp 9459–9471 (1995).

The galectin 8, 9, 10, or 10SV protein can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography ("HPLC") is employed for purification. Polypeptides of the present invention include naturally purified products, products of chemical synthetic procedures, and products produced by recombinant techniques from a prokaryotic or eukaryotic host, including, for example, bacterial, yeast, higher plant, insect and mammalian cells. Depending upon the host employed in a recombinant production procedure, the polypeptides of the present invention may be glycosylated or may be non-glycosylated. In addition, polypeptides of the invention may also include an initial modified methionine residue, in some cases as a result of host-mediated processes.

Galectin 8, 9, 10 and 10SV Polypeptides and Fragments

The invention further provides an isolated galectin 8, 9, 10, or 10SV polypeptide having (1) the amino acid sequence encoded by one of the deposited cDNAs, (2) the amino acid sequence in FIGS. 1, 2A–2B, 3A–3B, or 4A–4B (SEQ ID NOs:2, 4, 6, or 8, respectively), or (3) the amino acid sequence of a peptide or It will be recognized in the art that some amino acid sequences of the galectin 8, 9, 10, or 10SV polypeptide can be varied without significant effect of the structure or function of the protein. If such differences in sequence are ID contemplated, it should be remembered that there will be critical areas on the protein which determine activity.

Thus, the invention further includes variations of the galectin 8, 9, 10, or 10SV polypeptide which show substantial galectin 8, 9, 10, or 10SV polypeptide activity or which include regions of galectin 8, 9, 10, or 10SV protein such as the protein portions discussed below. Such mutants include deletions, insertions, inversions, repeats, and type substitutions. As indicated above, guidance concerning which amino acid changes are likely to be phenotypically silent can be found in Bowie, J. U., et al., "Deciphering the Message in Protein Sequences: Tolerance to Amino Acid Substitutions," *Science* 247:1306–1310 (1990).

Thus, the fragment, derivative or analog of the polypeptide of SEQ ID NOs:2, 4, 6, or 8, or that encoded by one of the deposited cDNAs, may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the mature polypeptide, such as an IgG Fc fusion region peptide or leader or secretory sequence or a sequence which is employed for purification of the mature polypeptide or a proprotein sequence. Such fragments, derivatives and analogs are deemed to be within the scope of those skilled in the art from the teachings herein.

Of particular interest are substitutions of charged amino acids with another charged amino acid and with neutral or negatively charged amino acids. The latter results in proteins with reduced positive charge to improve the characteristics of a galectin 8, 9, 10, or 10SV protein. The prevention of aggregation is highly desirable. Aggregation of proteins not only results in a loss of activity but can also be problematic when preparing pharmaceutical formulations, because they can be immunogenic. (Pinckard et al,, *Clin. Exp. Immunol.* 2:331–340 (1967); Robbins et al., *Diabetes* 36:838–845 (1987); Cleland et al., *Crit. Rev. Therapeutic Drug Carrier Systems* 10:307–377 (1993)).

As indicated, changes are preferably of a minor nature, such as conservative amino acid substitutions that do not significantly affect the folding or activity of the protein (see Table 1).

TABLE 1

| Conservative Amino Acid Substitutions. | |
|---|---|
| Aromatic | Phenylalanine |
| | Tryptophan |
| | Tyrosine |
| Hydrophobic | Leucine |
| | Isoleucine |
| | Valine |
| Polar | Glutamine |
| | Asparagine |
| Basic | Arginine |
| | Lysine |
| | Histidine |
| Acidic | Aspartic Acid |
| | Glutamic Acid |
| Small | Alanine |
| | Serine |
| | Threonine |
| | Methionine |
| | Glycine |

Of course, the number of amino acid substitutions a skilled artisan would make depends on many factors, including those described above and below. Generally speaking, the number of substitutions for any given galectin 8, 9, 10, or 10SV polypeptide or mutant thereof will not be more than 50, 40, 30, 20, 10, 5, or 3, depending on the objective.

Amino acids in a galectin 8, 9, 10, or 10SV protein of the present invention that are essential for function can be identified by methods known in the art, such as site-directed mutagenesis or alanine-scanning mutagenesis (Cunningham and Wells, *Science* 244:1081–1085 (1989)). The latter procedure introduces single alanine mutations at every residue in the molecule. Sites that are critical for ligand binding can also be determined by structural analysis such as crystallization, nuclear magnetic resonance or photoaffinity labeling (Smith et al., *J. Mol. Biol.* 224:899–904 (1992) and de Vos et al., *Science* 255:306–312 (1992)).

The polypeptides of the present invention are preferably provided in an isolated form. By "isolated polypeptide" is intended a polypeptide removed from its native environment. Thus, a polypeptide produced and/or contained within a recombinant host cell is considered isolated for purposes of the present invention. Also intended as an "isolated polypeptide" are polypeptides that have been purified, partially or substantially, from a recombinant host cell. For example, a recombinantly produced version of a galectin 8, 9, 10, or 10SV polypeptide can be substantially purified by the one-step method described in Smith and Johnson, *Gene* 67:31–40 (1988).

The polypeptides of the present invention include the polypeptides encoded by the deposited cDNAs; a polypeptide comprising amino acids about 1 to about 323 in SEQ ID NO:2, about 1 to about 311 in SEQ ID NO:4, about 1 to about 317 in SEQ ID NO:6, and about 1 to about 200 in SEQ ID NO:8; a polypeptide comprising amino acids about 2 to about 323 in SEQ ID NO:2, about 2 to about 311 in SEQ ID NO:4, about 2 to about 317 in SEQ ID NO:6 and about 2 to about 200 in SEQ ID NO:8; as well as polypeptides which are at least 90% identical, still more preferably at least 95%, 96%, 97%, 98% or 99% identical to the polypeptides described above and also include portions of such polypeptides with at least 30 amino acids and more preferably at least 50 amino acids.

By a polypeptide having a n amino acid sequence at least, for example, 95% "identical" to a reference amino acid sequence of a galectin 8, 9, 10, or 10SV polypeptide is intended that the amino acid sequence of the polypeptide is identical to the reference sequence except that the polypeptide sequence may include up to five amino acid alterations per each 100 amino acids of the reference amino acid of the galectin 8, 9, 10, or 10SV polypeptide. In other words, to obtain a polypeptide having an amino acid sequence at least 95% identical to a reference amino acid sequence, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

As a practical matter, whether any particular polypeptide is at least 95%, 96%, 97%, 98% or 99% identical to, for instance, the amino acid sequence shown in FIGS. 1, 2A–2B, 3A–3B, or 4A–4B (SEQ ID NOs:2, 4, 6, or 8, respectively) or to the amino acid sequence encoded by one of the deposited cDNA clones (ATCC Deposit Numbers 97732, 97733 and 97734) can be determined conventionally using known computer programs such the Bestfit program (Wisconsin Sequence Analysis Package, Version 8 for Unix, Genetics Computer Group, University Research Park, 575 Science Drive, Madison, Wis. 53711). When using Bestfit or any other sequence alignment program to determine whether a particular sequence is, for instance, 95% identical to a reference sequence according to the present invention, the parameters are set, of course, such that the percentage of identity is calculated over the full length of the reference amino acid sequence and that gaps in homology of up to 5% of the total number of amino acid residues in the reference sequence are allowed.

The polypeptide of the present invention could be used as a molecular weight marker on SDS-PAGE gels or on molecular sieve gel filtration columns using methods well known to those of skill in the art.

In another aspect, the invention provides a peptide or polypeptide comprising an epitope-bearing portion of a polypeptide of the invention. The epitope of this polypeptide portion is an immunogenic or antigenic epitope described herein. An "immunogenic epitope" is defined as a part of a protein that elicits an antibody response when the whole protein is the immunogen. On the other hand, a region of a protein molecule to which an antibody can bind is defined as an "antigenic epitope." The number of immunogenic epitopes of a protein generally is less than the number of antigenic epitopes. See, for instance, Geysen et al., Proc. Natl. Acad. Sci. USA 81:3998–4002 (1983).

As to the selection of peptides or polypeptides bearing an antigenic epitope (ie., that contain a region of a protein molecule to which an antibody can bind), it is well known in that art that relatively short synthetic peptides that mimic part of a protein sequence are routinely capable of eliciting an antiserum that reacts with the partially mimicked protein. See, for instance, Sutcliffe, J. G., Shinnick, T. M., Green, N. and Learner, R. A. (1983) Antibodies that react with predetermined sites on proteins. Science 219:660–666. Peptides capable of eliciting protein-reactive sera are frequently represented in the primary sequence of a protein, can be characterized by a set of simple chemical rules, and are confined neither to immunodominant regions of intact proteins (i.e., immunogenic epitopes) nor to the amino or carboxyl terminals.

Antigenic epitope-bearing peptides and polypeptides of the invention are therefore useful to raise antibodies, including monoclonal antibodies, that bind specifically to a polypeptide of the invention. See, for instance, Wilson et al., Cell 37:767–778 (1984) at 777.

Antigenic epitope-bearing peptides and polypeptides of the invention preferably contain a sequence of at least seven, more preferably at least nine and most preferably between about at least 15 to about 30 amino acids contained within the amino acid sequence of a polypeptide of the invention.

Non-limiting examples of antigenic polypeptides or peptides that can be used to generate galectin 8, 9, 10, or 10SV-specific antibodies include: a polypeptide comprising amino acid residues from about 55–101, 137–162, 180–193, 216–266 in FIG. 1 (SEQ ID NO:2), 62–102, 226–259, 197–308 in FIGS. 2A–2B (SEQ ID NO:4), 25–77, 84–105, 129–140, 156–183, 195–215, and 241–257 in FIGS. 3A–3B (SEQ ID NO:6), and 25–77, 84–105, 129–140, and 156–183 in FIGS. 4A–4B (SEQ ID NO:8), respectively. As indicated above, the inventors have determined that the above polypeptide fragments are antigenic regions of the galectin 8, 9, 10, or 10SV protein.

The epitope-bearing peptides and polypeptides of the invention may be produced by any conventional means Houghten, R. A. (1985) General method for the rapid solid-phase synthesis of large numbers of peptides: specificity of antigen-antibody interaction at the level of individual amino acids. Proc. Natl. Acad. Sci. USA 82:5131–5135. This "Simultaneous Multiple Peptide Synthesis (SMPS)" process is further described in U.S. Pat. No. 4,631,211 to Houghten et al. (1986).

As one of skill in the art will appreciate, galectin 8, 9, 10, or 10SV polypeptides of the present invention and the epitope-bearing fragments thereof described above can be combined with parts of the constant domain of immunoglobulins (IgG), resulting in chimeric polypeptides. These fusion proteins facilitate purification and show an increased half-life in vivo. This has been shown, e.g., for chimeric proteins consisting of the first two domains of the human CD4-polypeptide and various domains of the constant regions of the heavy or light chains of mammalian immunoglobulins (EPA 394,827; Traunecker et al., Nature 331:84–86 (1988)). Fusion proteins that have a disulfide-linked dimeric structure due to the IgG part can also be more efficient in binding and neutralizing other molecules than the monomeric galectin 8, 9, 10, or 10SV protein or protein fragment alone (Fountoulakis et al., J. Biochem 270:3958–3964 (1995)).

Diagnosis and Prognosis

It is believed that certain tissues in mammals with certain diseases (cancer, autoimmune diseases, inflammatory diseases, asthma, and allergic diseases) express significantly altered (enhanced or decreased) levels of the galectin 8, 9, 10, or 10SV protein and MRNA encoding the galectin 8, 9, 10, or 10SV protein when compared to a corresponding "standard" mammal, i.e., a mammal of the same species not having the disease. Further, it is believed that altered levels of the galectin 8, 9, 10, or 10SV protein can be detected in certain body fluids (e.g., sera, plasma, urine, and spinal fluid) from mammals with the disease when compared to sera from mammals of the same species not having the disease. Thus, the invention provides a diagnostic method useful during diagnosis, which involves assaying the expression level of the gene encoding the galectin 8, 9, 10, or 10SV protein in mammalian cells or body fluid and comparing the gene expression level with a standard galectin 8, 9, 10, or 10SV gene expression level, whereby an increase or decrease in the gene expression level over the standard is indicative of the disease.

Where a diagnosis has already been made according to conventional methods, the present invention is useful as a prognostic indicator, whereby patients exhibiting altered galectin 8, 9, 10, or 10SV gene expression will experience a worse clinical outcome relative to patients expressing the gene at a normal level.

By "assaying the expression level of the gene encoding the galectin 8, 9, 10, or 10SV protein" is intended qualitatively or quantitatively measuring or estimating the level of the galectin 8, 9, 10, or 10SV protein or the level of the mRNA encoding the galectin 8, 9, 10, or 10SV protein in a first biological sample either directly (e.g., by determining or estimating absolute protein level or mRNA level) or relatively (e.g., by comparing to the galectin 8, 9, 10, or 10SV protein level or mRNA level in a second biological sample).

Preferably, the galectin 8, 9, 10, or 10SV protein level or mRNA level in the first biological sample is measured or estimated and compared to a standard galectin 8, 9, 10, or 10SV protein level or mRNA level, the standard being taken from a second biological sample obtained from an individual not having the cancer. As will be appreciated in the art, once a standard galectin 8, 9, 10, or 10SV protein level or mRNA level is known, it can be used repeatedly as a standard for comparison.

By "biological sample" is intended any biological sample obtained from an individual, cell line, tissue culture, or other source which contains galectin 8, 9, 10, or 10SV protein or mRNA. Biological samples include mammalian body fluids (such as sera, plasma, urine, synovial fluid and spinal fluid) which contain secreted galectin 8, 9, 10, or 10SV protein, and ovarian, prostate, heart, placenta, pancreas liver, spleen, lung, breast and umbilical tissue.

The present invention is useful for detecting diseases in mammals (for example, cancer, autoimmune diseases, inflammatory diseases, asthma, and allergic diseases). In particular the invention is useful during diagnosis of the of following types of cancers in mammals: melanoma, renal astrocytoma, Hodgkin disease, breast, ovarian, prostate, bone, liver, lung, pancreatic, and spleenic. Preferred mammals include monkeys, apes, cats, dogs, cows, pigs, horses, rabbits and humans. Particularly preferred are humans.

Total cellular RNA can be isolated from a biological sample using the single-step guanidinium-thiocyanate-phenol-chloroform method described in Chomczynski and Sachi, *Anal. Biochem.* 162:156–159 (1987). Levels of MRNA encoding the galectin 8, 9, 10, or 10SV protein are then assayed using any appropriate method. These include Northern blot analysis, (Harada et al., *Cell* 63:303–312 (1990) S1 nuclease mapping, (Fijita et al., *Cell* 49:357–367 (1987)) the polymerase chain reaction (PCR), reverse transcription in combination with the polymerase chain reaction (RT-PCR) (Makino et al., *Technique* 2:295–301 (1990), and reverse transcription in combination with the ligase chain reaction (RT-LCR).

Assaying galectin 8, 9, 10, or 10SV protein levels in a biological sample can be performed using antibody-based techniques. For example, galectin 8, 9, 10, or 10SV protein expression in tissues can be studied with classical immunohistological methods. (Jalkanen, M., et al., *J. Cell. Biol.* 101:976–985 (1985); Jalkanen, M., et al., *J. Cell. Biol.* 105:3087–3096 (1987)).

Other antibody-based methods useful for detecting galectin 8, 9, 10, or 10SV protein gene expression include immunoassays, such as the enzyme linked immunosorbent assay (ELISA) and the radioimmunoassay (RIA).

Suitable labels are known in the art and include enzyme labels, such as, Glucose oxidase, and radioisotopes, such as iodine ($^{125}$I, $^{121}$I), carbon ($^{14}$C), sulfur ($^{35}$S), tritium (3H), indium ($^{112}$In), and technetium ($^{99m}$Tc), and fluorescent labels, such as fluorescein and rhodamine, and biotin.

Therapeutics

It is to be understood that although the following discussion is specifically directed to human patients, the teachings are also applicable to any animal that expresses galectin 8, 9, 10, or 10SV.

As noted above, galectin 8, 9, 10, and 10SV share significant homology with other galectins. Galectin 1 induces apoptosis of T cells and T cell leukemia cell lines. Thus, it is believed by the inventors that galectin 8, 9, 10, and 10SV are active in modulating growth regulatory activities, immunomodulatory activity, cell-cell and cell-substrate interactions, and apoptosis.

The ability of galectin 8, 9, 10, or 10SV to modulate growth regulatory activity may be therapeutically valuable in the treatment of clinical manifestations of such cell regulatory disorders. Disorders which can be treated include, but should not be limited to, autoimmune disease, cancer (preferably, melanoma, renal, astrocytoma, and Hodgkin disease), inflammatory disease, wound healing, arteriosclerosis, other heart diseases, microbe infection (virus, fungal, bacterial, and parasite), asthma, and allergic diseases.

Given the activities modulated by galectin 8, 9, 10, and 10SV, it is readily apparent that a substantially altered (increased or decreased) level of expression of galectin 8, 9, 10, or 10SV in an individual compared to the standard or "normal" level produces pathological conditions such as those described above. It will also be appreciated by one of ordinary skill that the galectin 8, 9, 10, or 10SV protein of the invention will exert its modulating activities on any of its target cells. Therefore, it will be appreciated that conditions caused by a decrease in the standard or normal level of galectin 8, 9, 10, or 10SV activity in an individual, can be treated by administration of galectin 8, 9, 10, or 10SV protein or an agonist thereof. Thus, the invention further provides a method of treating an individual in need of an increased level of galectin 8, 9, 10, or 10SV activity comprising administering to such an individual a pharmaceutical composition comprising an amount of an isolated galectin 8, 9, 10, or 10SV polypeptide of the invention or an agonist thereof to increase the galectin 8, 9, 10, or 10SV activity level in such an individual.

A still further aspect of the invention is related to a method for treating an individual in need of a decreased level of galectin 8, 9, 10, or 10SV activity in the body comprising, administering to such an individual a composition comprising a therapeutically effective amount of a galectin 8, 9, 10, or 10SV antagonist. Preferred antagonists for use in the present invention are galectin 8, 9, 10, or 10SV-specific antibodies.

Modes of Administration

It will be appreciated that conditions caused by a decrease in the standard or normal level of galectin 8, 9, 10, or 10SV activity in an individual, can be treated by administration of galectin 8, 9, 10, or 10SV protein or an agonist thereof. Thus, the invention further provides a method of treating an individual in need of an increased level of galectin 8, 9, 10, or 10SV activity comprising administering to such an individual a pharmaceutical composition comprising an effective amount of an isolated galectin 8, 9, 10, or 10SV polypeptide of the invention, particularly a mature form of the galectin 8, 9, 10, or 10SV, effective to increase the galectin 8, 9, 10, or 10SV activity level in such an individual.

As a general proposition, the total pharmaceutically effective amount of galectin 8, 9, 10, or 10SV polypeptide administered parenterally per dose will be in the range of about 1 µg/kg/day to 10 mg/kg/day of patient body weight, although, as noted above, this will be subject to therapeutic discretion. More preferably, this dose is at least 0.01 mg/kg/day, and most preferably for humans between about 0.01 and 1 mg/kg/day for the hormone. If given continuously, the galectin 8, 9, 10, or 10SV polypeptide is typically administered at a dose rate of about 1 µg/kg/hour to about 50 µg/kg/hour, either by 14 injections per day or by continuous subcutaneous infusions, for example, using a mini-pump. An intravenous bag solution may also be employed.

Pharmaceutical compositions containing the galectin 8, 9, 10, or 10SV of the invention may be administered orally, rectally, parenterally, intracistemally, intravaginally, intraperitoneally, topically (as by powders, ointments, drops or transdermal patch), bucally, or as an oral or nasal spray. By "pharmaceutically acceptable carrier" is meant a non-toxic solid, semisolid or liquid filler, diluent, encapsulating material or formulation auxiliary of any type. The term "parenteral" as used herein refers to modes of administration which include intravenous, intramuscular, intraperitoneal, intrastemal, subcutaneous and intraarticular injection and infusion.

Chromosome Assays

The nucleic acid molecules of the present invention are also valuable for chromosome identification. The sequence is specifically targeted to and can hybridize with a particular location on an individual human chromosome. The mapping of DNAs to chromosomes according to the present invention is an important first step in correlating those sequences with genes associated with disease.

In certain preferred embodiments in this regard, the cDNA herein disclosed is used to clone genomic DNA of a galectin 8, 9, 10, or 10SV protein gene. This can be accomplished using a variety of well known techniques and libraries, which generally are available commercially. The genomic DNA then is used for in situ chromosome mapping using well known techniques for this purpose.

In addition, in some cases, sequences can be mapped to chromosomes by preparing PCR primers (preferably 15–25 bp) from the cDNA. Computer analysis of the 3' untranslated region of the gene is used to rapidly select primers that do not span more than one exon in the genomic DNA, thus complicating the amplification process. These primers are then used for PCR screening of somatic cell hybrids containing individual human chromosomes.

Fluorescence in situ hybridization ("FISH") of a cDNA clone to a metaphase chromosomal spread can be used to provide a precise chromosomal location in one step. This technique can be used with probes from the cDNA as short as 50 or 60 bp. For a review of this technique, see Verma et al., *Human Chromosomes: A Manual Of Basic Techniques*, Pergamon Press, New York (1988).

Once a sequence has been mapped to a precise chromosomal location, the physical position of the sequence on the chromosome can be correlated with genetic map data. Such data are found, for example, in V. McKusick, *Mendelian Inheritance In Man*, available on-line through Johns Hopkins University, Welch Medical Library. The relationship between genes and diseases that have been mapped to the same chromosomal region are then identified through linkage analysis (coinheritance of physically adjacent genes).

Next, it is necessary to determine the differences in the cDNA or genomic sequence between affected and unaffected individuals. If a mutation is observed in some or all of the affected individuals but not in any normal individuals, then the mutation is likely to be the causative agent of the disease.

Having generally described the invention, the same will be more readily understood by reference to the following examples, which are provided by way of illustration and are not intended as limiting.

EXAMPLES

Example 1

Expression and Purification of Galectin 8, 9, 10 and 10SV in *E. coli*

The DNA sequence encoding the galectin 9 protein in the deposited cDNA clone was amplified using PCR oligonucleotide primers specific to the amino terminal sequences of the galectin 9 protein and to vector sequences 3' to the gene. Additional nucleotides containing restriction sites to facilitate cloning are added to the 5' and 3' sequences.

The DNA sequence encoding the galectin 8 or 10SV protein in the deposited cDNA clone is amplified using PCR oligonucleotide primers specific to the nucleotide sequences encoding the amino terminal sequences of the galectin 8 or 10SV protein and to vector sequences 3' to the gene. Additional nucleotides containing restriction sites to facilitate cloning are added to the 5' and 3' sequences.

The cDNA sequence encoding the galectin 10 protein is amplified from either a human endometrial tumor or human fetal heart cDNA library using PCR oligonucleotide primers specific to the nucleotide sequences encoding the amino terminal sequences of the galectin 10 protein and to vector sequences 3' to the gene. Additional nucleotides containing restriction sites to facilitate cloning are added to the 5' and 3 sequences.

The 5' galectin 8 oligonucleotide primer has the sequence 5' cgc ccATGg CCTATGTCCCCGCACCG 3' (SEQ ID NO:41) containing the underlined NcoI restriction site and nucleotides 56 to 72 of the galectin 8 protein coding sequence in FIG. 1 (SEQ ID NO:1).

The 3' galectin 8 primer has the sequence 5' cgc AAG CTT TTAGATC TGGACATAGGAC 3' (SEQ ID NO:42) containing the underlined HindIII restriction site followed by nucleotides complementary to position 1005 to 1023 of the galectin 8 protein coding sequence in FIG. 1 (SEQ ID NO:1).

The 5' galectin 9 oligonucleotide primer has the sequence 5' cgc ccATGg CCTT CAGCGGTTCCCAG 3' (SEQ ID NO:43) containing the underlined NcoI restriction site and nucleotides 20 to 36 of the galectin 9 protein coding sequence in FIGS. 2A–2B (SEQ ID NO:3).

The 3' galectin 9 primer has the sequence 5' cgc AAG CTT CAGGGTT GGAAAGGCTG (SEQ ID NO:44) containing the underlined HindIII restriction site followed by nucleotides complementary to position 1029 to 1045 of the galectin 9 protein coding sequence in FIGS. 2A–2B (SEQ ID NO:3).

The 5' galectin 10 and 10SV oligonucleotide primer has the sequence 5' cgc CCATGc TGTTGTCCTTAAACAAC 3' (SEQ ID NO:45) containing the underlined SphI restriction site and nucleotides 122–138 of the galectin 10 protein coding sequence in FIGS. 3A–3B (SEQ ID NO:5).

The 3' galectin 10 primer has the sequence 5' cgc CTG CAG CACAGAA GCCATTCTG 3' (SEQ ID NO:46) containing the underlined PstI restriction site followed by nucleotides complementary to position 1105–1120 of the galectin 10 protein coding sequence in FIGS. 3A–3B (SEQ ID NO:5).

The 3' galectin 10SV primer has the sequence 5° CGC-CTGCAGCTA TGCAACTTTATAAAATATTCC 3' (SEQ ID NO:47) containing the underlined PstI restriction site followed by nucleotides complementary to 3' end of the galectin 10SV protein coding sequence in FIGS. 4A–4B (SEQ ID NO:7).

The restriction sites are convenient to restriction enzyme sites in the bacterial expression vector pQE60 (galectin 8 and 9) or pQE6 (galectin 10), which are used for bacterial expression in these examples. (Qiagen, Inc. 9259 Eton Avenue, Chatsworth, Calif., 91311). pQE60 encodes ampicillin antibiotic resistance ("Amp") and contains a bacterial origin of replication ("ori"), an IPTG inducible promoter, a ribosome binding site ("RBS"), a 6-His tag and restriction enzyme sites.

The amplified galectin 8, 9, 10, or 10SV DNA and the vector pQE60 or pQE6 both are digested with NcoI and HindIII (for galectin 8 and 9) or SphI and PstI (for galectin 10) and the digested DNAs are then ligated together. Insertion of the galectin 8, 9, 10, or 10SV protein DNA into the restricted pQE60 or pQE6 vector placed the galectin 8, 9, 10, or 10SV protein coding region downstream of and operably linked to the vector's IPTG-inducible promoter and in-frame with an initiating AUG appropriately positioned for translation of galectin 8, 9, 10, or 10SV protein.

The ligation mixture is transformed into competent *E. coli* cells using standard procedures. Such procedures are described in Sambrook et al., MOLECULAR CLONING: A LABORATORY MANUAL, 2nd Ed.; Cold Spring Harbor Laboratory Press, Cold Spring Harbor, N.Y. (1989). *E. coli* strain M15/rep4, containing multiple copies of the plasmid pREP4, which expresses lac repressor and confers kanamycin resistance ("Kan"), is used in carrying out the example described herein. This strain, which is only one of many that are suitable for expressing galectin 8, 9, 10, or 10SV protein, is available commercially from Qiagen.

Transformants are identified by their ability to grow on LB plates in the presence of ampicillin and kanamycin. Plasmid DNA is isolated from resistant colonies and the identity of the cloned DNA confirmed by restriction analysis.

Clones containing the desired constructs are grown overnight ("O/N") in liquid culture in LB media supplemented with both ampicillin (100 μg/ml) and kanamycin (25 μg/ml).

The O/N culture is used to inoculate a large culture, at a dilution of approximately 1:100 to 1:250. The cells are grown to an optical density at 600nm ("OD600") of between 0.4 and 0.6. Isopropyl-B-D-thiogalactopyranoside ("IPTG") is then added to a final concentration of 1 mM to induce transcription from lac repressor sensitive promoters, by inactivating the lacI repressor. Cells subsequently are incubated further for 3 to 4 hours. Cells then are harvested by centrifugation and disrupted, by standard methods. Inclusion bodies are purified from the disrupted cells using routine collection techniques, and protein is solubilized from the inclusion bodies into 8M urea. The 8M urea solution containing the solubilized protein is passed over a PD-10 column in 2×phosphate-buffered saline ("PBS"), thereby removing the urea, exchanging the buffer and refolding the protein. The protein is purified by a further step of chromatography to remove endotoxin. Then, it is sterile filtered. The sterile filtered protein preparation is stored in 2×PBS at a concentration of 95 μ/ml.

Example 2

Cloning and Expression of Galectin 8, 9, 10 and 10SV protein in a Baculovirus Expression System The cDNA sequence encoding the full length galectin 8, 9, 10, or 10SV protein in the deposited clone is amplified using PCR oligonucleotide primers corresponding to the 5' and 3' sequences of the gene:

The 5' galectin 8 oligonucleotide primer has the sequence 5' cgc CCCGGG GCCTATGTCCCCGCAC 3' (SEQ ID NO:48) containing the underlined SmaI restriction site and nucleotides 55 to 70 of the galectin 8 protein coding sequence in FIG. 1 (SEQ ID NO:1).

The 3' galectin 8 primer has the sequence 5' cgc GGT ACC TTAGATCTGG ACATAGGAC 3' (SEQ ID NO:49) containing the underlined Asp718 restriction site followed by nucleotides complementary to position 1005 to 1023 of the galectin 8 protein coding sequence in FIG. 1 (SEQ ID NO:1).

The 5' galectin 9 oligonucleotide primer has the sequence 5' cgc CCCGGG GCCTTCAGCGGTTCCCAG 3' (SEQ ID NO:50) containing the underlined SmaI restriction site and nucleotides 19 to 36 of the galectin 9 protein coding sequence in FIGS. 2A–2B (SEQ ID NO:3).

The 3' galectin 9 primer has the sequence 5' cgc GGT ACC CAGGGTTGG AAAGGCTG 3' (SEQ ID NO:51) containing the underlined Asp718 restriction site followed by nucleotides complementary to position 1029 to 1045 of the galectin 9 protein coding sequence in FIGS. 2A–2B (SEQ ID NO:3).

The 5' galectin 10 oligonucleotide primer has the sequence 5' cgc CCCGGG TTGTCCTTAAACAACCTAC 3' (SEQ ID NO:52) containing the underlined SmaI restriction site and nucleotides 124–142 of the galectin 10 protein coding sequence in FIGS. 3A–3B (SEQ ID NO:5).

The 3' galectin 10 primer has the sequence 5' cgc GGT ACC CACA GAAGCCATTCTG 3' (SEQ ID NO:53) containing the underlined Asp718 restriction site followed by nucleotides complementary to position 1105–1120 of the galectin 10 protein coding sequence in FIGS. 3A–3B (SEQ ID NO:5).

The 3' galectin 10SV primer has the sequence 5° CGC GGTACCCTA TGCAACTTTATAAAATATTCC 3' (SEQ ID NO:54) containing the underlined Asp718 restriction site followed by nucleotides complementary to the 3' end of the galectin 10SV protein coding sequence in FIGS. 4A–4B (SEQ ID NO:7).

An efficient signal for initiation of translation in eukaryotic cells, as described by Kozak, M., *J. Mol. Biol.* 196:947–950 (1987) is appropriately located in the vector portion of the construct.

The amplified fragment is isolated from a 1% agarose gel using a commercially available kit ("Geneclean," BIO 101 Inc., La Jolla, Calif.). The fragment then is digested with XbaI and again is purified on a 1% agarose gel. This fragment is designated herein F2.

The vector pA2-GP is used to express the galectin 8, 9, 10, or 10SV protein in the baculovirus expression system, using standard methods, as described in Summers et al, A MANUAL OF METHODS FOR BACULOVIRUS VECTORS AND INSECT CELL CULTURE PROCEDURES, Texas Agricultural Experimental Station Bulletin No. 1555 (1987). This expression vector contains the strong polyhedrin promoter of the *Autographa californica* nuclear polyhedrosis virus (AcMNPV) followed by convenient restriction sites. The signal peptide of AcMNPV gp67, including the N-terminal methionine, is located just upstream of a BamHI site. The polyadenylation site of the simian virus 40 ("SV40") is used for efficient polyadenylation. For an easy selection of recombinant virus the beta-galactosidase gene from *E. coli* is inserted in the same orientation as the polyhedrin promoter and is followed by the polyadenylation signal of the polyhedrin gene. The polyhedrin sequences are flanked at both sides by viral sequences for cell-mediated homologous recombination with wild-type viral DNA to generate viable virus that express the cloned polynucleotide.

Many other baculovirus vectors could be used in place of pA2-GP, such as pAc373, pVL941 and pAcIM1 provided, as those of skill readily will appreciate, that construction provides appropriately located signals for transcription, translation, trafficking and the like, such as an in-frame AUG and a signal peptide, as required. Such vectors are described in Luckow et al., *Virology* 170:31–39, among others.

The plasmid is digested with the restriction enzyme SmaI and Asp718 and then is dephosphorylated using calf intestinal phosphatase, using routine procedures known in the art. The DNA is. then isolated from a 1% agarose gel using a commercially available kit ("Geneclean" BIO 101 Inc., La Jolla, Calif.). This vector DNA is designated herein "V2".

Fragment F2 and the dephosphorylated plasmid V2 are ligated together with T4 DNA ligase. *E. coli* HB101 cells are transformed with ligation mix and spread on culture plates. Bacteria are identified that contain the plasmid with the human galectin 8, 9, 10, or 10SV gene by digesting DNA from individual colonies using XbaI and then analyzing the digestion product by gel electrophoresis. The sequence of the cloned fragment is confirmed by DNA sequencing. This plasmid is designated herein pBacgalectin 8, 9, 10, or 10SV.

5 μg of the plasmid pBacgalectin 8, 9, 10, or 10SV is co-transfected with 1.0 μg of a commercially available linearized baculovirus DNA ("BaculoGold™ baculovirus DNA", Pharmingen, San Diego, Calif.), using the lipofection method described by Felgner et al., Proc. Natl. Acad. Sci. USA 84:7413–7417 (1987). 1 μg of BaculoGold™ virus DNA and 5 μg of the plasmid pBacgalectin 8, 9, 10, or 10SV are mixed in a sterile well of a microtiter plate containing 50 μl of serum-free Grace's medium (Life Technologies Inc., Gaithersburg, Md.). Afterwards 10 μl Lipofectin plus 90 μl Grace's medium are added, mixed and incubated for 15 minutes at room temperature. Then the transfection mixture is added drop-wise to Sf9 insect cells (ATCC CRL 1711) seeded in a 35 mm tissue culture plate with 1 ml Grace's medium without serum. The plate is rocked back and forth to mix the newly added solution. The plate is then incubated for 5 hours at 27° C. After 5 hours the transfection solution is removed from the plate and 1 ml of Grace's insect medium supplemented with 10% fetal calf serum is added. The plate is put back into an incubator and cultivation is continued at 27° C. for four days.

After four days the supernatant is collected and a plaque assay is performed, as described by Summers and Smith, cited above. An agarose gel with "Blue Gal" (Life Technologies Inc., Gaithersburg) is used to allow easy identification and isolation of gal-expressing clones, which produce blue-stained plaques. (A detailed description of a "plaque assay" of this type can also be found in the user's guide for insect cell culture and baculovirology distributed by Life Technologies Inc., Gaithersburg, page 9–10).

Four days after serial dilution, the virus is added to the cells. After appropriate incubation, blue stained plaques are picked with the tip of an Eppendorf pipette. The agar containing the recombinant viruses is then resuspended in an Eppendorf tube containing 200 μl of Grace's medium. The agar is removed by a brief centrifugation and the supernatant containing the recombinant baculovirus is used to infect Sf9 cells seeded in 35 mm dishes. Four days later the supernatants of these culture dishes are harvested and then they are stored at 4° C. A clone containing properly inserted HESSB I, II and III is identified by DNA analysis including restriction mapping and sequencing. This is designated herein as V-galectin 8, 9, 10, or 10SV.

Sf9 cells are grown in Grace's medium supplemented with 10% heat-inactivated FBS. The cells are infected with the recombinant baculovirus V-galectin 8, 9, 10, or 10SV at a multiplicity of infection ("MOI") of about 2 (about 1 to about 3). Six hours later the medium is removed and is replaced with SF900 II medium minus methionine and cysteine (available from Life Technologies Inc., Gaithersburg). 42 hours later, 5 μCi of $^{35}$S-methionine and 5 μCi $^{35}$S-cysteine (available from Amersham) are added. The cells are further incubated for 16 hours and then they are harvested by centrifugation, lysed and the labeled proteins are visualized by SDS-PAGE and autoradiography.

Example 3

Cloning and Expression in Mammalian Cells

Most of the vectors used for the transient expression of the galectin 8, 9, 10, or 10SV protein gene sequence in mammalian cells should carry the SV40 origin of replication. This allows the replication of the vector to high copy numbers in cells (e.g. COS cells) which express the T antigen required for the initiation of viral DNA synthesis. Any other mammalian cell line can also be utilized for this purpose.

A typical mammalian expression vector contains the promoter element, which mediates the initiation of transcription of MRNA, the protein coding sequence, and signals required for the termination of transcription and polyadenylation of the transcript. Additional elements include enhancers, Kozak sequences and intervening sequences flanked by donor and acceptor sites for RNA splicing. Highly efficient transcription can be achieved with the early and late promoters from SV40, the long terminal repeats (LTRs) from Retroviruses, e.g. RSV, HTLVI, HIVI and the early promoter of the cytomegalovirus (CMV). However, cellular signals can also be used (e.g., human actin promoter). Suitable expression vectors for use in practicing the present invention include, for example, vectors such as pSVL and pMSG (Pharmacia, Uppsala, Sweden), pRSVcat (ATCC 37152), pSV2dhfr (ATCC 37146) and pBC12MI (ATCC 67109). Mammalian host cells that could be used include, human HeLa, 283, H9 and Jurkart cells, mouse NIH3T3 and C127 cells, Cos 1, Cos 7 and CV1, African green monkey cells, quail QC1–3 cells, mouse L cells and Chinese hamster ovary cells.

Alternatively, the gene can be expressed in stable cell lines that contain the gene integrated into a chromosome. The co-transfection with a selectable marker such as dhfr, gpt, neomycin, hygromycin allows the identification and isolation of the transfected cells.

The transfected gene can also be amplified to express large amounts of the encoded protein. The DHFR (dihydrofolate reductase) is a useful marker to develop cell lines that carry several hundred or even several thousand copies of the gene of interest. Another useful selection marker is the enzyme glutamine synthase (GS) Murphy et al., *Biochem. J.* 227:277–279 (1991); Bebbington et al., *Bio/Technology* 10:169–175 (1992)). Using these markers, the mammalian cells are grown in selective medium and the cells with the highest resistance are selected. These cell lines contain the amplified gene(s) integrated into a chromosome. Chinese hamster ovary (CHO) cells are often used for the production of proteins.

The expression vectors pC1 and pC4 contain the strong promoter (LTR) of the Rous Sarcoma Virus (Cullen et al., *Molecular and Cellular Biology*, 438–4470 (March, 1985)) plus a fragment of the CMV-enhancer (Boshart et al., *Cell* 41:521–530 (1985)). Multiple cloning sites, e.g., with the restriction enzyme cleavage sites BamHI, XbaI and Asp718, facilitate the cloning of the gene of interest. The vectors contain in addition the 3' intron, the polyadenylation and termination signal of the rat preproinsulin gene.

Example 3(a)

Cloning and Expression in COS Cells

The expression plasmid, pgalectin 8, 9, 10, or 10SV HA, is made by cloning a cDNA encoding galectin 8, 9, 10, or 10SV into the expression vector pcDNAI/Amp (which can be obtained from Invitrogen, Inc.).

The expression vector pcDNAI/amp contains: (1) an *E. coli* origin of replication effective for propagation in *E. coli* and other prokaryotic cells; (2) an ampicillin resistance gene for selection of plasmid-containing prokaryotic cells; (3) an SV40 origin of replication for propagation in eukaryotic cells; (4) a CMV promoter, a polylinker, an SV40 intron, and a polyadenylation signal arranged so that a cDNA conveniently can be placed under expression control of the CMV promoter and operably linked to the SV40 intron and the polyadenylation signal by means of restriction sites in the polylinker.

A DNA fragment encoding the galectin 8, 9, 10, or 10SV protein and an HA tag fused in frame to its 3' end is cloned into the polylinker region of the vector so that recombinant protein expression is directed by the CMV promoter. The HA tag corresponds to an epitope derived from the influenza hemagglutinin protein described by Wilson et al., *Cell* 37:767–778 (1984). The fusion of the HA tag to the target protein allows easy detection of the recombinant protein with an antibody that recognizes the HA epitope.

The plasmid construction strategy is as follows. The galectin 8, 9, 10, or 10SV cDNA of the deposited clone is amplified using primers that contain convenient restriction sites, much as described above regarding the construction of expression vectors for expression of galectin 8, 9, 10, or 10SV in *E. coli*. To facilitate detection, purification and characterization of the expressed galectin 8, 9, 10, or 10SV, one of the primers contains a hemagglutinin tag ("HA tag") as described above.

Suitable primers include the following, which are used in this example. The 5' galectin 8 primer has the sequence 5' cgc CCC GGG gcc atc ATG GCCTATGTCCCCG 3' (SEQ ID NO:55) containing the underlined SmaI restriction enzyme site followed by nucleotide sequence 52–67 of FIG. 1 (SEQ ID NO:1).

The 3' galectin 8 primer has the sequence 5' cgc GGT ACC TTAGAT CTGGACATAGGAC 3' (SEQ ID NO:56) containing the Asp718 restriction followed by nucleotides complementary to nucleotides 1005–1023 of the galectin 8 coding sequence set out in FIG. 1 (SEQ ID NO:1).

The 5' galectin 9 primer has the sequence 5' cgc CCC GGG gcc atc ATGGCCTTCAGCGGTTC 3' (SEQ ID NO:57) containing the underlined SmaI restriction enzyme site followed by the nucleotide sequence of bases 16–32 of FIGS. 2A–2B (SEQ ID NO:3).

The 3' galectin 9 primer has the sequence 5' cgc GGT ACC CAGGGTT GGAAAGGCTG 3' (SEQ ID NO:58) containing the Asp718 restriction followed by nucleotides complementary to nucleotides 1029–1045 of the galectin 9 coding sequence set out in FIGS. 2A–2B (SEQ ID NO:3), including the stop codon.

The 5' galectin 10 and 10SV primer has the sequence 5' cgc CCC GGG gcc atc ATGATGTTGTCCTTAAAC 3' (SEQ ID NO:59) containing the underlined SmaI restriction enzyme site followed by nucleotide sequence 118–135 of FIGS. 3A–3B (SEQ ID NO:5).

The 3' galectin 10 primer has the sequence 5' cgc GGT ACC CACAG AAGCCATTCTG 3' (SEQ ID NO:60) containing the Asp718 restriction followed by nucleotides complementary to nucleotides 1105–1120 set out in FIGS. 3A–3B (SEQ ID NO:5).

The 3' galectin 10SV primer has the sequence 5° CGC GGTACCCTA TGCAACTTTATAAAATATTCC 3' (SEQ ID NO:54) containing the Asp718 restriction followed by nucleotides complementary to the 3' end of the galectin 10SV coding sequence set out in FIGS. 4A–4B (SEQ ID NO:7).

The PCR amplified DNA fragment and the vector, pcDNAI/Amp, are digested with HindIII and XhoI and then ligated. The ligation mixture is transformed into *E. coli* strain SURE (available from Stratagene Cloning Systems, 11099 North Torrey Pines Road, La Jolla, Calif. 92037), and the transformed culture is plated on ampicillin media plates which then are incubated to allow growth of ampicillin resistant colonies. Plasmid DNA is isolated from resistant colonies and examined by restriction analysis and gel sizing for the presence of the galectin 8, 9, 10, or 10SV-encoding fragment.

For expression of recombinant galectin 8, 9, 10, or 10SV, COS cells are transfected with an expression vector, as described above, using DEAE-DEXTRAN, as described, for instance, in Sambrook et al., MOLECULAR CLONING: A LABORATORY MANUAL, Cold Spring Laboratory Press, Cold Spring Harbor, N.Y. (1989). Cells are incubated under conditions for expression of galectin 8, 9, 10, or 10SV by the vector.

Expression of the galectin 8, 9, 10, or 10SV HA fusion protein is detected by radiolabelling and immunoprecipitation, using methods described in, for example Harlow et al., ANTIBODIES: A LABORATORY MANUAL, 2nd Ed.; Cold Spring Harbor Laboratory Press, Cold Spring Harbor, N.Y. (1988). To this end, two days after transfection, the cells are labeled by incubation in media containing $^{35}$S-cysteine for 8 hours. The cells and the media are collected, and the cells are washed and the lysed with detergent-containing RIPA buffer: 150 mM NaCl, 1% NP-40, 0.1% SDS, 1% NP-40, 0.5% DOC, 50 mM TRIS, pH 7.5, as described by Wilson et al. cited above. Proteins are precipitated from the cell lysate and from the culture media using an HA-specific monoclonal antibody. The precipitated proteins then are analyzed by SDS-PAGE gels and autoradiography. An expression product of the expected size is seen in the cell lysate, which is not seen in negative controls.

Example 3(b)

Cloning and Expression in CHO Cells

The vector pC1 is used for the expression of galectin 8, 9, 10, or 10SV protein. Plasmid pC1 is a derivative of the plasmid pSV2-dhfr [ATCC Accession No. 37146]. Both plasmids contain the mouse DHFR gene under control of the SV40 early promoter. Chinese hamster ovary- or other cells lacking dihydrofolate activity that are transfected with these plasmids can be selected by growing the cells in a selective medium (alpha minus MEM, Life Technologies) supplemented with the chemotherapeutic agent methotrexate. The amplification of the DHFR genes in cells resistant to methotrexate (MTX) has been well documented (see, e.g., Alt, F. W., Kellems, R. M., Bertino, J. R., and Schimke, R. T., 1978, *J. Biol. Chem.* 253:1357–1370, Hamlin, J. L. and Ma, C. 1990, *Biochem. et Biophys. Acta,* 1097:107–143, Page, M. J. and Sydenham, M. A., *Biotechnology* 9:64–68 (1991)). Cells grown in increasing concentrations of MIX develop resistance to the drug by overproducing the target enzyme, DHFR, as a result of amplification of the DHFR gene. If a second gene is linked to the DHFR gene it is usually co-amplified and over-expressed. It is state of the art to develop cell lines carrying more than 1,000 copies of the genes. Subsequently, when the methotrexate is withdrawn, cell lines contain the amplified gene integrated into the chromosome(s).

Plasmid pC1 contains for the expression of the gene of interest a strong promoter of the long terminal repeat (LTR) of the Rouse Sarcoma Virus (Cullen, et al., Molecular and Cellular Biology, March 1985:438–4470) plus a fragment isolated from the enhancer of the immediate early gene of human cytomegalovirus (CMV) (Boshart et al., *Cell* 41:521–530, 1985). Downstream of the promoter are the following single restriction enzyme cleavage sites that allow the integration of the genes: BamHI, PvuII, and NruI. Behind these cloning sites the plasmid contains translational stop codons in all three reading frames followed by the 3' intron and the polyadenylation site of the rat preproinsulin gene. Other high efficient promoters can also be used for the expression, e.g., the human β-actin promoter, the SV40 early or late promoters or the long terminal repeats from other retroviruses, e.g., HIV and HTLVI. For the polyadenylation of the mRNA other signals, e.g., from the human growth hormone or globin genes can be used as well.

Stable cell lines carrying a gene of interest integrated into the chromosomes can also be selected upon co-transfection with a selectable marker such as gpt, G418 or hygromycin. It is advantageous to use more than one selectable marker in the beginning, e.g., G418 plus methotrexate.

The plasmid pC1 is digested with the restriction enzyme BamHI and then dephosphorylated using calf intestinal phosphates by procedures known in the art. The vector is then isolated from a 1% agarose gel.

The DNA sequence encoding galectin 8, 9, or 10SV, ATCC Deposit Nos. 97732, 97733 and 97734, respectively, is amplified using PCR oligonucleotide primers corresponding to the 5' and 3' sequences of the gene. The galectin 10 sequence is similarly amplified from a human endometrial tumor or human fetal heart cDNA library.

The 5' galectin 8 primer has the sequence 5' cgc CCCGGGgccatcATGGCCTATGTCCCCG 3' (SEQ ID NO:55) containing the underlined SmaI restriction enzyme site followed by nucleotide sequence 52–67 of FIG. 1 (SEQ ID NO:1). Inserted into an expression vector, as described below, the 5' end of the amplified fragment encoding human galectin 8 provides an efficient signal peptide. An efficient signal for initiation of translation in eukaryotic cells, as described by Kozak, M., *J. Mol. Biol.* 196:947–950 (1987) is appropriately located in the vector portion of the construct.

The 3' galectin 8 primer has the sequence 5' cgc GGT ACC TTAGAT CTGGACATAGGAC 3' (SEQ ID NO:56) containing the Asp718 restriction followed by nucleotides complementary to nucleotides 1005–1023 of the galectin 8 coding sequence set out in FIG. 1 (SEQ ID NO:1).

The 5' galectin 9 primer has the sequence 5' cgc CCC GGG gcc atc ATGGCCTTCAGCGGTTC 3' (SEQ ID NO:57) containing the underlined SmaI restriction enzyme site followed by the nucleotide sequence of bases 16–32 of FIGS. 2A–2B (SEQ ID NO:3). Inserted into an expression vector, as described below, the 5' end of the amplified fragment encoding human galectin 9 provides an efficient signal peptide. An efficient signal for initiation of translation in eukaryotic cells, as described by Kozak, M., *J. Mol. Biol.* 196:947–950 (1987) is appropriately located in the vector portion of the construct.

The 3' galectin 9 primer has the sequence 5' cgc GGT ACC CAGGGTT GGAAAGGCTG 3' (SEQ ID NO:58) containing the Asp718 restriction followed by nucleotides complementary to nucleotides 1029–1045 of the galectin 9 coding sequence set out in FIGS. 2A–2B (SEQ ID NO:3), including the stop codon.

The 5' galectin 10 and 10SV primer has the sequence 5' cgc CCC GGG gcc atc ATGATGTTGTCCTTAAAC 3' (SEQ ID NO:59) containing the underlined SmaI restriction enzyme site followed by nucleotide sequence 118–135 of FIGS. 3A–3B (SEQ ID NO:5). Inserted into an expression vector, as described below, the 5' end of the amplified fragment encoding human galectin 10 provides an efficient signal peptide. An efficient signal for initiation of translation in eukaryotic cells, as described by Kozak, M., *J. Mol. Biol.* 196:947–950 (1987) is appropriately located in the vector portion of the construct.

The 3' galectin 10 primer has the sequence 5' cgc GGTACCCACAGAAGCCATTCTG 3' (SEQ ID NO:60) containing the Asp718 restriction followed by nucleotides complementary to nucleotides 1105–1120 set out in FIGS. 3A–3B (SEQ ID NO:5).

The 3' galectin 10SV primer has the sequence 5° CGC GGTACCCTATGCAACTTTATAAAATATTCC 3' (SEQ ID NO:54) containing the Asp718 restriction followed by nucleotides complementary to the 3' end of the galectin 10SV coding sequence set out in FIGS. 4A–4B (SEQ ID NO:7).

The amplified fragments are isolated from a 1% agarose gel as described above and then digested with the endonucleases SmaI and Asp718 and then purified again on a 1% agarose gel.

The isolated fragment and the dephosphorylated vector are then ligated with T4 DNA ligase. *E. coli* HB101 cells are then transformed and bacteria identified that contained the plasmid pC1 inserted in the correct orientation using the restriction enzyme SmaI. The sequence of the inserted gene is confirmed by DNA sequencing.

Transfection of CHO-DHFR-cells

Chinese hamster ovary cells lacking an active DHFR enzyme are used for transfection. Five μg of the expression plasmid C1 are cotransfected with 0.5 μg of the plasmid pSVneo using the lipofecting method (Felgner et al., supra). The plasmid pSV2-neo contains a dominant selectable marker, the gene neo from Tn5 encoding an enzyme that confers resistance to a group of antibiotics including G418. The cells are seeded in alpha minus MEM supplemented with 1 mg/ml G418. After 2 days, the cells are trypsinized and seeded in hybridoma cloning plates (Greiner, Germany) and cultivated from 10–14 days. After this period, single clones are trypsinized and then seeded in 6-well petri dishes using different concentrations of methotrexate (25 nM, 50 nM, 100 nM, 200 nM, 400 nM). Clones growing at the highest concentrations of methotrexate are then transferred to new 6-well plates containing even higher concentrations of methotrexate (500 nM, 1 μM, 2 μM, 5 μM). The same procedure is repeated until clones grow at a concentration of 100 μM.

The expression of the desired gene product is analyzed by Western blot analysis and SDS-PAGE.

Example 4

Tissue Distribution of Protein Expression

Northern blot analysis is carried out to examine galectin 8, 9, 10, or 10SV gene expression in human tissues, using methods described by, among others, Sambrook et al., cited above. A cDNA probe containing the entire nucleotide sequence of the galectin 8, 9, 10, or 10SV protein (SEQ ID NO:1, 3, 5, or 7, respectively) is labeled with $^{32}$P using the rediprime™ DNA labeling system (Amersham Life Science), according to manufacturer's instructions. After labeling, the probe is purified using a CHROMA SPIN-100™ column (Clontech Laboratories, Inc.), according to manufacturer's protocol number PT1200-1. The purified labeled probe is then used to examine various human tissues for galectin 8,9, 10, or 10SV MRNA.

Multiple Tissue Northern (MTN) blots containing various human tissues (H) or human immune system tissues (IM) are obtained from Clontech and are examined with labeled probe using ExpressHyb™ hybridization solution (Clontech) according to manufacturer's protocol number PT1190-1. Following hybridization and washing, the blots are mounted and exposed to film at −70° C. overnight, and films developed according to standard procedures.

It will be clear that the invention may be practiced otherwise than as particularly described in the foregoing description and examples.

Numerous modifications and variations of the present invention are possible in light of the above teachings and, therefore, are within the scope of the appended claims.

The entire disclosure of all publications (including patents, patent applications, journal articles, laboratory manuals, books, or other documents) cited herein are hereby incorporated by reference.

What is claimed is:

1. An isolated polynucleotide comprising a nucleotide sequence encoding an amino acid sequence at least 90% identical to amino acids 2 to 311 of SEQ ID NO:4, wherein said amino acid sequence has Galectin 9 activity measured by lactose binding.

2. The polynucleotide of claim 1, comprising nucleotides 19 to 948 of SEQ ID NO:3.

3. The polynucleotide of claim 1, comprising a nucleotide sequence encoding an amino acid sequence at least 90% identical to amino acids 1 to 311 of SEQ ID NO:4 wherein said amino acid sequence has Galectin 9 activity measured by lactose binding.

4. The polynucleotide of claim 3, comprising nucleotides 16 to 948 of SEQ ID NO:3.

5. The polynucleotide of claim 1, further comprising a heterologous polynucleotide.

6. The polynucleotide of claim 5, wherein said heterologous polynucleotide encodes a heterologous polypeptide.

7. A method of producing a vector which comprises inserting the polynucleotide of claim 1 into a vector.

8. A vector comprising the polynucleotide of claim 1.

9. The vector of claim 8, wherein said polynucleotide is operably associated with a heterologous regulatory polynucleotide.

10. A host cell comprising the polynucleotide of claim 1.

11. The host cell of claim 10, wherein said polynucleotide is operably associated with a heterologous regulatory polynucleotide.

12. A method of producing a polypeptide which comprises culturing the host cell of claim 11 under conditions such that said polypeptide is expressed, and recovering said polypeptide.

* * * * *

SEQUENCE LISTING

```
<160> NUMBER OF SEQ ID NOS: 60

<210> SEQ ID NO 1
<211> LENGTH: 1138
<212> TYPE: DNA
<213> ORGANISM: Homo sapiens
<220> FEATURE:
<221> NAME/KEY: CDS
<222> LOCATION: (52)..(1020)

<400> SEQUENCE: 1
ttcggcacga gagctcttct cacaggacca gccactagcg cacctcgagc g atg gcc        57
                                                          Met Ala
                                                            1 tat gtc ccc gca ccg ggc tac cag ccc acc tac aac ccg acg ctg cct       105
Tyr Val Pro Ala Pro Gly Tyr Gln Pro Thr Tyr Asn Pro Thr Leu Pro
      5              10                  15 tac tac cag ccc atc ccg ggc ggg ctc aac gtg gga atg tct gtt tac       153
Tyr Tyr Gln Pro Ile Pro Gly Gly Leu Asn Val Gly Met Ser Val Tyr
 20                  25                  30 atc caa gga gtg gcc agc gag cac atg aag cgg ttc ttc gtg aac ttt       201
Ile Gln Gly Val Ala Ser Glu His Met Lys Arg Phe Phe Val Asn Phe
 35                  40                  45                  50 gtg gtt ggg cag gat ccg ggc tca gac gtc gcc ttc cac ttc aat ccg       249
Val Val Gly Gln Asp Pro Gly Ser Asp Val Ala Phe His Phe Asn Pro
                 55                  60                  65 cgg ttt gac ggc tgg gac aag gtg gtc ttc aac acg ttg cag ggc ggg       297
Arg Phe Asp Gly Trp Asp Lys Val Val Phe Asn Thr Leu Gln Gly Gly
             70                  75                  80 aag tgg ggc agc gag gag agg aag agg agc atg ccc ttc aaa aag ggt       345
Lys Trp Gly Ser Glu Glu Arg Lys Arg Ser Met Pro Phe Lys Lys Gly
         85                  90                  95 gcc gcc ttt gag ctg gtc ttc ata gtc ctg gct gag cac tac aag gtg       393
Ala Ala Phe Glu Leu Val Phe Ile Val Leu Ala Glu His Tyr Lys Val
    100                 105                 110 gtg gta aat gga aat ccc ttc tat gag tac ggg cac cgg ctt ccc cta       441
Val Val Asn Gly Asn Pro Phe Tyr Glu Tyr Gly His Arg Leu Pro Leu
115                 120                 125                 130 cag atg gtc acc cac ctg caa gtg gat ggg gat ctg caa ctt caa tca       489
Gln Met Val Thr His Leu Gln Val Asp Gly Asp Leu Gln Leu Gln Ser
                135                 140                 145 atc aac ttc atc gga ggc cag ccc ctc cgg ccc cag gga ccc ccg atg       537
Ile Asn Phe Ile Gly Gly Gln Pro Leu Arg Pro Gln Gly Pro Pro Met
            150                 155                 160 atg cca cct tac cct ggt ccc gga cat tgc cat caa cag ctg aac agc       585
Met Pro Pro Tyr Pro Gly Pro Gly His Cys His Gln Gln Leu Asn Ser
        165                 170                 175 ctg ccc acc atg gaa gga ccc cca acc ttc aac ccg cct gtg cca tat       633
Leu Pro Thr Met Glu Gly Pro Pro Thr Phe Asn Pro Pro Val Pro Tyr
    180                 185                 190 ttc ggg agg ctg caa gga ggg ctc aca gct cga aga acc atc atc atc       681
Phe Gly Arg Leu Gln Gly Gly Leu Thr Ala Arg Arg Thr Ile Ile Ile
```

|     |     |     |     |     |     |     |     |     |     |     |     |     |     |     |     | |
|---|---|---|---|---|---|---|---|---|---|---|---|---|---|---|---|---|
| | 195 | | | | 200 | | | | 205 | | | | 210 | | | |
| aag | ggc | tat | gtg | cct | ccc | aca | ggc | aag | agc | ttt | gct | atc | aac | ttc | aag | 729 |
| Lys | Gly | Tyr | Val | Pro | Pro | Thr | Gly | Lys | Ser | Phe | Ala | Ile | Asn | Phe | Lys | |
| | | | 215 | | | | | 220 | | | | | 225 | | | |
| gtg | ggc | tcc | tca | ggg | gac | ata | gct | ctg | cac | att | aat | ccc | cgc | atg | ggc | 777 |
| Val | Gly | Ser | Ser | Gly | Asp | Ile | Ala | Leu | His | Ile | Asn | Pro | Arg | Met | Gly | |
| | | | 230 | | | | | 235 | | | | | 240 | | | |
| aac | ggt | acc | gtg | gtc | cgg | aac | agc | ctt | ctg | aat | ggc | tcg | tgg | gga | tcc | 825 |
| Asn | Gly | Thr | Val | Val | Arg | Asn | Ser | Leu | Leu | Asn | Gly | Ser | Trp | Gly | Ser | |
| | | | 245 | | | | | 250 | | | | | 255 | | | |
| gag | gag | aag | aag | atc | acc | cac | aac | cca | ttt | ggt | ccc | gga | cag | ttc | ttt | 873 |
| Glu | Glu | Lys | Lys | Ile | Thr | His | Asn | Pro | Phe | Gly | Pro | Gly | Gln | Phe | Phe | |
| | 260 | | | | | 265 | | | | | 270 | | | | | |
| gat | ctg | tcc | att | cgc | tgt | ggc | ttg | gat | cgc | ttc | aag | gtt | tac | gcc | aat | 921 |
| Asp | Leu | Ser | Ile | Arg | Cys | Gly | Leu | Asp | Arg | Phe | Lys | Val | Tyr | Ala | Asn | |
| 275 | | | | | 280 | | | | | 285 | | | | | 290 | |
| ggc | cag | cac | ctc | ttt | gac | ttt | gcc | cat | cgc | ctc | tcg | gcc | ttc | cag | agg | 969 |
| Gly | Gln | His | Leu | Phe | Asp | Phe | Ala | His | Arg | Leu | Ser | Ala | Phe | Gln | Arg | |
| | | | | 295 | | | | | 300 | | | | | 305 | | |
| gtg | gac | aca | ttg | gaa | atc | cag | ggt | gat | gtc | acc | ttg | tcc | tat | gtc | cag | 1017 |
| Val | Asp | Thr | Leu | Glu | Ile | Gln | Gly | Asp | Val | Thr | Leu | Ser | Tyr | Val | Gln | |
| | | | 310 | | | | | 315 | | | | | 320 | | | |
| atc | taatctattc | ctggggccat | aactcatggg | aaaacagaat | tatccccta | | | | | | | | | | | 1070 |
| Ile | | | | | | | | | | | | | | | | |
| gactcctttc | taagccccta | ataaaatgtc | tgagggtgtc | tcatgaaaaa | aaaaaaaaaa | | | | | | | | | | | 1130 |
| aaaaaaaa | | | | | | | | | | | | | | | | 1138 |

<210> SEQ ID NO 2
<211> LENGTH: 323
<212> TYPE: PRT
<213> ORGANISM: Homo sapiens

<400> SEQUENCE: 2

Met Ala Tyr Val Pro Ala Pro Gly Tyr Gln Pro Thr Tyr Asn Pro Thr
1               5                   10                  15

Leu Pro Tyr Tyr Gln Pro Ile Pro Gly Gly Leu Asn Val Gly Met Ser
            20                  25                  30

Val Tyr Ile Gln Gly Val Ala Ser Glu His Met Lys Arg Phe Val
        35                  40                  45

Asn Phe Val Val Gly Gln Asp Pro Gly Ser Asp Val Ala Phe His Phe
    50                  55                  60

Asn Pro Arg Phe Asp Gly Trp Asp Lys Val Val Phe Asn Thr Leu Gln
65                  70                  75                  80

Gly Gly Lys Trp Gly Ser Glu Glu Arg Lys Arg Ser Met Pro Phe Lys
                85                  90                  95

Lys Gly Ala Ala Phe Glu Leu Val Phe Ile Val Leu Ala Glu His Tyr
            100                 105                 110

Lys Val Val Val Asn Gly Asn Pro Phe Tyr Glu Tyr Gly His Arg Leu
        115                 120                 125

Pro Leu Gln Met Val Thr His Leu Gln Val Asp Gly Asp Leu Gln Leu
    130                 135                 140

Gln Ser Ile Asn Phe Ile Gly Gly Gln Pro Leu Arg Pro Gln Gly Pro
145                 150                 155                 160

Pro Met Met Pro Pro Tyr Pro Gly Pro Gly His Cys His Gln Gln Leu
                165                 170                 175

Asn Ser Leu Pro Thr Met Glu Gly Pro Pro Thr Phe Asn Pro Pro Val

-continued

```
                        180                 185                 190
Pro Tyr Phe Gly Arg Leu Gln Gly Gly Leu Thr Ala Arg Arg Thr Ile
            195                 200                 205
Ile Ile Lys Gly Tyr Val Pro Pro Thr Gly Lys Ser Phe Ala Ile Asn
    210                 215                 220
Phe Lys Val Gly Ser Ser Gly Asp Ile Ala Leu His Ile Asn Pro Arg
225                 230                 235                 240
Met Gly Asn Gly Thr Val Val Arg Asn Ser Leu Leu Asn Gly Ser Trp
                245                 250                 255
Gly Ser Glu Glu Lys Lys Ile Thr His Asn Pro Phe Gly Pro Gly Gln
            260                 265                 270
Phe Phe Asp Leu Ser Ile Arg Cys Gly Leu Asp Arg Phe Lys Val Tyr
        275                 280                 285
Ala Asn Gly Gln His Leu Phe Asp Phe Ala His Arg Leu Ser Ala Phe
    290                 295                 300
Gln Arg Val Asp Thr Leu Glu Ile Gln Gly Asp Val Thr Leu Ser Tyr
305                 310                 315                 320
Val Gln Ile
```

<210> SEQ ID NO 3
<211> LENGTH: 1545
<212> TYPE: DNA
<213> ORGANISM: Homo sapiens
<220> FEATURE:
<221> NAME/KEY: CDS
<222> LOCATION: (16)..(948)

<400> SEQUENCE: 3

```
agaggcggcg gagag atg gcc ttc agc ggt tcc cag gct ccc tac ctg agt        51
                Met Ala Phe Ser Gly Ser Gln Ala Pro Tyr Leu Ser
                1               5                   10 cca gct gtc ccc ttt tct ggg act att caa gga ggt ctc cag gac gga        99
Pro Ala Val Pro Phe Ser Gly Thr Ile Gln Gly Gly Leu Gln Asp Gly
        15                  20                  25 ctt cag atc act gtc aat ggg acc gtt ctc agc tcc agt gga acc agg        147
Leu Gln Ile Thr Val Asn Gly Thr Val Leu Ser Ser Ser Gly Thr Arg
    30                  35                  40 ttt gct gtg aac ttt cag act ggc ttc agt gga aat gac att gcc ttc        195
Phe Ala Val Asn Phe Gln Thr Gly Phe Ser Gly Asn Asp Ile Ala Phe
45                  50                  55                  60 cac ttc aac cct cgg ttt gaa gat gga ggg tac gtg gtg tgc aac acg        243
His Phe Asn Pro Arg Phe Glu Asp Gly Gly Tyr Val Val Cys Asn Thr
                65                  70                  75 agg cag aac gga agc tgg ggg ccc gag gag agg aag aca cac atg cct        291
Arg Gln Asn Gly Ser Trp Gly Pro Glu Glu Arg Lys Thr His Met Pro
            80                  85                  90 ttc cag aag ggg atg ccc ttt gac ctc tgc ttc ctg gtg cag agc tca        339
Phe Gln Lys Gly Met Pro Phe Asp Leu Cys Phe Leu Val Gln Ser Ser
        95                  100                 105 gat ttc aag gtg atg gtg aac ggg atc ctc ttc gtg cag tac ttc cac        387
Asp Phe Lys Val Met Val Asn Gly Ile Leu Phe Val Gln Tyr Phe His
    110                 115                 120 cgc gtg ccc ttc cac cgt gtg gac acc atc tcc gtc aat ggc tct gtg        435
Arg Val Pro Phe His Arg Val Asp Thr Ile Ser Val Asn Gly Ser Val
125                 130                 135                 140 cag ctg tcc tac atc agc ttc cag acc cag aca gtc atc cac aca gtg        483
Gln Leu Ser Tyr Ile Ser Phe Gln Thr Gln Thr Val Ile His Thr Val
                145                 150                 155
```

```
cag agc gcc cct gga cag atg ttc tct act ccc gcc atc cca cct atg    531
Gln Ser Ala Pro Gly Gln Met Phe Ser Thr Pro Ala Ile Pro Pro Met
        160                 165                 170 atg tac ccc cac ccc gcc tat ccg atg cct ttc atc acc acc att ctg    579
Met Tyr Pro His Pro Ala Tyr Pro Met Pro Phe Ile Thr Thr Ile Leu
            175                 180                 185 gga ggg ctg tac cca tcc aag tcc atc ctc ctg tca ggc act gtc ctg    627
Gly Gly Leu Tyr Pro Ser Lys Ser Ile Leu Leu Ser Gly Thr Val Leu
    190                 195                 200 ccc agt gct cag agg ttc cac atc aac ctg tgc tct ggg aac cac atc    675
Pro Ser Ala Gln Arg Phe His Ile Asn Leu Cys Ser Gly Asn His Ile
205                 210                 215                 220 gcc ttc cac ctg aac ccc cgt ttt gat gag aat gct gtg gtc cgc aac    723
Ala Phe His Leu Asn Pro Arg Phe Asp Glu Asn Ala Val Val Arg Asn
                225                 230                 235 acc cag atc gac aac tcc tgg ggg tct gag gag cga agt ctg ccc cga    771
Thr Gln Ile Asp Asn Ser Trp Gly Ser Glu Glu Arg Ser Leu Pro Arg
            240                 245                 250 aaa atg ccc ttc gtc cgt ggc cag agc ttc tca gtg tgg atc ttg tgt    819
Lys Met Pro Phe Val Arg Gly Gln Ser Phe Ser Val Trp Ile Leu Cys
    255                 260                 265 gaa gct cac tgc ctc aag gtg gcc gtg gat ggt cag cac ctg ttt gaa    867
Glu Ala His Cys Leu Lys Val Ala Val Asp Gly Gln His Leu Phe Glu
270                 275                 280 tac tac cat cgc ctg agg aac ctg ccc acc atc aac aga ctg gaa gtg    915
Tyr Tyr His Arg Leu Arg Asn Leu Pro Thr Ile Asn Arg Leu Glu Val
285                 290                 295                 300 ggg ggc gac atc cag ctg acc cat gtg cag aca taggcggctt cctggccctg   968
Gly Gly Asp Ile Gln Leu Thr His Val Gln Thr
                305                 310 gggccggggg ctgggtgtg gggcagtctg ggtcctctca tcatcccac ttcccaggcc    1028 cagcctttcc aaccctgcct gggatctggg ctttaatgca gaggccatgt ccttgtctgg   1088
tcctgcttct ggctacagcc accctggaac ggagaaggca gctgacgggg attgccttcc   1148
tcagccgcag cagcacctgg ggctccagct gctggaaatc ctaccatccc aggaggcagg   1208
cacagccagg gagaggggag gagtgggcag tgaagatgaa gccccatgct cagtcccctc   1268
ccatccccca cgcagctcca ccccagtccc aagccaccag ctgtctgctc ctggtgggag   1328
gtggcctcct cagcccctcc tctctgacct ttaacctcac tctcaccttg caccgtgcac   1388
caacccttca cccctcctgg aaagcaggcc tgatggcttc ccactggcct ccaccacctg   1448
accagagtgt tctcttcaga ggactggctc ctttcccagt gtccttaaaa taagaaatg   1508 aaaatgcttg ttggcaaaaa aaaaaaaaaa aaaaaaa                           1545

<210> SEQ ID NO 4
<211> LENGTH: 311
<212> TYPE: PRT
<213> ORGANISM: Homo sapiens

<400> SEQUENCE: 4

Met Ala Phe Ser Gly Ser Gln Ala Pro Tyr Leu Ser Pro Ala Val Pro
1               5                   10                  15

Phe Ser Gly Thr Ile Gln Gly Gly Leu Gln Asp Gly Leu Gln Ile Thr
            20                  25                  30

Val Asn Gly Thr Val Leu Ser Ser Gly Thr Arg Phe Ala Val Asn
        35                  40                  45

Phe Gln Thr Gly Phe Ser Gly Asn Asp Ile Ala Phe His Phe Asn Pro
    50                  55                  60
```

```
Arg Phe Glu Asp Gly Gly Tyr Val Val Cys Asn Thr Arg Gln Asn Gly
 65                  70                  75                  80

Ser Trp Gly Pro Glu Glu Arg Lys Thr His Met Pro Phe Gln Lys Gly
                 85                  90                  95

Met Pro Phe Asp Leu Cys Phe Leu Val Gln Ser Ser Asp Phe Lys Val
            100                 105                 110

Met Val Asn Gly Ile Leu Phe Val Gln Tyr Phe His Arg Val Pro Phe
        115                 120                 125

His Arg Val Asp Thr Ile Ser Val Asn Gly Ser Val Gln Leu Ser Tyr
    130                 135                 140

Ile Ser Phe Gln Thr Gln Thr Val Ile His Thr Val Gln Ser Ala Pro
145                 150                 155                 160

Gly Gln Met Phe Ser Thr Pro Ala Ile Pro Pro Met Met Tyr Pro His
                165                 170                 175

Pro Ala Tyr Pro Met Pro Phe Ile Thr Thr Ile Leu Gly Gly Leu Tyr
            180                 185                 190

Pro Ser Lys Ser Ile Leu Leu Ser Gly Thr Val Leu Pro Ser Ala Gln
        195                 200                 205

Arg Phe His Ile Asn Leu Cys Ser Gly Asn His Ile Ala Phe His Leu
    210                 215                 220

Asn Pro Arg Phe Asp Glu Asn Ala Val Val Arg Asn Thr Gln Ile Asp
225                 230                 235                 240

Asn Ser Trp Gly Ser Glu Glu Arg Ser Leu Pro Arg Lys Met Pro Phe
                245                 250                 255

Val Arg Gly Gln Ser Phe Ser Val Trp Ile Leu Cys Glu Ala His Cys
            260                 265                 270

Leu Lys Val Ala Val Asp Gly Gln His Leu Phe Glu Tyr Tyr His Arg
        275                 280                 285

Leu Arg Asn Leu Pro Thr Ile Asn Arg Leu Glu Val Gly Gly Asp Ile
    290                 295                 300

Gln Leu Thr His Val Gln Thr
305                 310

<210> SEQ ID NO 5
<211> LENGTH: 1479
<212> TYPE: DNA
<213> ORGANISM: Homo sapiens
<220> FEATURE:
<221> NAME/KEY: CDS
<222> LOCATION: (118)..(1068)

<400> SEQUENCE: 5
acaccagtct ttggggccag tgcctcagtt tcaatccagg taacctttaa atgaaacttg      60
cctaaaatct taggtcatac acagaagaga ctccaatcga caagaagctg gaaaaga      117 atg atg ttg tcc tta aac aac cta cag aat atc atc tat aac ccg gta      165
Met Met Leu Ser Leu Asn Asn Leu Gln Asn Ile Ile Tyr Asn Pro Val
 1               5                  10                  15 atc ccg ttt gtt ggc acc att cct gat cag ctg gat cct gga act ttg      213
Ile Pro Phe Val Gly Thr Ile Pro Asp Gln Leu Asp Pro Gly Thr Leu
             20                  25                  30 att gtg ata cgt ggg cat gtt cct agt gac gca gac aga ttc cag gtg      261
Ile Val Ile Arg Gly His Val Pro Ser Asp Ala Asp Arg Phe Gln Val
         35                  40                  45 gat ctg cag aat ggc agc agt gtg aaa cct cga gcc gat gtg gcc ttt      309
Asp Leu Gln Asn Gly Ser Ser Val Lys Pro Arg Ala Asp Val Ala Phe
     50                  55                  60
```

```
cat ttc aat cct cgt ttc aaa agg gcc ggc tgc att gtt tgc aat act      357
His Phe Asn Pro Arg Phe Lys Arg Ala Gly Cys Ile Val Cys Asn Thr
 65                  70                  75                  80 ttg ata aat gaa aaa tgg gga cgg gaa gag atc acc tat gac acg cct      405
Leu Ile Asn Glu Lys Trp Gly Arg Glu Glu Ile Thr Tyr Asp Thr Pro
                 85                  90                  95 ttc aaa aga gaa aag tct ttt gag atc gtg att atg gtg cta aag gac      453
Phe Lys Arg Glu Lys Ser Phe Glu Ile Val Ile Met Val Leu Lys Asp
            100                 105                 110 aaa ttc cag gtg gct gta aat gga aaa cat act ctg ctc tat ggc cac      501
Lys Phe Gln Val Ala Val Asn Gly Lys His Thr Leu Leu Tyr Gly His
        115                 120                 125 agg atc ggc cca gag aaa ata gac act ctg ggc att tat ggc aaa gtg      549
Arg Ile Gly Pro Glu Lys Ile Asp Thr Leu Gly Ile Tyr Gly Lys Val
    130                 135                 140 aat att cac tca att ggt ttt agc ttc agc tcg gac tta caa agt acc      597
Asn Ile His Ser Ile Gly Phe Ser Phe Ser Ser Asp Leu Gln Ser Thr
145                 150                 155                 160 caa gca tct agt ctg gaa ctg aca gag ata gtt aga gaa aat gtt cca      645
Gln Ala Ser Ser Leu Glu Leu Thr Glu Ile Val Arg Glu Asn Val Pro
                165                 170                 175 aag tct ggc acg ccc cag ctt agc ctg cca ttc gct gca agg ttg aac      693
Lys Ser Gly Thr Pro Gln Leu Ser Leu Pro Phe Ala Ala Arg Leu Asn
            180                 185                 190 acc ccc atg ggc cct gga cga act gtc gtc gtt aaa gga gaa gtg aat      741
Thr Pro Met Gly Pro Gly Arg Thr Val Val Val Lys Gly Glu Val Asn
        195                 200                 205 gca aat gcc aaa agc ttt aat gtt gac cta cta gca gga aaa tca aag      789
Ala Asn Ala Lys Ser Phe Asn Val Asp Leu Leu Ala Gly Lys Ser Lys
    210                 215                 220 gat att gct cta cac ttg aac cca cgc ctg aat att aaa gca ttt gtg      837
Asp Ile Ala Leu His Leu Asn Pro Arg Leu Asn Ile Lys Ala Phe Val
225                 230                 235                 240 aga aat tct ttt ctt caa gag tcc tgg gga gaa gaa gag aga aat att      885
Arg Asn Ser Phe Leu Gln Glu Ser Trp Gly Glu Glu Glu Arg Asn Ile
                245                 250                 255 acc gct ttc cca ttt agt cct ggg atg tac ttt gag atg ata att tat      933
Thr Ala Phe Pro Phe Ser Pro Gly Met Tyr Phe Glu Met Ile Ile Tyr
            260                 265                 270 tgt gat gtt aga gaa ttc aag gtt gca gta aat ggc gta cac agc ctg      981
Cys Asp Val Arg Glu Phe Lys Val Ala Val Asn Gly Val His Ser Leu
        275                 280                 285 gag tac aaa cac aga ttt aaa gag ctc agc agt att gac acg ctg gaa     1029
Glu Tyr Lys His Arg Phe Lys Glu Leu Ser Ser Ile Asp Thr Leu Glu
    290                 295                 300 att aat gga gac atc cac tta ctg gaa gta agg agc tgg tagcctacct     1078
Ile Asn Gly Asp Ile His Leu Leu Glu Val Arg Ser Trp
305                 310                 315 acacagctgc tacaaaaacc aaaatacaga atggcttctg tgatactggc cttgctgaaa   1138
cgcatctcac tgtcattcta ttgtttatat tgttaaaatg agcttgtgca ccattaggtc   1198
ctgctgggtg ttctcagtcc ttgccatgaa gtatggtggt gtctagcact gaatggggaa   1258
actgggggca gcaacactta tagccagtta aagccactct gccctctctc ctactttggc   1318
tgactcttca agaatgccat tcaacaagta tttatggagt cctactatat acagtagcta   1378
acatgtattg agcacagatt tttttggtaa acctgtgagg gctagggtat atccttggga   1438
acaaaccaga atgtcctgtc ccttgaaaaa aaaaaaaaaa a                       1479
```

```
<210> SEQ ID NO 6
<211> LENGTH: 317
<212> TYPE: PRT
<213> ORGANISM: Homo sapiens

<400> SEQUENCE: 6

Met Met Leu Ser Leu Asn Asn Leu Gln Asn Ile Ile Tyr Asn Pro Val
1               5                   10                  15

Ile Pro Phe Val Gly Thr Ile Pro Asp Gln Leu Asp Pro Gly Thr Leu
            20                  25                  30

Ile Val Ile Arg Gly His Val Pro Ser Asp Ala Asp Arg Phe Gln Val
        35                  40                  45

Asp Leu Gln Asn Gly Ser Ser Val Lys Pro Arg Ala Asp Val Ala Phe
    50                  55                  60

His Phe Asn Pro Arg Phe Lys Arg Ala Gly Cys Ile Val Cys Asn Thr
65                  70                  75                  80

Leu Ile Asn Glu Lys Trp Gly Arg Glu Glu Ile Thr Tyr Asp Thr Pro
                85                  90                  95

Phe Lys Arg Glu Lys Ser Phe Glu Ile Val Ile Met Val Leu Lys Asp
            100                 105                 110

Lys Phe Gln Val Ala Val Asn Gly Lys His Thr Leu Leu Tyr Gly His
        115                 120                 125

Arg Ile Gly Pro Glu Lys Ile Asp Thr Leu Gly Ile Tyr Gly Lys Val
    130                 135                 140

Asn Ile His Ser Ile Gly Phe Ser Phe Ser Ser Asp Leu Gln Ser Thr
145                 150                 155                 160

Gln Ala Ser Ser Leu Glu Leu Thr Glu Ile Val Arg Glu Asn Val Pro
                165                 170                 175

Lys Ser Gly Thr Pro Gln Leu Ser Leu Pro Phe Ala Ala Arg Leu Asn
            180                 185                 190

Thr Pro Met Gly Pro Gly Arg Thr Val Val Lys Gly Glu Val Asn
            195                 200                 205

Ala Asn Ala Lys Ser Phe Asn Val Asp Leu Leu Ala Gly Lys Ser Lys
    210                 215                 220

Asp Ile Ala Leu His Leu Asn Pro Arg Leu Asn Ile Lys Ala Phe Val
225                 230                 235                 240

Arg Asn Ser Phe Leu Gln Glu Ser Trp Gly Glu Glu Arg Asn Ile
                245                 250                 255

Thr Ala Phe Pro Phe Ser Pro Gly Met Tyr Phe Glu Met Ile Ile Tyr
            260                 265                 270

Cys Asp Val Arg Glu Phe Lys Val Ala Val Asn Gly Val His Ser Leu
        275                 280                 285

Glu Tyr Lys His Arg Phe Lys Glu Leu Ser Ser Ile Asp Thr Leu Glu
    290                 295                 300

Ile Asn Gly Asp Ile His Leu Leu Glu Val Arg Ser Trp
305                 310                 315

<210> SEQ ID NO 7
<211> LENGTH: 1936
<212> TYPE: DNA
<213> ORGANISM: Homo sapiens
<220> FEATURE:
<221> NAME/KEY: CDS
<222> LOCATION: (118)..(717)

<400> SEQUENCE: 7
```

-continued

| | |
|---|---|
| acaccagtct ttggggccag tgcctcagtt tcaatccagg taacctttaa atgaaacttg | 60 |
| cctaaaatct taggtcatac acagaagaga ctccaatcga caagaagctg gaaaaga | 117 |

| atg atg ttg tcc tta aac aac cta cag aat atc atc tat aac ccg gta | 165 |
|---|---|
| Met Met Leu Ser Leu Asn Asn Leu Gln Asn Ile Ile Tyr Asn Pro Val | |
| 1 5 10 15 | |

| atc ccg ttt gtt ggc acc att cct gat cag ctg gat cct gga act ttg | 213 |
|---|---|
| Ile Pro Phe Val Gly Thr Ile Pro Asp Gln Leu Asp Pro Gly Thr Leu | |
| 20 25 30 | |

| att gtg ata cgt ggg cat gtt cct agt gac gca gac aga ttc cag gtg | 261 |
|---|---|
| Ile Val Ile Arg Gly His Val Pro Ser Asp Ala Asp Arg Phe Gln Val | |
| 35 40 45 | |

| gat ctg cag aat ggc agc agc atg aaa cct cga gcc gat gtg gcc ttt | 309 |
|---|---|
| Asp Leu Gln Asn Gly Ser Ser Met Lys Pro Arg Ala Asp Val Ala Phe | |
| 50 55 60 | |

| cat ttc aat cct cgt ttc aaa agg gcc ggc tgc att gtt tgc aat act | 357 |
|---|---|
| His Phe Asn Pro Arg Phe Lys Arg Ala Gly Cys Ile Val Cys Asn Thr | |
| 65 70 75 80 | |

| ttg ata aat gaa aaa tgg gga cgg gaa gag atc acc tat gac acg cct | 405 |
|---|---|
| Leu Ile Asn Glu Lys Trp Gly Arg Glu Glu Ile Thr Tyr Asp Thr Pro | |
| 85 90 95 | |

| ttc aaa aga gaa aag tct ttt gag atc gtg att atg gtg ctg aag gac | 453 |
|---|---|
| Phe Lys Arg Glu Lys Ser Phe Glu Ile Val Ile Met Val Leu Lys Asp | |
| 100 105 110 | |

| aaa ttc cag gtg gct gta aat gga aaa cat act ctg ctc tat ggc cac | 501 |
|---|---|
| Lys Phe Gln Val Ala Val Asn Gly Lys His Thr Leu Leu Tyr Gly His | |
| 115 120 125 | |

| agg atc ggc cca gag aaa ata gac act ctg ggc att tat ggc aaa gtg | 549 |
|---|---|
| Arg Ile Gly Pro Glu Lys Ile Asp Thr Leu Gly Ile Tyr Gly Lys Val | |
| 130 135 140 | |

| aat att cac tca att ggt ttt agc ttc agc tcg gac tta caa agt acc | 597 |
|---|---|
| Asn Ile His Ser Ile Gly Phe Ser Phe Ser Ser Asp Leu Gln Ser Thr | |
| 145 150 155 160 | |

| caa gca tct agt ctg gaa ctg aca gag ata agt aga gaa aat gtt cca | 645 |
|---|---|
| Gln Ala Ser Ser Leu Glu Leu Thr Glu Ile Ser Arg Glu Asn Val Pro | |
| 165 170 175 | |

| aag tct ggc acg ccc cag ctt gtg agt att ttt gcc tgg gtt att tca | 693 |
|---|---|
| Lys Ser Gly Thr Pro Gln Leu Val Ser Ile Phe Ala Trp Val Ile Ser | |
| 180 185 190 | |

| tgt gga ata ttt tat aaa gtt gca tagaaaatga acagtttaaa ccgtggaggg | 747 |
|---|---|
| Cys Gly Ile Phe Tyr Lys Val Ala | |
| 195 200 | |

| | |
|---|---|
| cagcttcatt cattccattc cttactgtag aactgtttcc ctacagccta gtaatagagg | 807 |
| aggagacatt tctaaaatcg cacccagaac tgtctcacacc aagagcaaag attcgactgt | 867 |
| caatcacact ttgacttgca ccaaaatacc acctatgaac tatgtgtcaa agggtttgaa | 927 |
| gagcaccaaa ttttcttaac tctatataaa aattaagttg taatgagctg ttacgagtaa | 987 |
| cctgtatcca caatagaggc ccaaagcagc ccctctgca tttgtgtgcc gtccctggac | 1047 |
| ggattcgaga gtcaaccagg cctgcctctg agccatttct gtgtatttcc tcagcacctc | 1107 |
| cctgcttggc tgcttcccct tcaggcagaa cacagtactg cctcagaccc caggcacagg | 1167 |
| gggccttcct ggcgtgtttc actcatacag agggcatcgg gtcccaccct gtcactcatt | 1227 |
| tcatcgtcta aaatgtaatc atgtgtgttt gcttcgagcc agggacagtg ctgctgcagg | 1287 |
| ggacccagct gggaccaagg cagactgtct ctcccctcct gggatttaca gggtcatggc | 1347 |
| tctgaaacat tccgtagtgt tctttggaca cgagttttcc ctggagatcg ctttctgcag | 1407 |
| gctcttggtc ctgactgtgg cttcttttca gaggctgcca tttcgctgca aggttgaaca | 1467 |

```
ccccccatggg ccctggacga actgtcgtcg ttaaaggaga agtgaatgca aatgccaaaa    1527
gctttaatgt tgacctacta gcaggaaaat caaaggatat tgctctacac ttgaacccac    1587
gcctgaatat taaagcattt gtaagaaatt cttttcttca ggagtcctgg ggagaagaag    1647
agagaaatat tacctctttc ccatttagtc ctgggatgta ctttgagatg ataatttatt    1707
gtgatgttag agaattcaag gttgcagtaa atggcgtaca cagcctggag tacaaacaca    1767
gatttaaaga gctcagcagt attgacacgc tggaaattaa tggagacatc cacttactgg    1827
aagtaaggag ctggtagcct acctacacag ctgctacaaa aaccaaaata cagaatggct    1887
tctgtgatac tggccttgct gaaacgcaaa aaaaaaaaaa aaaaaaaa              1936
```

<210> SEQ ID NO 8
<211> LENGTH: 200
<212> TYPE: PRT
<213> ORGANISM: Homo sapiens

<400> SEQUENCE: 8

```
Met Met Leu Ser Leu Asn Asn Leu Gln Asn Ile Ile Tyr Asn Pro Val
 1               5                   10                  15

Ile Pro Phe Val Gly Thr Ile Pro Asp Gln Leu Asp Pro Gly Thr Leu
             20                  25                  30

Ile Val Ile Arg Gly His Val Pro Ser Asp Ala Asp Arg Phe Gln Val
         35                  40                  45

Asp Leu Gln Asn Gly Ser Ser Met Lys Pro Arg Ala Asp Val Ala Phe
     50                  55                  60

His Phe Asn Pro Arg Phe Lys Arg Ala Gly Cys Ile Val Cys Asn Thr
 65                  70                  75                  80

Leu Ile Asn Glu Lys Trp Gly Arg Glu Glu Ile Thr Tyr Asp Thr Pro
                 85                  90                  95

Phe Lys Arg Glu Lys Ser Phe Glu Ile Val Ile Met Val Leu Lys Asp
            100                 105                 110

Lys Phe Gln Val Ala Val Asn Gly Lys His Thr Leu Leu Tyr Gly His
        115                 120                 125

Arg Ile Gly Pro Glu Lys Ile Asp Thr Leu Gly Ile Tyr Gly Lys Val
    130                 135                 140

Asn Ile His Ser Ile Gly Phe Ser Phe Ser Ser Asp Leu Gln Ser Thr
145                 150                 155                 160

Gln Ala Ser Ser Leu Glu Leu Thr Glu Ile Ser Arg Glu Asn Val Pro
                165                 170                 175

Lys Ser Gly Thr Pro Gln Leu Val Ser Ile Phe Ala Trp Val Ile Ser
            180                 185                 190

Cys Gly Ile Phe Tyr Lys Val Ala
        195                 200
```

<210> SEQ ID NO 9
<211> LENGTH: 132
<212> TYPE: PRT
<213> ORGANISM: Homo sapiens

<400> SEQUENCE: 9

```
Met Thr Gly Glu Leu Glu Val Lys Asn Met Asp Met Lys Pro Gly Ser
 1               5                   10                  15

Thr Leu Lys Ile Thr Gly Ser Ile Ala Asp Gly Thr Asp Gly Phe Val
             20                  25                  30

Ile Asn Leu Gly Gln Gly Thr Asp Lys Leu Asn Leu His Phe Asn Pro
```

-continued

```
                 35                  40                  45
Arg Phe Ser Glu Ser Thr Ile Val Cys Asn Ser Leu Asp Gly Ser Asn
         50                  55                  60

Trp Gly Gln Glu Gln Arg Glu Asp His Leu Cys Phe Ser Pro Gly Ser
 65                  70                  75                  80

Glu Val Lys Phe Thr Val Thr Phe Glu Ser Asp Lys Phe Lys Val Lys
                 85                  90                  95

Leu Pro Asp Gly His Glu Leu Thr Phe Pro Asn Arg Leu Gly His Ser
            100                 105                 110

His Leu Ser Tyr Leu Ser Val Arg Gly Gly Phe Asn Met Ser Ser Phe
        115                 120                 125

Lys Leu Lys Glu
    130

<210> SEQ ID NO 10
<211> LENGTH: 250
<212> TYPE: PRT
<213> ORGANISM: Homo sapiens

<400> SEQUENCE: 10

Met Ala Asp Asn Phe Ser Leu His Asp Ala Leu Ser Gly Ser Gly Asn
 1               5                  10                  15

Pro Asn Pro Gln Gly Trp Pro Gly Ala Trp Gly Asn Gln Pro Ala Gly
             20                  25                  30

Ala Gly Gly Tyr Pro Gly Ala Ser Tyr Pro Gly Ala Tyr Pro Gly Gln
         35                  40                  45

Ala Pro Pro Gly Ala Tyr Pro Gly Gln Ala Pro Pro Gly Ala Tyr His
     50                  55                  60

Gly Ala Pro Gly Ala Tyr Pro Gly Ala Pro Ala Pro Gly Val Tyr Pro
 65                  70                  75                  80

Gly Pro Pro Ser Gly Pro Gly Ala Tyr Pro Ser Ser Gly Gln Pro Ser
                 85                  90                  95

Ala Pro Gly Ala Tyr Pro Ala Thr Gly Pro Tyr Gly Ala Pro Ala Gly
            100                 105                 110

Pro Leu Ile Val Pro Tyr Asn Leu Pro Leu Pro Gly Gly Val Val Pro
        115                 120                 125

Arg Met Leu Ile Thr Ile Leu Gly Thr Val Lys Pro Asn Ala Asn Arg
    130                 135                 140

Ile Ala Leu Asp Phe Gln Arg Gly Asn Asp Val Ala Phe His Phe Asn
145                 150                 155                 160

Pro Arg Phe Asn Glu Asn Asn Arg Arg Val Ile Val Cys Asn Thr Lys
                165                 170                 175

Leu Asp Asn Asn Trp Gly Arg Glu Glu Arg Gln Ser Val Phe Pro Phe
            180                 185                 190

Glu Ser Gly Lys Pro Phe Lys Ile Gln Val Leu Val Glu Pro Asp His
        195                 200                 205

Phe Lys Val Ala Val Asn Asp Ala His Leu Leu Gln Tyr Asn His Arg
    210                 215                 220

Val Lys Lys Leu Asn Glu Ile Ser Lys Leu Gly Ile Ser Gly Asp Ile
225                 230                 235                 240

Asp Leu Thr Ser Ala Ser Tyr Thr Met Ile
                245                 250

<210> SEQ ID NO 11
<211> LENGTH: 324
```

```
<212> TYPE: PRT
<213> ORGANISM: Rat

<400> SEQUENCE: 11

Met Ala Tyr Val Pro Ala Pro Gly Tyr Gln Pro Thr Tyr Asn Pro Thr
1               5                   10                  15

Leu Pro Tyr Lys Arg Pro Ile Pro Gly Gly Leu Ser Val Gly Met Ser
            20                  25                  30

Ile Tyr Ile Gln Gly Ile Ala Lys Asp Asn Met Arg Arg Phe His Val
        35                  40                  45

Asn Phe Ala Val Gly Gln Asp Glu Gly Ala Asp Ile Ala Phe His Phe
    50                  55                  60

Asn Pro Arg Phe Asp Gly Trp Asp Lys Val Val Phe Asn Thr Met Gln
65                  70                  75                  80

Ser Gly Gln Trp Gly Lys Glu Glu Lys Lys Ser Met Pro Phe Gln
                85                  90                  95

Lys Gly His His Phe Glu Leu Val Phe Met Val Met Ser Glu His Tyr
                100                 105                 110

Lys Val Val Val Asn Gly Thr Pro Phe Tyr Glu Tyr Gly His Arg Leu
            115                 120                 125

Pro Leu Gln Met Val Thr His Leu Gln Val Asp Gly Asp Leu Glu Leu
130                 135                 140

Gln Ser Ile Asn Phe Leu Gly Gly Gln Pro Ala Ala Ser Gln Tyr Pro
145                 150                 155                 160

Gly Thr Met Thr Ile Pro Ala Tyr Pro Ser Ala Gly Tyr Asn Pro Pro
                165                 170                 175

Gln Met Asn Ser Leu Pro Val Met Ala Gly Pro Pro Ile Phe Asn Pro
            180                 185                 190

Pro Val Pro Tyr Val Gly Thr Leu Gln Gly Gly Leu Thr Ala Arg Arg
            195                 200                 205

Thr Ile Ile Ile Lys Gly Tyr Val Leu Pro Thr Ala Lys Asn Leu Ile
210                 215                 220

Ile Asn Phe Lys Val Gly Ser Thr Gly Asp Ile Ala Phe His Met Asn
225                 230                 235                 240

Pro Arg Ile Gly Asp Cys Val Val Arg Asn Ser Tyr Met Asn Gly Ser
                245                 250                 255

Trp Gly Ser Glu Glu Arg Lys Ile Pro Tyr Asn Pro Phe Gly Ala Gly
            260                 265                 270

Gln Phe Phe Asp Leu Ser Ile Arg Cys Gly Thr Asp Arg Phe Lys Val
        275                 280                 285

Phe Ala Asn Gly Gln His Leu Phe Asp Phe Ser His Arg Phe Gln Ala
    290                 295                 300

Phe Gln Arg Val Asp Met Leu Glu Ile Lys Gly Asp Ile Thr Leu Ser
305                 310                 315                 320

Tyr Val Gln Ile

<210> SEQ ID NO 12
<211> LENGTH: 145
<212> TYPE: PRT
<213> ORGANISM: Rat

<400> SEQUENCE: 12

Met Ser Ser Phe Ser Thr Gln Thr Pro Tyr Pro Asn Leu Ala Val Pro
1               5                   10                  15

Phe Phe Thr Ser Ile Pro Asn Gly Leu Tyr Pro Ser Lys Ser Ile Val
```

-continued

```
                 20                  25                  30
Ile Ser Gly Val Val Leu Ser Asp Ala Lys Arg Phe Gln Ile Asn Leu
         35                  40                  45

Arg Cys Gly Gly Asp Ile Ala Phe His Leu Asn Pro Arg Phe Asp Glu
 50                  55                  60

Asn Ala Val Val Arg Asn Thr Gln Ile Asn Asn Ser Trp Gly Pro Glu
 65                  70                  75                  80

Glu Arg Ser Leu Pro Gly Ser Met Pro Phe Ser Arg Gly Gln Arg Phe
                 85                  90                  95

Ser Val Trp Ile Leu Cys Glu Gly His Cys Phe Lys Val Ala Val Asp
                100                 105                 110

Gly Gln His Ile Cys Glu Tyr Ser His Arg Leu Met Asn Leu Pro Asp
                115                 120                 125

Ile Asn Thr Leu Glu Val Ala Gly Asp Ile Gln Leu Thr His Val Glu
        130                 135                 140

Thr
145

<210> SEQ ID NO 13
<211> LENGTH: 136
<212> TYPE: PRT
<213> ORGANISM: Homo sapiens

<400> SEQUENCE: 13

Met Ser Asn Val Pro His Lys Ser Ser Leu Pro Glu Gly Ile Arg Pro
 1               5                  10                  15

Gly Thr Val Leu Arg Ile Arg Gly Leu Val Pro Pro Asn Ala Ser Arg
                 20                  25                  30

Phe His Val Asn Leu Leu Cys Gly Glu Glu Gln Gly Ser Asp Ala Ala
                 35                  40                  45

Leu His Phe Asn Pro Arg Leu Asp Thr Ser Glu Val Val Phe Asn Ser
        50                  55                  60

Lys Glu Gln Gly Ser Trp Gly Arg Glu Glu Arg Gly Pro Gly Val Pro
 65                  70                  75                  80

Phe Gln Arg Gly Gln Pro Phe Glu Val Leu Ile Ile Ala Ser Asp Asp
                 85                  90                  95

Gly Phe Lys Ala Val Val Gly Asp Ala Gln Tyr His His Phe Arg His
                100                 105                 110

Arg Leu Pro Leu Ala Arg Val Arg Leu Val Glu Val Gly Gly Asp Val
        115                 120                 125

Gln Leu Asp Ser Val Arg Ile Phe
        130                 135

<210> SEQ ID NO 14
<211> LENGTH: 262
<212> TYPE: PRT
<213> ORGANISM: Rat

<400> SEQUENCE: 14

Met Ala Asp Gly Phe Ser Leu Asn Asp Ala Leu Ala Gly Ser Gly Asn
 1               5                  10                  15

Pro Asn Pro Gln Gly Trp Pro Gly Ala Trp Gly Asn Gln Pro Gly Ala
                 20                  25                  30

Gly Gly Tyr Pro Gly Ala Ser Tyr Pro Gly Ala Tyr Pro Gly Gln Ala
         35                  40                  45

Pro Pro Gly Gly Tyr Pro Gly Gln Ala Pro Pro Ser Ala Tyr Pro Gly
```

```
            50                  55                  60
Pro Thr Gly Pro Ser Ala Tyr Pro Gly Pro Thr Ala Pro Gly Ala Tyr
65                  70                  75                  80

Pro Gly Pro Thr Ala Pro Gly Ala Phe Pro Gly Gln Pro Gly Gly Pro
                85                  90                  95

Gly Ala Tyr Pro Ser Ala Pro Gly Ala Tyr Pro Ser Ala Pro Gly Ala
            100                 105                 110

Tyr Pro Ala Thr Gly Pro Phe Gly Ala Pro Thr Gly Pro Leu Thr Val
            115                 120                 125

Pro Tyr Asp Met Pro Leu Pro Gly Gly Val Met Pro Arg Met Leu Ile
130                 135                 140

Thr Ile Ile Gly Thr Val Lys Pro Asn Ala Asn Ser Ile Thr Leu Asn
145                 150                 155                 160

Phe Lys Lys Gly Asn Asp Ile Ala Phe His Phe Asn Pro Arg Phe Asn
                165                 170                 175

Glu Asn Asn Arg Arg Val Ile Val Cys Asn Thr Lys Gln Asp Asn Asn
                180                 185                 190

Trp Gly Arg Glu Glu Arg Gln Ser Ala Phe Pro Phe Glu Ser Gly Lys
                195                 200                 205

Pro Phe Lys Ile Gln Val Leu Val Glu Ala Asp His Phe Lys Val Ala
210                 215                 220

Val Asn Asp Val His Leu Leu Gln Tyr Asn His Arg Met Lys Asn Leu
225                 230                 235                 240

Arg Glu Ile Ser Gln Leu Gly Ile Ile Gly Asp Ile Thr Leu Thr Ser
                245                 250                 255

Ala Ser His Ala Met Ile
            260

<210> SEQ ID NO 15
<211> LENGTH: 316
<212> TYPE: PRT
<213> ORGANISM: Rat

<400> SEQUENCE: 15

Met Leu Ser Leu Ser Asn Leu Gln Asn Ile Ile Tyr Asn Pro Thr Ile
1               5                   10                  15

Pro Tyr Val Ser Thr Ile Thr Glu Gln Leu Lys Pro Gly Ser Leu Ile
                20                  25                  30

Val Ile Arg Gly His Val Pro Lys Asp Ser Glu Arg Phe Gln Val Asp
            35                  40                  45

Phe Gln His Gly Asn Ser Leu Lys Pro Arg Ala Asp Val Ala Phe His
50                  55                  60

Phe Asn Pro Arg Phe Lys Arg Ser Asn Cys Ile Val Cys Asn Thr Leu
65                  70                  75                  80

Thr Asn Glu Lys Trp Gly Trp Glu Glu Ile Thr His Asp Met Pro Phe
                85                  90                  95

Arg Lys Glu Lys Ser Phe Glu Ile Val Ile Met Val Leu Lys Asn Lys
            100                 105                 110

Phe His Val Ala Val Asn Gly Lys His Ile Leu Leu Tyr Ala His Arg
        115                 120                 125

Ile Asn Pro Glu Lys Ile Asp Thr Leu Gly Ile Phe Gly Lys Val Asn
        130                 135                 140

Ile His Ser Ile Gly Phe Arg Phe Ser Ser Asp Leu Gln Ser Met Glu
145                 150                 155                 160
```

```
Thr Ser Thr Leu Gly Leu Thr Gln Ile Ser Lys Glu Asn Ile Gln Lys
                165                 170                 175

Ser Gly Lys Leu His Leu Ser Leu Pro Phe Glu Ala Arg Leu Asn Ala
            180                 185                 190

Ser Met Gly Pro Gly Arg Thr Val Val Lys Gly Glu Val Asn Thr
            195                 200                 205

Asn Ala Thr Ser Phe Asn Val Asp Leu Val Ala Gly Arg Ser Arg Asp
        210                 215                 220

Ile Ala Leu His Leu Asn Pro Arg Leu Asn Val Lys Ala Phe Val Arg
225                 230                 235                 240

Asn Ser Phe Leu Gln Asp Ala Trp Gly Glu Glu Arg Asn Ile Thr
                245                 250                 255

Cys Phe Pro Phe Ser Ser Gly Met Tyr Phe Glu Met Ile Ile Tyr Cys
                260                 265                 270

Asp Val Arg Glu Phe Lys Val Ala Val Asn Gly Val His Ser Leu Glu
            275                 280                 285

Tyr Lys His Arg Phe Lys Asp Leu Ser Ser Ile Asp Thr Leu Ala Val
        290                 295                 300

Asp Gly Asp Ile Arg Leu Leu Asp Val Arg Ser Trp
305                 310                 315

<210> SEQ ID NO 16
<211> LENGTH: 135
<212> TYPE: PRT
<213> ORGANISM: Homo sapiens

<400> SEQUENCE: 16

Met Ala Cys Gly Leu Val Ala Ser Asn Leu Asn Leu Lys Pro Gly Glu
1               5                   10                  15

Cys Leu Arg Val Arg Gly Glu Val Ala Pro Asp Ala Lys Ser Phe Val
            20                  25                  30

Leu Asn Leu Gly Lys Asp Ser Asn Asn Leu Cys Leu His Phe Asn Pro
        35                  40                  45

Arg Phe Asn Ala His Gly Asp Ala Asn Thr Ile Val Cys Asn Ser Lys
    50                  55                  60

Asp Gly Gly Ala Trp Gly Thr Glu Gln Arg Glu Ala Val Phe Pro Phe
65                  70                  75                  80

Gln Pro Gly Ser Val Ala Glu Val Cys Ile Thr Phe Asp Gln Ala Asn
                85                  90                  95

Leu Thr Val Lys Leu Pro Asp Gly Tyr Glu Phe Lys Phe Pro Asn Arg
            100                 105                 110

Leu Asn Leu Glu Ala Ile Asn Tyr Met Ala Ala Asp Gly Asp Phe Lys
        115                 120                 125

Ile Lys Cys Val Ala Phe Asp
    130                 135

<210> SEQ ID NO 17
<211> LENGTH: 316
<212> TYPE: PRT
<213> ORGANISM: Rat

<400> SEQUENCE: 17

Met Leu Ser Leu Ser Asn Leu Gln Asn Ile Ile Tyr Asn Pro Thr Ile
1               5                   10                  15

Pro Tyr Val Ser Thr Ile Thr Glu Gln Leu Lys Pro Gly Ser Leu Ile
            20                  25                  30
```

```
Val Ile Arg Gly His Val Pro Lys Asp Ser Glu Arg Phe Gln Val Asp
         35                  40                  45

Phe Gln His Gly Asn Ser Leu Lys Pro Arg Ala Asp Val Ala Phe His
     50                  55                  60

Phe Asn Pro Arg Phe Lys Arg Ser Asn Cys Ile Val Cys Asn Thr Leu
 65                  70                  75                  80

Thr Asn Glu Lys Trp Gly Trp Glu Glu Ile Thr His Asp Met Pro Phe
                 85                  90                  95

Arg Lys Glu Lys Ser Phe Glu Ile Val Ile Met Val Leu Lys Asn Lys
                100                 105                 110

Phe His Val Ala Val Asn Gly Lys His Ile Leu Leu Tyr Ala His Arg
            115                 120                 125

Ile Asn Pro Glu Lys Ile Asp Thr Leu Gly Ile Phe Gly Lys Val Asn
        130                 135                 140

Ile His Ser Ile Gly Phe Arg Phe Ser Ser Asp Leu Gln Ser Met Glu
145                 150                 155                 160

Thr Ser Thr Leu Gly Leu Thr Gln Ile Ser Lys Glu Asn Ile Gln Lys
                165                 170                 175

Ser Gly Lys Leu His Leu Ser Leu Pro Phe Glu Ala Arg Leu Asn Ala
            180                 185                 190

Ser Met Gly Pro Gly Arg Thr Val Val Lys Gly Glu Val Asn Thr
        195                 200                 205

Asn Ala Thr Ser Phe Asn Val Asp Leu Val Ala Gly Arg Ser Arg Asp
210                 215                 220

Ile Ala Leu His Leu Asn Pro Arg Leu Asn Val Lys Ala Phe Val Arg
225                 230                 235                 240

Asn Ser Phe Leu Gln Asp Ala Trp Gly Glu Glu Arg Asn Ile Thr
            245                 250                 255

Cys Phe Pro Phe Ser Ser Gly Met Tyr Phe Glu Met Ile Ile Tyr Cys
                260                 265                 270

Asp Val Arg Glu Phe Lys Val Ala Val Asn Gly Val His Ser Leu Glu
            275                 280                 285

Tyr Lys His Arg Phe Lys Asp Leu Ser Ser Ile Asp Thr Leu Ala Val
        290                 295                 300

Asp Gly Asp Ile Arg Leu Leu Asp Val Arg Ser Trp
305                 310                 315

<210> SEQ ID NO 18
<211> LENGTH: 499
<212> TYPE: DNA
<213> ORGANISM: Homo sapiens
<220> FEATURE:
<221> NAME/KEY: misc_feature
<222> LOCATION: (21)
<223> OTHER INFORMATION: n is A, C, T, or G
<221> NAME/KEY: misc_feature
<222> LOCATION: (45)
<223> OTHER INFORMATION: n is A, C, T, or G
<221> NAME/KEY: misc_feature
<222> LOCATION: (422)
<223> OTHER INFORMATION: n is A, C, T, or G
<221> NAME/KEY: misc_feature
<222> LOCATION: (433)
<223> OTHER INFORMATION: n is A, C, T, or G
<221> NAME/KEY: misc_feature
<222> LOCATION: (442)
<223> OTHER INFORMATION: n is A, C, T, or G
<221> NAME/KEY: misc_feature
<222> LOCATION: (454)
<223> OTHER INFORMATION: n is A, C, T, or G
<221> NAME/KEY: misc_feature
```

<222> LOCATION: (457)..(458)
<223> OTHER INFORMATION: n is A, C, T, or G
<221> NAME/KEY: misc_feature
<222> LOCATION: (469)..(470)
<223> OTHER INFORMATION: n is A, C, T, or G
<221> NAME/KEY: misc_feature
<222> LOCATION: (480)
<223> OTHER INFORMATION: n is A, C, T, or G
<221> NAME/KEY: misc_feature
<222> LOCATION: (493)
<223> OTHER INFORMATION: n is A, C, T, or G
<221> NAME/KEY: misc_feature
<222> LOCATION: (498)
<223> OTHER INFORMATION: n is A, C, T, or G

<400> SEQUENCE: 18
aattcggcac gagagctctt ntcacaggac cagccactag cgcanctcga gcgatggcct      60
atgtccccgc accgggctac cagcccacct acaacccgac gctgccttac taccagccca     120
tcccgggcgg gctcaacgtg ggaatgtctg tttacatcca aggagtggcc agcgagcaca     180
tgaagcggtt cttcgtgaac tttgtggttg ggcaggatcc gggctcagac gtcgccttcc     240
acttcaatcc gcggtttgac ggctgggaca aggtggtctt caacacgttg cagggcggga     300
agtggggcag cgaggagagg aagaggagca tgcccttcaa aaagggtgcc gcctttgagc     360
ttggtcttca tagtcctngg ttgagcacta caaggtngtn gtaaatggaa tccctctatg     420 antagggggac cgntttccct anaattgtaa ccanctnnaa ttgatgggnn tcaattaatn     480
atcaattatt ggnggcanc                                                 499

<210> SEQ ID NO 19
<211> LENGTH: 391
<212> TYPE: DNA
<213> ORGANISM: Homo sapiens
<220> FEATURE:
<221> NAME/KEY: misc_feature
<222> LOCATION: (175)
<223> OTHER INFORMATION: n is A, C, T, or G
<221> NAME/KEY: misc_feature
<222> LOCATION: (364)
<223> OTHER INFORMATION: n is A, C, T, or G
<221> NAME/KEY: misc_feature
<222> LOCATION: (378)
<223> OTHER INFORMATION: n is A, C, T, or G

<400> SEQUENCE: 19
agtggatggg gatctgcaac ttcaatcaat caacttcatc ggaggccagc ccctccggcc      60
ccagggaccc ccgatgatgc caccttaccc tggtcccgga cattgccatc aacagctgaa     120
cagcctgccc accatggaag daccccccaac cttcaacccg cctgtgccat atttngggag     180
gctgcaagga gggctcacag ctcgaagaac catcatcatc aagggctatg tgcctcccac     240
aggcaagagc tttgctatca acttcaaggt gggctcctca ggggacatag ctctgcacat     300
taatccccgc atgggcaacg gtaccgtggt ccggaacagc cttcttgaat ggttcgtggg     360
gttncgagga gaagaagntc acccacaacc c                                   391

<210> SEQ ID NO 20
<211> LENGTH: 423
<212> TYPE: DNA
<213> ORGANISM: Homo sapiens
<220> FEATURE:
<221> NAME/KEY: misc_feature
<222> LOCATION: (309)
<223> OTHER INFORMATION: n is A, C, T, or G
<221> NAME/KEY: misc_feature
<222> LOCATION: (328)
<223> OTHER INFORMATION: n is A, C, T, or G
<221> NAME/KEY: misc_feature
<222> LOCATION: (335)
<223> OTHER INFORMATION: n is A, C, T, or G
<221> NAME/KEY: misc_feature
<222> LOCATION: (345)
<223> OTHER INFORMATION: n is A, C, T, or G
<221> NAME/KEY: misc_feature
<222> LOCATION: (353)
<223> OTHER INFORMATION: n is A, C, T, or G
<221> NAME/KEY: misc_feature
<222> LOCATION: (361)
<223> OTHER INFORMATION: n is A, C, T, or G
<221> NAME/KEY: misc_feature
<222> LOCATION: (371)
<223> OTHER INFORMATION: n is A, C, T, or G

<400> SEQUENCE: 20

```
ccggccccag ggaccccega tgatgccacc ttaccctggt cccggacatt gccatcaaca      60
gctgaacagc ctgcccacca tggaaggacc cccaaccttc aacccgcctg tgccatattt     120
cgggaggctg caaggagggc tcacagctcg aagaaccatc atcatcaagg gctatgtgcc     180
tcccacaggc aagagctttg ctatcaactt caaggtgggc tcctcagggg acatagctct     240
gcacattaat ccccgcatgg gcaacggtac cgtggtccgg aacagncttc tgaatggctc     300
gtggggatnc gaggagaagg aaggtcancc acaanccatt ttgtnccgga canttttttt     360
natctgtcca nttggttgtg gtttggatcg tttcaaggtt taaggcaatg ccagaactt     420
ttt                                                                    423
```

<210> SEQ ID NO 21
<211> LENGTH: 434
<212> TYPE: DNA
<213> ORGANISM: Homo sapiens
<220> FEATURE:
<221> NAME/KEY: misc_feature
<222> LOCATION: (266)
<223> OTHER INFORMATION: n is A, C, T, or G
<221> NAME/KEY: misc_feature
<222> LOCATION: (296)
<223> OTHER INFORMATION: n is A, C, T, or G
<221> NAME/KEY: misc_feature
<222> LOCATION: (378)
<223> OTHER INFORMATION: n is A, C, T, or G
<221> NAME/KEY: misc_feature
<222> LOCATION: (380)
<223> OTHER INFORMATION: n is A, C, T, or G

<400> SEQUENCE: 21

```
aattcggcac gagcacaggc aagagctttg ctatcaactt caaggtgggc tcctcagggg      60
acatagctct gcacattaat ccccgcatgg gcaacggtac cgtggtccgg aacagccttc     120
tgaatggctc gtggggatcc gaggagaaga agatcaccca caacccattt ggtcccggac     180
agttctttga tctgtccatt cgctgtggct tggatcgctt caaggtttac ggcaatggcc     240
agcacctctt tgactttgcc catcgnctct cggccttcca gagggtggac anattngaaa     300
tccagggtga tgtcaacttg tcctatgtcc agatctaatc ttattcctgg ggccataatt     360
catgggaaac agattatncn ctagggttct tttttaggcc ctaataaaat gtcttagggg     420
ggtaaaaaaa aaaa                                                        434
```

<210> SEQ ID NO 22
<211> LENGTH: 354
<212> TYPE: DNA
<213> ORGANISM: Homo sapiens
<220> FEATURE:
<221> NAME/KEY: misc_feature
<222> LOCATION: (238)

```
<223> OTHER INFORMATION: n is A, C, T, or G
<221> NAME/KEY: misc_feature
<222> LOCATION: (269)
<223> OTHER INFORMATION: n is A, C, T, or G
<221> NAME/KEY: misc_feature
<222> LOCATION: (276)
<223> OTHER INFORMATION: n is A, C, T, or G
<221> NAME/KEY: misc_feature
<222> LOCATION: (318)
<223> OTHER INFORMATION: n is A, C, T, or G

<400> SEQUENCE: 22
cttcaatccg cggtttgacg gctgggacaa ggtggtcttc aacacgttgc agggcgggaa      60
gtggggcagc gaggagagga agaggagcat gcccttcaaa aagggtgccg cctttaagct     120
ggtcttcata gtcctggctg agcactacaa ggtggtggta aatggaaatc ccttctatga     180
gtacgggcac cggcttcccc tacagatggt cacccacctg caagtggatg gggatctnca     240
acttcaatca atcaacttca tcgggaggnc agcccntccg gccccaggga ccccgatga     300 tgccacctta ccctggtncc ggacattggc catcagcagt tgaacagctg tcca          354

<210> SEQ ID NO 23
<211> LENGTH: 329
<212> TYPE: DNA
<213> ORGANISM: Homo sapiens
<220> FEATURE:
<221> NAME/KEY: misc_feature
<222> LOCATION: (244)
<223> OTHER INFORMATION: n is A, C, T, or G
<221> NAME/KEY: misc_feature
<222> LOCATION: (303)
<223> OTHER INFORMATION: n is A, C, T, or G
<221> NAME/KEY: misc_feature
<222> LOCATION: (314)
<223> OTHER INFORMATION: n is A, C, T, or G

<400> SEQUENCE: 23
gtggtccgga acagccttct gaatggctcg tggggatccg aggagaagaa gatcacccac      60
aacccatttg gtcccggaca gttctttgat ctgtccattc gctgtggctt ggatcgcttc     120
aaggtttacg ccaatggcca gcacctcttt gactttgccc atcgcctctc ggccttccag     180
agggtggaca cattggaaat ccagggtgat gtcaccttgt cctatgtcca gatctaatct     240
attnctgggg ccataactca tgggaaaaca gaattatccc ctaggactcc tttctaaagc     300
ccnctaataa aaangtctga gggtgtctc                                       329

<210> SEQ ID NO 24
<211> LENGTH: 229
<212> TYPE: DNA
<213> ORGANISM: Homo sapiens
<220> FEATURE:
<221> NAME/KEY: misc_feature
<222> LOCATION: (186)
<223> OTHER INFORMATION: n is A, C, T, or G

<400> SEQUENCE: 24
gcgggctcaa cgtgggaatg tctgtttaca tccaaggagt ggccagcgag cacatgaagc      60
ggttcttcgt gaactttgtg gttgggcagg atccgggctc agacgtcgcc ttccacttca     120
atccgcggtt tgacgctgg gacaaggtgg tcttcaacac gttgcagggc gggaagtggg     180
gcagcnagga gaggaagagg agcatgccct tcaaaaaggg tgccgcctt                 229

<210> SEQ ID NO 25
<211> LENGTH: 194
<212> TYPE: DNA
```

```
<213> ORGANISM: Homo sapiens
<220> FEATURE:
<221> NAME/KEY: misc_feature
<222> LOCATION: (102)
<223> OTHER INFORMATION: n is A, C, T, or G

<400> SEQUENCE: 25
ggaagaggag catgcccttc aaaaagggtg ccgcctttaa cctggtnttc atagtcctgg      60
ctgagcacta caaggtggtg gtaaatggaa atcccttcta tnagtacggg caccggcttc     120
ccctacagat ggtcacccac ctgcaagtgg atggggatct gcaacttcat tcattcaact    180
tcatcggagg ccag                                                       194

<210> SEQ ID NO 26
<211> LENGTH: 499
<212> TYPE: DNA
<213> ORGANISM: Homo sapiens
<220> FEATURE:
<221> NAME/KEY: misc_feature
<222> LOCATION: (142)
<223> OTHER INFORMATION: n is A, C, T, or G
<221> NAME/KEY: misc_feature
<222> LOCATION: (192)
<223> OTHER INFORMATION: n is A, C, T, or G
<221> NAME/KEY: misc_feature
<222> LOCATION: (238)
<223> OTHER INFORMATION: n is A, C, T, or G
<221> NAME/KEY: misc_feature
<222> LOCATION: (292)
<223> OTHER INFORMATION: n is A, C, T, or G
<221> NAME/KEY: misc_feature
<222> LOCATION: (307)
<223> OTHER INFORMATION: n is A, C, T, or G
<221> NAME/KEY: misc_feature
<222> LOCATION: (336)
<223> OTHER INFORMATION: n is A, C, T, or G
<221> NAME/KEY: misc_feature
<222> LOCATION: (358)
<223> OTHER INFORMATION: n is A, C, T, or G
<221> NAME/KEY: misc_feature
<222> LOCATION: (361)
<223> OTHER INFORMATION: n is A, C, T, or G
<221> NAME/KEY: misc_feature
<222> LOCATION: (363)
<223> OTHER INFORMATION: n is A, C, T, or G
<221> NAME/KEY: misc_feature
<222> LOCATION: (370)
<223> OTHER INFORMATION: n is A, C, T, or G
<221> NAME/KEY: misc_feature
<222> LOCATION: (373)
<223> OTHER INFORMATION: n is A, C, T, or G
<221> NAME/KEY: misc_feature
<222> LOCATION: (378)..(379)
<223> OTHER INFORMATION: n is A, C, T, or G
<221> NAME/KEY: misc_feature
<222> LOCATION: (385)
<223> OTHER INFORMATION: n is A, C, T, or G
<221> NAME/KEY: misc_feature
<222> LOCATION: (389)
<223> OTHER INFORMATION: n is A, C, T, or G
<221> NAME/KEY: misc_feature
<222> LOCATION: (392)
<223> OTHER INFORMATION: n is A, C, T, or G
<221> NAME/KEY: misc_feature
<222> LOCATION: (398)
<223> OTHER INFORMATION: n is A, C, T, or G
<221> NAME/KEY: misc_feature
<222> LOCATION: (403)..(404)
<223> OTHER INFORMATION: n is A, C, T, or G
<221> NAME/KEY: misc_feature
<222> LOCATION: (407)
<223> OTHER INFORMATION: n is A, C, T, or G
<221> NAME/KEY: misc_feature
<222> LOCATION: (415)
<223> OTHER INFORMATION: n is A, C, T, or G
```

<221> NAME/KEY: misc_feature
<222> LOCATION: (417)
<223> OTHER INFORMATION: n is A, C, T, or G
<221> NAME/KEY: misc_feature
<222> LOCATION: (429)
<223> OTHER INFORMATION: n is A, C, T, or G
<221> NAME/KEY: misc_feature
<222> LOCATION: (432)
<223> OTHER INFORMATION: n is A, C, T, or G
<221> NAME/KEY: misc_feature
<222> LOCATION: (434)
<223> OTHER INFORMATION: n is A, C, T, or G
<221> NAME/KEY: misc_feature
<222> LOCATION: (439)
<223> OTHER INFORMATION: n is A, C, T, or G
<221> NAME/KEY: misc_feature
<222> LOCATION: (442)
<223> OTHER INFORMATION: n is A, C, T, or G
<221> NAME/KEY: misc_feature
<222> LOCATION: (452)
<223> OTHER INFORMATION: n is A, C, T, or G
<221> NAME/KEY: misc_feature
<222> LOCATION: (455)..(456)
<223> OTHER INFORMATION: n is A, C, T, or G
<221> NAME/KEY: misc_feature
<222> LOCATION: (465)
<223> OTHER INFORMATION: n is A, C, T, or G
<221> NAME/KEY: misc_feature
<222> LOCATION: (469)
<223> OTHER INFORMATION: n is A, C, T, or G

<400> SEQUENCE: 26

```
aattccgttc tctactcccg ccatcccacc tataatgtac ccccacccg cctatccaat    60
gcctttaatc accaccattc tgggagggct gtacccatcc aagtccatcc tcctgtaagg   120
cacttgcctg cccagtgctc anaggttcca catcaacctg tgctctggga aaccacatcg   180
ccttccacct gnaacccccg ttttgaatga gaatgctgtg gtccgcaaca cccagatnga   240
caactcctgg gggtctgagg agcgaagtgt gccccgaaaa atgcccttgg tncgtggcca   300
gaggttntna ggtggatctt tgtgtgaagtt caatgngtnc aagtgggcct ggatggtnag   360
nantgtttgn atnattannc tgggnttgng gnaactgngc aannttnaac agatngnagt   420
tgggggggng anantcagnt gnaccgtttt gnagnnatag ggggnttnt tggccttggg   480
ggggggggtt ggggttttg                                                499
```

<210> SEQ ID NO 27
<211> LENGTH: 376
<212> TYPE: DNA
<213> ORGANISM: Homo sapiens
<220> FEATURE:
<221> NAME/KEY: misc_feature
<222> LOCATION: (21)
<223> OTHER INFORMATION: n is A, C, T, or G
<221> NAME/KEY: misc_feature
<222> LOCATION: (292)
<223> OTHER INFORMATION: n is A, C, T, or G
<221> NAME/KEY: misc_feature
<222> LOCATION: (333)
<223> OTHER INFORMATION: n is A, C, T, or G
<221> NAME/KEY: misc_feature
<222> LOCATION: (355)
<223> OTHER INFORMATION: n is A, C, T, or G
<221> NAME/KEY: misc_feature
<222> LOCATION: (371)
<223> OTHER INFORMATION: n is A, C, T, or G

<400> SEQUENCE: 27

```
cttttgccaa caagcatttt natttcttta ttttaaggac actgggaaag gagccagtcc    60
cctgaagaga acactctggt caggtggtgg aggccagtgg gaagccatca ggcctgcttt   120
```

```
ccaggagggg tgaagggttg gtgcacggtg caaggtgaga gtgaaggtta aaggtcagag      180 aggagggct gaggaggcca ccttccacca ggagcagaca gctggtggct tgggaactgg      240
ggtggagctg cgtgggggat gggaagggga ctgagcatgg ggcttcatct tncactgccc      300
actcctgccc tcttccctgg ctgtgcctgc ctncctggga tggtagggtt ccancantt     360 ggaggcccca ngtgct                                                     376
```

<210> SEQ ID NO 28
<211> LENGTH: 282
<212> TYPE: DNA
<213> ORGANISM: Homo sapiens
<220> FEATURE:
<221> NAME/KEY: misc_feature
<222> LOCATION: (51)
<223> OTHER INFORMATION: n is A, C, T, or G
<221> NAME/KEY: misc_feature
<222> LOCATION: (142)
<223> OTHER INFORMATION: n is A, C, T, or G

<400> SEQUENCE: 28

```
ttcagatcac tgtcaatggg accgttctca gctccagtgg aaccaggttt nctgtgaact     60
ttcagactgg cttcagtgga ataacattg ccttccactt caaccctcgg tttgaagatg     120
gagggtacgt ggtgtgcaca gnaggcagaa cggaagctgg gggcccgagg agaggaagac    180
acacatgcct ttccagaagg ggatgccctt taacctctgc ttcctggtgc agagctcaga    240
tttcaaggtg atggtgaacg ggatcctctt cgtgcagtac tt                        282
```

<210> SEQ ID NO 29
<211> LENGTH: 274
<212> TYPE: DNA
<213> ORGANISM: Homo sapiens
<220> FEATURE:
<221> NAME/KEY: misc_feature
<222> LOCATION: (26)
<223> OTHER INFORMATION: n is A, C, T, or G
<221> NAME/KEY: misc_feature
<222> LOCATION: (84)
<223> OTHER INFORMATION: n is A, C, T, or G

<400> SEQUENCE: 29

```
gtgcagagcg cccctggaca gatgtnctct actcccgcca tcccacctat gatgtacccc     60
caccccgcct atccgatgcc tttnaacacc accattctgg gagggctgta cccatccaag    120
atccatcctc ctgtcaggca ctgtcctgcc cagtgctcag aggttccaca tcaacctgtg    180
ctctgggaac cacatcgcct tccacctgaa ccccgttttt gatgagaatg ctgtggtccg    240
caacacccag atcgacaaat tcctgggggg tctt                                 274
```

<210> SEQ ID NO 30
<211> LENGTH: 342
<212> TYPE: DNA
<213> ORGANISM: Homo sapiens
<220> FEATURE:
<221> NAME/KEY: misc_feature
<222> LOCATION: (21)
<223> OTHER INFORMATION: n is A, C, T, or G
<221> NAME/KEY: misc_feature
<222> LOCATION: (163)
<223> OTHER INFORMATION: n is A, C, T, or G
<221> NAME/KEY: misc_feature
<222> LOCATION: (256)
<223> OTHER INFORMATION: n is A, C, T, or G
<221> NAME/KEY: misc_feature
<222> LOCATION: (266)
<223> OTHER INFORMATION: n is A, C, T, or G
<221> NAME/KEY: misc_feature
<222> LOCATION: (298)
<223> OTHER INFORMATION: n is A, C, T, or G
<221> NAME/KEY: misc_feature
<222> LOCATION: (333)
<223> OTHER INFORMATION: n is A, C, T, or G
<221> NAME/KEY: misc_feature
<222> LOCATION: (337)
<223> OTHER INFORMATION: n is A, C, T, or G

<400> SEQUENCE: 30

| | | | | | |
|---|---|---|---|---|---|
| cttttgccaa | caagcatttt | natttcttta | ttttaaggac | actgggaaag | gagccagtcc | 60
| cctgaagaga | acactctggt | caggtggtgg | aggccagtgg | gaagccatca | ggcctgcttt | 120
| ccaggagggg | tgaagggttg | gtgcacggtg | caaggtgaga | gtnaaggtta | aaggtcagag | 180
| aggaggggct | gaggaggcca | ccttccacca | ggagcagaca | gctggtggct | tgggaactgg | 240
| ggtgggagct | gtcgtngggg | gatggnaagg | ggactgagcc | atgggggctt | tcatcttnca | 300
| ctgcccactc | ctgccctttt | ccctggtttg | tgnctgncct | tc | | 342

<210> SEQ ID NO 31
<211> LENGTH: 246
<212> TYPE: DNA
<213> ORGANISM: Homo sapiens
<220> FEATURE:
<221> NAME/KEY: misc_feature
<222> LOCATION: (23)
<223> OTHER INFORMATION: n is A, C, T, or G
<221> NAME/KEY: misc_feature
<222> LOCATION: (59)
<223> OTHER INFORMATION: n is A, C, T, or G
<221> NAME/KEY: misc_feature
<222> LOCATION: (99)
<223> OTHER INFORMATION: n is A, C, T, or G
<221> NAME/KEY: misc_feature
<222> LOCATION: (156)
<223> OTHER INFORMATION: n is A, C, T, or G
<221> NAME/KEY: misc_feature
<222> LOCATION: (212)
<223> OTHER INFORMATION: n is A, C, T, or G

<400> SEQUENCE: 31

| | | | | | |
|---|---|---|---|---|---|
| cctgcttctg | gctacagcca | ccntggaacg | gagaaggcag | ctgacgggga | ttgccttcnt | 60
| cagccgcagc | agcacctggg | gctccagctg | ctggaatcnt | accatcccag | gaggcaggca | 120
| cagccaggga | gagggagga | gtgggcagtg | aagatnaagc | cccatgctca | gtcccctccc | 180
| atccccacg | cagctccacc | ccagttccaa | gnaccagct | gtctgctcct | ggtgggaggt | 240
| ggcctc | | | | | | 246

<210> SEQ ID NO 32
<211> LENGTH: 228
<212> TYPE: DNA
<213> ORGANISM: Homo sapiens
<220> FEATURE:
<221> NAME/KEY: misc_feature
<222> LOCATION: (5)
<223> OTHER INFORMATION: n is A, C, T, or G
<221> NAME/KEY: misc_feature
<222> LOCATION: (24)
<223> OTHER INFORMATION: n is A, C, T, or G
<221> NAME/KEY: misc_feature
<222> LOCATION: (26)
<223> OTHER INFORMATION: n is A, C, T, or G
<221> NAME/KEY: misc_feature
<222> LOCATION: (189)
<223> OTHER INFORMATION: n is A, C, T, or G
<221> NAME/KEY: misc_feature
<222> LOCATION: (192)
<223> OTHER INFORMATION: n is A, C, T, or G
<221> NAME/KEY: misc_feature

```
<222> LOCATION: (200)
<223> OTHER INFORMATION: n is A, C, T, or G
<221> NAME/KEY: misc_feature
<222> LOCATION: (213)
<223> OTHER INFORMATION: n is A, C, T, or G
<221> NAME/KEY: misc_feature
<222> LOCATION: (218)
<223> OTHER INFORMATION: n is A, C, T, or G
<221> NAME/KEY: misc_feature
<222> LOCATION: (223)
<223> OTHER INFORMATION: n is A, C, T, or G
<221> NAME/KEY: misc_feature
<222> LOCATION: (226)
<223> OTHER INFORMATION: n is A, C, T, or G

<400> SEQUENCE: 32
ggcanagcag aggtgtggat cttntntaaa gctcactgcc tcaaggtggc cgtggatggt      60
cagcacctgt ttaaatacta ccatcgcctg aggaacctgc ccaccatcaa cagactggga    120 gtgggggcg aacatccagc tgacccatgt gcagacatag gcggcttcct ggccctgggg    180
cgggggctna gntttggggn agtctgggtc ctntaatnat ccncantt                 228

<210> SEQ ID NO 33
<211> LENGTH: 161
<212> TYPE: DNA
<213> ORGANISM: Homo sapiens
<220> FEATURE:
<221> NAME/KEY: misc_feature
<222> LOCATION: (32)
<223> OTHER INFORMATION: n is A, C, T, or G
<221> NAME/KEY: misc_feature
<222> LOCATION: (52)
<223> OTHER INFORMATION: n is A, C, T, or G

<400> SEQUENCE: 33
ttccctctac aaaggacttc ctagtgggtg tnaaaggcag cggtggccac anaggcggcg     60
gagagatggc cttcagcggt tcccaggctc cctacctgag tccagctgtc cccttttttg   120
ggactattca aggaggtctc caggacggac ttcagatcac t                       161

<210> SEQ ID NO 34
<211> LENGTH: 306
<212> TYPE: DNA
<213> ORGANISM: Homo sapiens
<220> FEATURE:
<221> NAME/KEY: misc_feature
<222> LOCATION: (33)..(34)
<223> OTHER INFORMATION: n is A, C, T, or G
<221> NAME/KEY: misc_feature
<222> LOCATION: (57)
<223> OTHER INFORMATION: n is A, C, T, or G
<221> NAME/KEY: misc_feature
<222> LOCATION: (80)
<223> OTHER INFORMATION: n is A, C, T, or G
<221> NAME/KEY: misc_feature
<222> LOCATION: (101)
<223> OTHER INFORMATION: n is A, C, T, or G
<221> NAME/KEY: misc_feature
<222> LOCATION: (103)
<223> OTHER INFORMATION: n is A, C, T, or G
<221> NAME/KEY: misc_feature
<222> LOCATION: (118)..(119)
<223> OTHER INFORMATION: n is A, C, T, or G
<221> NAME/KEY: misc_feature
<222> LOCATION: (123)
<223> OTHER INFORMATION: n is A, C, T, or G
<221> NAME/KEY: misc_feature
<222> LOCATION: (126)
<223> OTHER INFORMATION: n is A, C, T, or G
<221> NAME/KEY: misc_feature
<222> LOCATION: (134)
<223> OTHER INFORMATION: n is A, C, T, or G
```

<221> NAME/KEY: misc_feature
<222> LOCATION: (189)
<223> OTHER INFORMATION: n is A, C, T, or G
<221> NAME/KEY: misc_feature
<222> LOCATION: (191)
<223> OTHER INFORMATION: n is A, C, T, or G
<221> NAME/KEY: misc_feature
<222> LOCATION: (214)
<223> OTHER INFORMATION: n is A, C, T, or G
<221> NAME/KEY: misc_feature
<222> LOCATION: (269)
<223> OTHER INFORMATION: n is A, C, T, or G
<221> NAME/KEY: misc_feature
<222> LOCATION: (287)
<223> OTHER INFORMATION: n is A, C, T, or G
<221> NAME/KEY: misc_feature
<222> LOCATION: (290)
<223> OTHER INFORMATION: n is A, C, T, or G
<221> NAME/KEY: misc_feature
<222> LOCATION: (295)
<223> OTHER INFORMATION: n is A, C, T, or G

<400> SEQUENCE: 34

| | | | | | |
|---|---|---|---|---|---|
| ctctgtgcag | ctgtcctaca | tcagcttcca | ggnnagactg | tccacctggc | accggtncca | 60 |
| ggggcgggga | atgcgggghg | nagcgtagtt | gatactgaag | ncnctgatgg | gtggggcnna | 120 |
| agncanatct | cctnacccag | gtcactctgg | gggacaacct | ctggcttccc | tgtcccagta | 180 |
| cctggctgnc | nacttctcct | ctgtgaactc | tgancctcc | ttctgtgttt | actgtctctg | 240 |
| tccggaacaa | ctgccttggt | ctcccagant | gctcaggtga | ccctttnttn | tttcnaccct | 300 |
| tcaatt | | | | | | 306 |

<210> SEQ ID NO 35
<211> LENGTH: 449
<212> TYPE: DNA
<213> ORGANISM: Homo sapiens
<220> FEATURE:
<221> NAME/KEY: misc_feature
<222> LOCATION: (89)
<223> OTHER INFORMATION: n is A, C, T, or G
<221> NAME/KEY: misc_feature
<222> LOCATION: (280)
<223> OTHER INFORMATION: n is A, C, T, or G
<221> NAME/KEY: misc_feature
<222> LOCATION: (336)
<223> OTHER INFORMATION: n is A, C, T, or G
<221> NAME/KEY: misc_feature
<222> LOCATION: (388)
<223> OTHER INFORMATION: n is A, C, T, or G
<221> NAME/KEY: misc_feature
<222> LOCATION: (400)
<223> OTHER INFORMATION: n is A, C, T, or G

<400> SEQUENCE: 35

| | | | | | |
|---|---|---|---|---|---|
| ctcatacaga | gggcatcggg | tcccaccctg | tcactcattt | catcgtctaa | aatgtaatca | 60 |
| tgagtgtttg | cttcgagcca | gggacagtnc | tgctgcaggg | gacccagctg | ggaccaaggc | 120 |
| agactgtctc | tcccctcctg | ggatttacag | ggtcatggct | ctgaaacatt | ctgtagtgtt | 180 |
| ctttgaacac | gagttttccc | tggagatcgc | tttctgcagg | cctcttggtc | ctgactgtgg | 240 |
| cttcttttca | gagcctgcca | ttcgctgcaa | ggttgaacan | cccatgggc | cctgggacga | 300 |
| actgtcgtcg | ttaaaaggag | aagtgaatgc | aaatgnccaa | aaagcttta | atgtttgacc | 360 |
| tactagcagg | aaatcaaagg | gtattgcntc | ttacaattgn | acccaggctg | aatattaaag | 420 |
| cattttaaag | aattcttttt | cttcaggag | | | | 449 |

<210> SEQ ID NO 36
<211> LENGTH: 265

```
<212> TYPE: DNA
<213> ORGANISM: Homo sapiens
<220> FEATURE:
<221> NAME/KEY: misc_feature
<222> LOCATION: (48)
<223> OTHER INFORMATION: n is A, C, T, or G
<221> NAME/KEY: misc_feature
<222> LOCATION: (115)
<223> OTHER INFORMATION: n is A, C, T, or G

<400> SEQUENCE: 36
ttcaatcctc gtttcaaaag ggccggctgc attgtttgca atactttnat aaatgaaaaa      60
tggggacggg aagagatcac ctatgacacg cctttcaaaa gagaaaagtc ttttnagatc     120
gtaattatgg tgctgaagga caaattccag gtggctgtaa atggaaaaca tactctgctc     180
tatggccaca ggatcggccc agagaaaata gacactctgg gcatttatgg caaagtgaat     240
attcactcaa ttggttttag cttca                                           265

<210> SEQ ID NO 37
<211> LENGTH: 353
<212> TYPE: DNA
<213> ORGANISM: Homo sapiens
<220> FEATURE:
<221> NAME/KEY: misc_feature
<222> LOCATION: (323)
<223> OTHER INFORMATION: n is A, C, T, or G

<400> SEQUENCE: 37
aagccactct gccctctctc ctactttggc tgactcttca agaatgccat tcaacaagta      60
tttatggagt acctactata atacagtagc taacatgtat tgagcacaga ttttttttgg     120
taaaactgtg aggagctagg atatatactt ggtgaaacaa accagtatgt tccctgttct     180
cttgagcttc gactcttctg tgctctattg ctgcgcactg cttttttcta caggcattaca    240 tcaactccta aggggtcctc tggggattag ttaagcagct atttaaatca cccgaaggac     300
acttaattta cagatgacac aantcctttc cccagtgatt caactgttca taa            353

<210> SEQ ID NO 38
<211> LENGTH: 234
<212> TYPE: DNA
<213> ORGANISM: Homo sapiens
<220> FEATURE:
<221> NAME/KEY: misc_feature
<222> LOCATION: (12)
<223> OTHER INFORMATION: n is A, C, T, or G
<221> NAME/KEY: misc_feature
<222> LOCATION: (25)
<223> OTHER INFORMATION: n is A, C, T, or G
<221> NAME/KEY: misc_feature
<222> LOCATION: (31)
<223> OTHER INFORMATION: n is A, C, T, or G
<221> NAME/KEY: misc_feature
<222> LOCATION: (54)
<223> OTHER INFORMATION: n is A, C, T, or G
<221> NAME/KEY: misc_feature
<222> LOCATION: (72)
<223> OTHER INFORMATION: n is A, C, T, or G
<221> NAME/KEY: misc_feature
<222> LOCATION: (149)
<223> OTHER INFORMATION: n is A, C, T, or G
<221> NAME/KEY: misc_feature
<222> LOCATION: (178)
<223> OTHER INFORMATION: n is A, C, T, or G

<400> SEQUENCE: 38
gaaacaccag tntttggggc cagtnccctca ntttcaatcc aggtaaccttt taantgaaac    60 ttgcctaaaa tnttaggtca tacacagaag agactccaat cgacaagaag ctggaaaaga   120
```
atgatgttgt ccttaaacaa cctacagant atcatctata acccgtaat cccgttttntt    180 ggcaccattc ctgatcagct ggatcctgga actttgattg taatacgtgg gcat           234

<210> SEQ ID NO 39
<211> LENGTH: 344
<212> TYPE: DNA
<213> ORGANISM: Homo sapiens
<220> FEATURE:
<221> NAME/KEY: misc_feature
<222> LOCATION: (45)
<223> OTHER INFORMATION: n is A, C, T, or G
<221> NAME/KEY: misc_feature
<222> LOCATION: (47)
<223> OTHER INFORMATION: n is A, C, T, or G

<400> SEQUENCE: 39
acacgctgga aattaatgga gacatccact tactggaagt aaggngntgg tagcctacct      60
acacagctgc tacaaaaacc aaaatacaga atggcttctg tgatactggc cttgctgaaa    120
cgcatctcac tgtcattcta ttgtttatat tgttaaaatg agcttgtgca ccattaggtc    180
ctgctgggtg ttctcagtcc ttgccatgaa gtatggtggt gtctagcact gaatggggaa    240
actgggggca gcaacactta tagccagtta aagccactct gccctctctc ctactttggg    300
ctgactcttc aagaatgcca ttcaacaagt atttatgggg tacc                      344

<210> SEQ ID NO 40
<211> LENGTH: 502
<212> TYPE: DNA
<213> ORGANISM: Homo sapiens
<220> FEATURE:
<221> NAME/KEY: misc_feature
<222> LOCATION: (10)
<223> OTHER INFORMATION: n is A, C, T, or G
<221> NAME/KEY: misc_feature
<222> LOCATION: (71)
<223> OTHER INFORMATION: n is A, C, T, or G
<221> NAME/KEY: misc_feature
<222> LOCATION: (83)
<223> OTHER INFORMATION: n is A, C, T, or G
<221> NAME/KEY: misc_feature
<222> LOCATION: (151)
<223> OTHER INFORMATION: n is A, C, T, or G
<221> NAME/KEY: misc_feature
<222> LOCATION: (184)
<223> OTHER INFORMATION: n is A, C, T, or G
<221> NAME/KEY: misc_feature
<222> LOCATION: (252)
<223> OTHER INFORMATION: n is A, C, T, or G
<221> NAME/KEY: misc_feature
<222> LOCATION: (297)
<223> OTHER INFORMATION: n is A, C, T, or G
<221> NAME/KEY: misc_feature
<222> LOCATION: (330)
<223> OTHER INFORMATION: n is A, C, T, or G
<221> NAME/KEY: misc_feature
<222> LOCATION: (335)
<223> OTHER INFORMATION: n is A, C, T, or G
<221> NAME/KEY: misc_feature
<222> LOCATION: (370)
<223> OTHER INFORMATION: n is A, C, T, or G
<221> NAME/KEY: misc_feature
<222> LOCATION: (374)
<223> OTHER INFORMATION: n is A, C, T, or G
<221> NAME/KEY: misc_feature
<222> LOCATION: (381)
<223> OTHER INFORMATION: n is A, C, T, or G
<221> NAME/KEY: misc_feature
<222> LOCATION: (387)..(388)
<223> OTHER INFORMATION: n is A, C, T, or G
<221> NAME/KEY: misc_feature
<222> LOCATION: (415)

```
<223> OTHER INFORMATION: n is A, C, T, or G
<221> NAME/KEY: misc_feature
<222> LOCATION: (434)
<223> OTHER INFORMATION: n is A, C, T, or G
<221> NAME/KEY: misc_feature
<222> LOCATION: (439)
<223> OTHER INFORMATION: n is A, C, T, or G
<221> NAME/KEY: misc_feature
<222> LOCATION: (451)
<223> OTHER INFORMATION: n is A, C, T, or G
<221> NAME/KEY: misc_feature
<222> LOCATION: (454)..(455)
<223> OTHER INFORMATION: n is A, C, T, or G
<221> NAME/KEY: misc_feature
<222> LOCATION: (458)
<223> OTHER INFORMATION: n is A, C, T, or G
<221> NAME/KEY: misc_feature
<222> LOCATION: (461)
<223> OTHER INFORMATION: n is A, C, T, or G
<221> NAME/KEY: misc_feature
<222> LOCATION: (475)
<223> OTHER INFORMATION: n is A, C, T, or G

<400> SEQUENCE: 40
aattcggcan agcttcaaac ctttgagaca tagttcatag gtggtatttt ggtgcaagtc      60
aaagtgtgat ngacagtcga atntttgctc ttggtgtaga cagttctggg tgcgatttta    120
gaaatgtctg ctcctctatt actaggctgt ngggaaacag ttctacagta aggaatggaa    180
tganatgaag ctgccctcca cggtttaaac tgttcatttt ctatgcaact ttataaaata    240
ttccacatga antaacccag gcaaaaatac ttcacaggct gggggggcgtg ccaganctt    300 tgggaaccta ttgggaaaag gaaaccaaan cacancaatg tttagaaggg ggaaggattt    360
ttagtttatn aatntgaagt nttgggnngt tgctgaggct gaggcctggg ccggnggctt    420
ggggattgtt tccnggttnc cactctggtg nggnnttncc ngggcagttg ggtgnttta    480 tgacgggatt ggtattgtgt tg                                             502

<210> SEQ ID NO 41
<211> LENGTH: 26
<212> TYPE: DNA
<213> ORGANISM: synthetic construct

<400> SEQUENCE: 41
cgcccatggc ctatgtcccc gcaccg                                          26

<210> SEQ ID NO 42
<211> LENGTH: 28
<212> TYPE: DNA
<213> ORGANISM: synthetic construct

<400> SEQUENCE: 42
cgcaagcttt tagatctgga cataggac                                        28

<210> SEQ ID NO 43
<211> LENGTH: 26
<212> TYPE: DNA
<213> ORGANISM: synthetic construct

<400> SEQUENCE: 43
cgcccatggc cttcagcggt tcccag                                          26

<210> SEQ ID NO 44
<211> LENGTH: 26
<212> TYPE: DNA
<213> ORGANISM: synthetic construct
```

<400> SEQUENCE: 44
cgcaagcttc agggttggaa aggctg                                        26

<210> SEQ ID NO 45
<211> LENGTH: 26
<212> TYPE: DNA
<213> ORGANISM: synthetic construct

<400> SEQUENCE: 45
cgcccatgct gttgtcctta aacaac                                        26

<210> SEQ ID NO 46
<211> LENGTH: 25
<212> TYPE: DNA
<213> ORGANISM: synthetic construct

<400> SEQUENCE: 46
cgcctgcagc acagaagcca ttctg                                         25

<210> SEQ ID NO 47
<211> LENGTH: 33
<212> TYPE: DNA
<213> ORGANISM: synthetic construct

<400> SEQUENCE: 47
cgcctgcagc tatgcaactt tataaaatat tcc                                33

<210> SEQ ID NO 48
<211> LENGTH: 25
<212> TYPE: DNA
<213> ORGANISM: synthetic construct

<400> SEQUENCE: 48
cgccccgggg cctatgtccc cgcac                                         25

<210> SEQ ID NO 49
<211> LENGTH: 28
<212> TYPE: DNA
<213> ORGANISM: synthetic construct

<400> SEQUENCE: 49
cgcggtacct tagatctgga cataggac                                      28

<210> SEQ ID NO 50
<211> LENGTH: 27
<212> TYPE: DNA
<213> ORGANISM: synthetic construct

<400> SEQUENCE: 50
cgccccgggg ccttcagcgg ttcccag                                       27

<210> SEQ ID NO 51
<211> LENGTH: 26
<212> TYPE: DNA
<213> ORGANISM: synthetic construct

<400> SEQUENCE: 51
cgcggtaccc agggttggaa aggctg                                        26

<210> SEQ ID NO 52
<211> LENGTH: 28
<212> TYPE: DNA
<213> ORGANISM: synthetic construct -continued

```
<400> SEQUENCE: 52
cgccccgggt tgtccttaaa caacctac                                        28

<210> SEQ ID NO 53
<211> LENGTH: 25
<212> TYPE: DNA
<213> ORGANISM: synthetic construct

<400> SEQUENCE: 53
cgcggtaccc acagaagcca ttctg                                           25

<210> SEQ ID NO 54
<211> LENGTH: 33
<212> TYPE: DNA
<213> ORGANISM: synthetic construct

<400> SEQUENCE: 54
cgcggtaccc tatgcaactt tataaaatat tcc                                  33

<210> SEQ ID NO 55
<211> LENGTH: 31
<212> TYPE: DNA
<213> ORGANISM: synthetic construct

<400> SEQUENCE: 55
cgccccgggg ccatcatggc ctatgtcccc g                                    31

<210> SEQ ID NO 56
<211> LENGTH: 28
<212> TYPE: DNA
<213> ORGANISM: synthetic construct

<400> SEQUENCE: 56
cgcggtacct tagatctgga cataggac                                        28

<210> SEQ ID NO 57
<211> LENGTH: 32
<212> TYPE: DNA
<213> ORGANISM: synthetic construct

<400> SEQUENCE: 57
cgccccgggg ccatcatggc cttcagcggt tc                                   32

<210> SEQ ID NO 58
<211> LENGTH: 26
<212> TYPE: DNA
<213> ORGANISM: synthetic construct

<400> SEQUENCE: 58
cgcggtaccc agggttggaa aggctg                                          26

<210> SEQ ID NO 59
<211> LENGTH: 33
<212> TYPE: DNA
<213> ORGANISM: synthetic construct

<400> SEQUENCE: 59
cgccccgggg ccatcatgat gttgtcctta aac                                  33

<210> SEQ ID NO 60
<211> LENGTH: 25
<212> TYPE: DNA
```

```
<213> ORGANISM: synthetic construct

<400> SEQUENCE: 60
cgcggtaccc acagaagcca ttctg                                    25
```